(12) United States Patent
Fallaux et al.

(10) Patent No.: US 7,105,346 B2
(45) Date of Patent: *Sep. 12, 2006

(54) PACKAGING SYSTEMS FOR HUMAN RECOMBINANT ADENOVIRUS TO BE USED IN GENE THERAPY

(75) Inventors: Frits J. Fallaux, Leiderdorp (NL); Robert C. Hoeben, Leiden (NL); Alex Jan van der Eb, Oegstgeest (NL); Abraham Bout, Moerkapelle (NL); Domenico Valerio, Oegstgeest (NL)

(73) Assignee: Crucell Holland B.V., Leiden (NL)

( * ) Notice: Subject to any disclaimer, the term of this patent is extended or adjusted under 35 U.S.C. 154(b) by 118 days.

This patent is subject to a terminal disclaimer.

(21) Appl. No.: 10/125,751

(22) Filed: Apr. 18, 2002

(65) Prior Publication Data

US 2002/0173039 A1 Nov. 21, 2002

Related U.S. Application Data

(60) Continuation of application No. 09/506,548, filed on Feb. 16, 2000, now Pat. No. 6,602,706, which is a division of application No. 09/334,765, filed on Jun. 16, 1999, now Pat. No. 6,238,893, which is a continuation of application No. 08/793,170, filed as application No. PCT/NL96/00244 on Jun. 14, 1996, now Pat. No. 5,994,128.

(30) Foreign Application Priority Data

Jun. 15, 1995  (EP)  .................................. 95201611
Jun. 26, 1995  (EP)  .................................. 95201728

(51) Int. Cl.
*C12N 5/08* (2006.01)
*C12N 5/10* (2006.01)
*C12N 15/70* (2006.01)
*C12N 15/34* (2006.01)
*C12N 15/861* (2006.01)

(52) U.S. Cl. .................. 435/366; 435/91.4; 435/320.1; 435/455; 435/456; 536/23.72

(58) Field of Classification Search ............... 536/23.1, 536/23.7; 435/320.1, 91.4, 455, 69.1, 325, 435/363, 366, 369; 424/93.2; 514/44
See application file for complete search history.

(56) References Cited

U.S. PATENT DOCUMENTS

| 4,405,712 A | 9/1983 | Vande Woude et al. |
| 4,487,829 A | 12/1984 | Sharp et al. |
| 4,497,796 A | 2/1985 | Salser et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |
| 4,727,028 A | 2/1988 | Santerre et al. |
| 4,740,463 A | 4/1988 | Weinberg et al. |
| 4,792,525 A | 12/1988 | Ruoslahti et al. |
| 4,797,368 A | 1/1989 | Carter et al. |
| 4,956,281 A | 9/1990 | Wallner et al. |
| 5,024,939 A | 6/1991 | Gorman |
| 5,096,815 A | 3/1992 | Ladner et al. |
| 5,166,320 A | 11/1992 | Wu et al. |
| 5,190,931 A | 3/1993 | Inouye |
| 5,198,346 A | 3/1993 | Ladner et al. |
| 5,204,445 A | 4/1993 | Plow et al. |
| 5,208,149 A | 5/1993 | Inouye |
| 5,223,394 A | 6/1993 | Wallner |
| 5,223,409 A | 6/1993 | Ladner et al. |
| 5,240,846 A | 8/1993 | Collins et al. |
| 5,246,921 A | 9/1993 | Reddy et al. |
| 5,332,567 A | 7/1994 | Goldenberg |
| 5,349,053 A | 9/1994 | Landolfi |
| 5,378,618 A | 1/1995 | Sternberg et al. |
| 5,403,484 A | 4/1995 | Ladner et al. |
| 5,436,146 A | 7/1995 | Shenk et al. |
| 5,443,953 A | 8/1995 | Hansen et al. |
| 5,474,935 A | 12/1995 | Chatterjee et al. |
| 5,518,913 A | 5/1996 | Massie et al. |
| 5,521,291 A | 5/1996 | Curiel et al. |
| 5,534,423 A | 7/1996 | Palsson et al. |

(Continued)

FOREIGN PATENT DOCUMENTS

AU    A-28533/95    3/1996

(Continued)

OTHER PUBLICATIONS

Chroboczek et al., The Sequence of the Genome of Adenovirus Type 5 and Its Comparison with the Genome of Adenovirus Type 2, Virology, 1992, pp. 280-285, vol. 186.

(Continued)

*Primary Examiner*—Scott D. Priebe
(74) *Attorney, Agent, or Firm*—TraskBritt

(57) ABSTRACT

Presented are ways to address the problem of replication competent adenovirus in adenoviral production for use with, for example, gene therapy. Packaging cells having no overlapping sequences with a selected vector are suited for large scale production of recombinant adenoviruses. A system for use with the invention produces replication defective adenovirus. The system includes a primary cell containing a nucleic acid based on or derived from adenovirus and an isolated recombinant nucleic acid molecule for transfer into the primary cell. The isolated recombinant nucleic acid molecule is based on or derived from an adenovirus, has at least one functional encapsidation signal and at least one functional Inverted Terminal Repeat, and lacks overlapping sequences with the nucleic acid of the cell. Otherwise, the overlapping sequences would enable homologous recombination leading to replication competent adenovirus in the primary cell into which the isolated recombinant nucleic acid molecule is to be transferred.

3 Claims, 27 Drawing Sheets

U.S. PATENT DOCUMENTS

| | | |
|---|---|---|
| 5,543,328 A | 8/1996 | McClelland et al. |
| 5,545,522 A | 8/1996 | Van Gelder et al. |
| 5,547,932 A | 8/1996 | Curiel et al. |
| 5,552,311 A | 9/1996 | Sorscher et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,652,224 A | 7/1997 | Wilson et al. |
| 5,670,488 A | 9/1997 | Gregory et al. |
| 5,707,618 A * | 1/1998 | Armentano et al. ..... 424/93.21 |
| 5,712,136 A | 1/1998 | Wickham et al. |
| 5,731,190 A | 3/1998 | Wickham et al. |
| 5,753,500 A | 5/1998 | Shenk et al. |
| 5,756,086 A | 5/1998 | McClelland et al. |
| 5,770,442 A | 6/1998 | Wickham et al. |
| 5,824,544 A * | 10/1998 | Armentano et al. ..... 435/320.1 |
| 5,837,511 A | 11/1998 | Falck-Pedersen et al. |
| 5,846,782 A | 12/1998 | Wickham et al. |
| 5,849,561 A | 12/1998 | Falck-Pedersen |
| 5,851,806 A | 12/1998 | Kovesdi et al. |
| 5,856,152 A | 1/1999 | Wilson et al. |
| 5,871,727 A | 2/1999 | Curiel |
| 5,871,982 A | 2/1999 | Wilson et al. |
| 5,877,011 A | 3/1999 | Armentano et al. |
| 5,891,690 A | 4/1999 | Massie |
| 5,919,676 A | 7/1999 | Graham et al. |
| 5,922,315 A | 7/1999 | Roy |
| 5,994,106 A | 11/1999 | Kovesdi et al. |
| 5,994,128 A | 11/1999 | Fallaux et al. |
| 6,007,806 A | 12/1999 | Lathe et al. |
| 6,033,908 A | 3/2000 | Bout et al. |
| 6,040,174 A * | 3/2000 | Imler et al. ................. 435/325 |
| 6,051,430 A | 4/2000 | Plasterk et al. |
| 6,057,155 A | 5/2000 | Wickham et al. |
| 6,100,086 A | 8/2000 | Kaplan et al. |
| 6,127,525 A | 10/2000 | Crystal et al. |
| 6,140,103 A | 10/2000 | Einerhand et al. |
| 6,203,975 B1 | 3/2001 | Wilson et al. |
| 6,204,052 B1 | 3/2001 | Bout et al. |
| 6,210,939 B1 * | 4/2001 | Gregory et al. ............. 435/456 |
| 6,232,105 B1 | 5/2001 | Einerhand et al. |
| 6,238,893 B1 | 5/2001 | Hoeben et al. |
| 6,265,212 B1 | 7/2001 | Fallaux et al. |
| 6,287,857 B1 | 9/2001 | O'riordan et al. |
| 6,306,652 B1 | 10/2001 | Fallaux et al. |
| 6,340,595 B1 * | 1/2002 | Vogels et al. ................ 435/457 |
| 6,395,519 B1 * | 5/2002 | Fallaux et al. ........... 435/91.42 |
| 6,413,776 B1 * | 7/2002 | Vogels et al. ................ 435/462 |
| 6,447,768 B1 * | 9/2002 | van Zonneveld et al. .. 424/93.2 |
| 6,486,133 B1 | 11/2002 | Herlyn et al. |
| 6,492,169 B1 | 12/2002 | Vogels et al. |
| 6,602,706 B1 | 8/2003 | Fallaux et al. |
| 6,669,942 B1 | 12/2003 | Perricaudet et al. |
| 6,692,966 B1 * | 2/2004 | Fallaux et al. ............. 435/456 |
| 6,855,544 B1 * | 2/2005 | Hateboer et al. ........... 435/325 |
| 6,869,794 B1 * | 3/2005 | Vogels et al. ............... 435/325 |
| 6,878,549 B1 * | 4/2005 | Vogels et al. ............... 435/463 |
| 2002/0102732 A1 | 8/2002 | Fallaux et al. |
| 2002/0164802 A1 | 11/2002 | Fallaux et al. |
| 2002/0173039 A1 | 11/2002 | Fallaux et al. |
| 2003/0104626 A1 | 6/2003 | Fallaux et al. |
| 2004/0087027 A1 * | 5/2004 | Gregory et al. ............. 435/456 |

FOREIGN PATENT DOCUMENTS

| | | |
|---|---|---|
| CA | 2053187 | 4/1993 |
| CA | 2117668 | 9/1995 |
| EP | 117060 * | 8/1984 |
| EP | 95201611.1 | 6/1995 |
| EP | 95201728.3 | 6/1995 |
| EP | 1016726 | 12/1998 |
| EP | 1067188 | 7/1999 |
| EP | 1020529 | 11/1999 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/12649 | 6/1994 |
| WO | WO 94/15644 | 7/1994 |
| WO | WO 94/17832 | 8/1994 |
| WO | WO 94/23582 | 10/1994 |
| WO | WO 94/24297 | 10/1994 |
| WO | WO 94/24299 | 10/1994 |
| WO | WO 94/26914 | 11/1994 |
| WO | WO 94/26915 | 11/1994 |
| WO | WO 94/28152 | 12/1994 |
| WO | WO 94/28938 | 12/1994 |
| WO | WO 95/00655 | 1/1995 |
| WO | WO 95/02697 | 1/1995 |
| WO | WO 95/05201 | 2/1995 |
| WO | WO 95/06745 | 3/1995 |
| WO | WO 95/14785 | 6/1995 |
| WO | WO 95/16037 | 6/1995 |
| WO | WO 95/16772 | 6/1995 |
| WO | WO 95/21259 | 8/1995 |
| WO | WO 95/26411 | 10/1995 |
| WO | WO 95/26412 | 10/1995 |
| WO | WO 95/27071 | 10/1995 |
| WO | WO 95/31187 | 11/1995 |
| WO | WO 95/31566 | 11/1995 |
| WO | WO 95/34671 | 12/1995 |
| WO | WO 96/00790 | 1/1996 |
| WO | WO 96/07739 | 3/1996 |
| WO | WO 96/00326 | 4/1996 |
| WO | WO 96/10087 | 4/1996 |
| WO | WO 96/12030 | 4/1996 |
| WO | WO 96/13596 | 5/1996 |
| WO | WO 96/13597 | 5/1996 |
| WO | WO 96/13598 | 5/1996 |
| WO | WO 96/14061 | 5/1996 |
| WO | WO 96/14837 | 5/1996 |
| WO | WO 96/16676 | 6/1996 |
| WO | WO 96/17073 | 6/1996 |
| WO | WO 96/18418 | 6/1996 |
| WO | WO 96/18740 | 6/1996 |
| WO | WO 96/24453 | 8/1996 |
| WO | WO 96/26281 | 8/1996 |
| WO | WO 96/33280 | 10/1996 |
| WO | WO 96/35798 | 11/1996 |
| WO | WO 96/40955 | 12/1996 |
| WO | WO 97/00326 | 1/1997 |
| WO | WO 97/00947 | 1/1997 |
| WO | WO 97/04119 | 2/1997 |
| WO | WO 97/05255 | 2/1997 |
| WO | WO 97/12986 | 4/1997 |
| WO | WO 97/20575 | 6/1997 |
| WO | WO 97/38723 | 10/1997 |
| WO | WO 98/07865 | 2/1998 |
| WO | WO 98/11221 | 3/1998 |
| WO | WO 98/13499 | 4/1998 |
| WO | WO 98/22609 | 5/1998 |
| WO | WO 98/32842 | 7/1998 |
| WO | WO 98/40509 | 9/1998 |
| WO | WO 98/49300 | 11/1998 |
| WO | WO 98/50053 A1 | 11/1998 |
| WO | WO 99/32647 | 7/1999 |

| WO | WO 99/47180 A1 | 9/1999 |
| --- | --- | --- |
| WO | WO 99/55132 | 11/1999 |
| WO | WO 99/58646 | 11/1999 |
| WO | WO 00/03029 | 1/2000 |
| WO | WO 00/24730 A2 | 5/2000 |
| WO | WO 00/31285 | 6/2000 |
| WO | WO 00/52186 | 9/2000 |
| WO | WO 00/70071 A1 | 11/2000 |
| WO | WO 01/04334 | 1/2001 |
| WO | WO 01/90158 A1 | 11/2001 |
| WO | WO 02/24730 | 3/2002 |
| WO | WO 0227006 A1 | 4/2002 |

OTHER PUBLICATIONS

Amalfitano et al., "Improved adenovirus packaging cell lines to support the growth of replication-defective gene-delivery vectors", *Proc. Natl. Acad. Sci. USA*, 93:3352-3356, Apr. 1996.

Amalfitano et al., "Isolation and characterization of packaging cell lines that coexpress the adenovirus E1, DNA polymerase, and preterminal proteins: implications for gene therapy", *Gene Therapy*, 4:258-263, 1997.

Armentano et al., "Characterization of an Adenovirus Gene Transfer Vector Containing an E4 Deletion", *Human Gene Therapy*, 6:1343-1353, Oct. 1995.

Bernards, Rene, et al., "Characterization of Cells Transformed by Ad5/Ad12 Hybrid Early Region I Plasmids", *Virology*, 120:422-432, 1982.

Bernards, Rene, et al., "Role of Adenovirus Types 5 and 12 Early Region 1b Tumor Antigens in Oncogenic Transformation", *Virology*, 127:45-53, 1983.

Brough et al., "A Gene Transfer Vector-Cell Line System for Complete Functional Complementation of Adenovirus Early Regions E1 and E4", *Journal of Virology*, 70(9):6497-6501, Sep. 1996.

Brough et al., "Construction, Characterization, and Utilization of Cell Lines Which Inducibly Express the Adenovirus DNA-Binding Protein", *Virology*, 190:624-634, 1992.

Brough et al., "Multiple Functions of the Adenovirus DNA-Binding Protein Are Required for Efficient Viral DNA Synthesis", *Virology*, 196:269-281, 1993.

Broough et al., "Restricted changes in the adenovirus DNA-binding protein that lead to extended host range or temperature sensitive phenotypes", *Journal of Virology*, vol. 55, pp. 206-212, 1985.

Caravokyri et al., "Constitutive Episomal Expression of Polypeptide IX (pIX) in a 293-Based Cell Line Complements the Deficiency of pIX Mutant Adenovirus Type 5", *Journal of Virology*, 69(11):6627-6633, Nov. 1995.

Engelhardt et al., "Ablation of E2A in recombinant adenoviruses improves transgene persistence and decreases inflammatory response in mouse liver", *Proceeding of the National Sciences of USA*, vol. 91, pp. 6196-6200, 1994.

Fallaux et al., "Characterization of 911: A New Helper Cell Line for the Titration and Propagation of Early Region 1-Deleted Adnoviral Vectors", *Human Gene Therapy*, 7:215-222, 1996.

Fields et al., "Fields Virology", Second Edition, pp. 28-30, 1987.

Fisher et al., "Recombinant Adenovirus Deleted of All Viral Genes for Gene Therapy of Cystic Fibrosis", *Virology*, 217:11-22, 1996.

Gao et al., "Biology of Adenovirus Vectors with E1 and E4 Deletions for Liver-Directed Gene Therapy", *Journal of Virology*, 70(12):8934-8943, Dec. 1996.

Gorziglia et al., "Elimination of both E1 and E2a from Adenovirus Vectors Further Improves Prospects for Vivo Human Gene Therapy", *Journal of Virology*, 70(6):4173-4178, Jun. 1996.

Graham, F.L. et al., "Characteristics of a Human Cell Line Transformed by DNA from Human Adenovirus Type 5", *J. gen. Virol.*, 36:59-74, 1977.

Grodzicker, Terri, et al., "Expression of Unselected Adenovirus Genes in Human Cells Co-transformed with the HSV-1 tk Gene and Adenovirus 2 DNA", *Cell*, 21:453-463, Sep. 1980.

Hardy et al., "Construction of Adenovirus Vectors through Cre-lox Recombination", *Journal of Virology*, 71(3):1842-1849, Mar. 1997.

Hehir et al., "Molecular Characterizatioin of Replication-Competent Variants of Adenovirus Vectors and Genome Modifications To Prevent Their Occurrence", *Journal of Virology*, 70(12):8459-8467, Dec. 1996.

Imler et al., "Novel complementation cell lines drived from human lung carcinoma A549 cells support the growth of E1-deleted adenovirus vectors", *Gene Therapy*, 3:75-84, 1996.

Kornberg, Arthur, "DNA Replication", W.H. Freeman and Company, San Francisco, pp. 35, 153.

Krougliak et al., "Development of Cell Lines Capable of Complementing E1, E4, and Protein IX Defective Adenovirus Type 5 Mutants", *Human Gene Therapy*, 6:1575-1586, Dec. 1995.

Lemarchand et al., "Adenovirus-mediated transfer of a recombinant human α1-antitrypsin cDNA to human endothelial cells", *Proc. Natl. Acad. Sci. USA*, vol. 89, pp. 6482-6486, Jul. 1992.

Lieber et al., "Recombinant Adenoviruses with Large Deletions Generated by Cre-Mediated Excision Exhibit Different Biological Properties Compared with First-Generation Vectors In Vitro and In Vivo", *Journal of Virology*, 70:8944-8960, Dec. 1996.

Lochmuller, H., et al., "Emergence of Early Region 1-Containing Replication-Competent Adenovirus in Stock of Replication-Defective Adenovirus Recombinants (ΔE1+ΔE3) During Multiple Passages in 293 Cells", *Human Gene Therapy*, 5:1485-1491, Dec. 1994.

Louis, Nathalie, et al., "Cloning and Sequencing of the Cellular-Viral Junctions from the Human Adenovirus Type 5 Transformed 293 Cell Line", *Virology*, 233:423-429, 1997.

Ngo et al., "in The Protein Folding Problem and Tertiary Structure Prediction", Merz et al., (ed.), Birkhauser, Boston, MA, pp. 433 and 492-495, 1994.

Orkin et al., "Reports and Recommendations of the Panel to Assess the NIH Investment in Research on Gene Therapy", 21 pages, Dec. 7, 1995.

Roberts, Bryan E., et al., "Individual Adenovirus Type 5 Early Region 1A Gene Products Elicit Distinct Alterations of Cellular Morphology and Gene Expression", *Journal of Virology*, pp. 404-413, Nov. 1985.

Rosenfeld et al., "In Vivo Transfer of the Human Cystic Fibrosis Transmembrane Conductance Regulator Gene to the Airway Epithelium", *Cell*, vol. 68, pp. 143-155, Jan. 10, 1992.

Schaack et al., "Adenovirus Type 5 Precursor Terminal Protein-Expressing 293 and HeLa Cell Lines", *Journal of Virology*, 69(7):4079-4085, Jul. 1995.

Stratford-Perricaudet, Leslie, et al., "Gene Transfer Into Animals: The Promise of Adenovirus, Human Gene Transfer", 219:51-61, 1991.

Trapnell et al., "Gene therapy using adenoviral vectors", *Current Opinion in Biotechnology*, 5:617-625, 1994.

Vaessen, R.T.M.J., "Adenovirus E1A-Mediated Regulation of Class 1 MHC Expression", *The EMBO Journal*, 5(2):335-341, 1986.

Vaessen, R.T.M.J., "Different Adenovirus E1A-Controlled Properties of Transformed Cells Require Different Levels of E1A Expression", *Gene*, pp. 247-254, 1987.

Vamjaesebrpecl. Bart. et el., "Modulation of Cellular Susceptibility to the Cytotoxic/Cytostatic Action of Tumor Necrosis Factor by Adenovirus E1 Gene Expression Is Cell Type-Dependent", *Virology*, 176:362-368, 1990.

Vox et al., "Characterization of Adenovirus Type 5 Insertion and Deletion Mutants Encoding Altered DNA Binding Proteins", *Virology*, 172, pp. 634-642, 1989.

Wang et al., "A packaging cell line for propagation of recombinant adenovirus vectors containing two lethal gene-region deletions", *Gene Therapy*, 2:775-783, 1995.

Weinberg et al., "A cell line that supports the growth of a defective early region 4 deletion mutant of human adenovirus type 2", *Proc. Natl. Sci. USA*, vol. 80, pp. 5383-5386, Sep. 1983.

Yang et al., "Cellular immunity to viral antigens limits E1-deleted adenovirus for gene therapy", *Proc. Natl. Acad. Sci. USA*, vol. 91, pp. 4407-411, May 1994.

Yeh et al., "Efficient Dual Transcomplementation of Adenovirus E1 and E4 Regions from a 293-Dervied Cell Line Expressing a Minimal E4 Functional Unit", *Journal of Virologly*, 70(1);559-565, Jan. 1996.

Zhou et al., "Development of a Complementing Cell Line and a System for Construction of Adenovirus Vectors with E1 and E2a Deleted", *Journal of Virology*, 70(1):7030-7038, Oct. 1996.

Acsadi et al., Adenovirus-mediated gene transfer into striated muscles, J Mol Med, 1995, pp. 165-180, vol. 73.

Berg et al., High-Level Expression of Secreted Proteins from Cells Adapted to Serum-Free Suspension Culture, Bio Techniques, 1993, pp. 972-978, vol. 14, No. 6.

Colby et al., Adenovirus Type 5 Virions Can Be Assembled In Vivo in the Absence of Detectable Polypeptide IX, Journal of Virology, Sep. 1981, pp. 997-980, vol. 39, No. 3

Gallimore et al., Transformation of Human Embryo Retinoblasts with Simian Virus 40, Adenovirus and ras Oncogenes, Anticancer Research, 1986, pp. 499-508, vol. 6.

GenBank Accession No. X02996.1, 1993, "Adenovirus type 5 left 32% of the genome."

Graham et al., Size and location of the transforming region in human adenovirus type, 5 DNA, Nature, Oct. 25, 1974, pp. 687-691, vol. 251.

Hitt et al., Construction and Propagation of Human Adenovirus Vectors, Cell Biology, 1994, pp. 479-490, vol. 1, Academic Pess, San Diego, California.

Marck, Christian, 'DNA Strider': a 'C' program for the fast analysis of DNA and portein sequences on the Apple Macintosh family of computers, Nucleic Acids Research, 1988, pp. 1829-1836, vol. 16, No. 5.

Mitani et al., Rescue, propagation, and partial purification of a helper virus-dependent adenovirus vector, Proc. Natl. Acad. Sci., Apr. 1995, pp. 3854-3858, vol. 92.

NCBI database excerpt: Locus AC_000008 (human adenovirus type 5).

Notice of Opposition to a European Patent by Serono International S.A. filed against Patent No. 0 833 934 (Jul. 5, 2005).

Opposition lodged by Cevec Pharmaceuticals GmbH against European Patent 0 833 934 (Jul. 5, 2005).

Abrahamsen et al., "Construction of an Adenovirus Type 7a E1A Vector," Journal of Virology Nov. 1997, p. 8946-8951 vol. 71, No. 11.

Albiges-Rizo et al., "Human Adenovirus Serotype 3 Fiber Protein," Journal of Biological Chemistry, 266(6), 3961-3967 (1991).

Anderson, Nature, "Human gene therapy," Apr. 1998, vol. 392, pp. 25-30.

Athappilly et al., "The Refined Crystal Structure of Hexon, the Major Coat Protein of Adenovirus Type 2, at 9 A Resolution," J. Mol. Biol. (1994) 242, 430-455.

Bai et al., "Mutations That Alter an Arg-Gly-Asp (RGD) Sequence in the Adenovirus Type 2 PentonBase Protein Abolish Its Cell-Rounding Activity and Delay Virus Reproductions in Flat Cells," Journal of Virology, 67(9), 5198-5205 (1993).

Bailey et al., "Phylogenetic Relationships among Adenovirus Serotypes," Virology, 205, 439-452 (1994).

Ball-Goodrich et al., "Parvoviral Target Cell Specificity: Acquisition of Firbotropism by a Mutant of the Lymphotropic Strain of Minute Virus of Mice Involves Multiple Amino Acid Subitutions within the Capsid," Virology, 184, 175-186 (1991), abstract only.

Basler et al., Sequence of the immunoregulatory early region 3 and flanking sequences of adenovirus type 35, 1996, Gene 170:249-254.

Basler et al., "Subgroup B Adenovirus Type 35 Early Region 3 mRNAs Differ from Those of the Subgroup C Advenoviruses," Virology 215, 165-177 (1996).

Batra et al., "Receptor-mediated gene delivery employing lectin-binding specificity," Gene Therapy, 1, 255-260 (1994).

Berendsen, Herman J. C., A Glimpse of the Holy Grail, Science, 1998, vol. 282, pp. 642-643.

Boursnell et al., "In vitro construction of a recombinant adenovirus Ad2:Ad5," Gene, 13, 311-317 (1981).

Bridge et al., "Adenovirus Early Region 4 and Viral DNA Synthesis," Virology 193, 794-801 (1993).

Brody et al., "Adenovirus-Mediated in Vivo Gene Transfer," Annals New York Academy of Sciences pp. 90-101.

Caillet-Boudin et al., "Functional and Structural Effects of an Ala to Val Mutation in the Adenovirus Serotype2 Fibre," J. Mol. Biol., 217, 477-486 (1991).

Chiu et al., Folding & Design, "Optimizing energy potentials for success in protein tertiary structure prediction," May 1998, 3:223-228.

Chroboczek et al., Adenovirus Fiber, Current Topics in Microbiology and Immunology 1995;199 (pt 1) pp. 163-200.

Chu et al., "Cell targeting with retroviral vector particles containing antibodyenvelope fusion proteins," Gene Therapy, 1, 292-299 (1994), abstract only.

Cotten et al., "Transferrin-polycation-mediated introduction of DNA into human leukemic cells: Stimulation by agents that affects the survival of transfected DNA or modulate transferrin receptor levels," Proc. Natl. Acad. Sci. USA, 87, 4033-4037 (1990).

Cotten et al., "High-efficiency receptor-mediated delivery of small and large (48 kilobase gene constructs using the endosome-disruption activity of defective or chemically inactivated adenovirus particles," Proc. Natl. Acad. Sci. USA, 89, 6094-6098 (1992).

Crawford-Miksza et al., "Analysis of 15 Adenovirus Hexon Proteins Reveals the location and Structure of Seven Hypervariable Regions Containing SerotypeSpecific Residues," Journal of Virology, Mar. 1996, p. 1836-1844.

Cromptoon et al., "Expression of a foreign epitope on the surface of the adenovirus hexon," J. Gen Virol, 75(1), 133-139 (1994).

Crystal, Ronald G., "Transfer of Genes to Humans: Early Lessons and Obstacles to Success," Science, 270, 404-410 (1995).

Curiel et al., "High-Efficiency Gene Transfer Mediated by Adenovirus Coupled to DNAPolylysine Complexes," Human Gene Therapy, 3, 147-154 (1992), abstract only.

Curiel et al., "Adenovirus enhancement oftransferring-polylysine-mediated gene delivery," Proc. Natl. Acad. Sci. USA, 88, 8850-8854 (1991).

De Jong et al., "Adenovirus Isolates From Urine of Patients with Acquired Immunodeficiency Syndrome," The Lancet, Jun. 11, 1983 pp. 1293-1296.

De Jong et al., Adenoviruses from Human Immunodeficiency Virusinfected Individuals, Including Two Strains That Represent New Candiate Serotypes Ad50 and Ad51 of Species B1 and D, Respectively, Journal of Clinical Microbiology, Dec. 1999, p. 3940-45, vol. 37, No. 12, American Society for Microbiology.

Defer et al., "Human Adenovirus-Host Cell Interactions: Comparative Study with Members of Subgroups B and C," Journal of Virology, 64(8), 3661-3673 (1990).

Deonarain, "Ligand-targeted receptor-mediated vectors for gene delivery," (1998) Expert Opin. Ther. Pat. 8: 53-69.

Dijkema et al., "Transformation of Primary Rat Kidney Cells by DNA Fragments of Weakly Oncogenic Adenoviruses," Journal of Virology, Dec. 1979, p. 943-950.

Douglas J T et al.: "Strategies to accomplish targeted gene delivery to muscle cells employing tropismmodified adenoviral vectors" Neuromusclar Disorders, Pergamon Press, GB, vol. 7, Jul. 1997, pp. 284-298, XP002079944 ISSN: 0960-8966, abstract only.

Dupuit et al., " Regenerating Cells in Human Airway Surface Epithelium Represent Preferential Targets for Recombinant Adenovirus," Human Gene Therapy, 6, 1185-1193 (1995), abstract only.

Eck et al., "Gene-Based Therapy," (1996) Goodman & Gillman's The Pharmacological Basis of Therapeutics, McGraw-Hill, New York, N.Y., pp. 77-101.

Etienne-Julan et al., "The efficiency of cell targeting by recombinant retroviruses depends on th nature of the receptor and the composition of the artificial cellvirus linker," Journal of General Virology, 73, 3251-3255 (1992), abstract only.

Falgout et al., "Characterization of Adenovirus Particles Mde by Deletion Mutants Lacking the Fiber Gene," Journal 6 Virology, 62(2), 622-625 (1988).

Flomenbert et al., "Molecular Epidemiology of Adenovirus Type 35 Infections in Immunocompromised Hosts," The Journal Of Infectious Diseases vol. 155, No. 6, Jun. 1987, p. 1127-1134.

Francki et al., "Classification and Nomenclature of Viruses," Fifth Report of the International Committee on Taxonomy of Viruses; Virology Division of the International Union of Microbiology Societies pp. 140-143.

Gall et al., "Construction and characterization of Hexon-Chimeric Adenoviruses: Specification of adenovirus serotype," 72(12) Journal of Virology 10260-64 (1998).

Gall et al., "Adenovirus Type 5 and 7 Capsid Chimera: Fiber Replacement Alters Receptor Tropism without Affecting Primary Immune Neutralization Epitopes," Journal Of Virology, Apr. 1996, p. 2116-2123.

George et al., "Gene therapy progress and prospects: adenoviral vectors," Gene Therapy (2003) 10, 1135-1141.

Gorecki, "Prospects and problems of gene therapy: an update," (2001) Expert Opin. Emerging Drugs 6(2): 187-98.

Greber et al., "Stepwise Dismantling of Adenovirus 2 during Entry into Cells," Cell, 75, 477-486 (1993), abstract only.

Green et al., "Evidence for a repeating cross: sheet structure in the adenovirus fibre," EMBO Journal, 2(8), 1357-1365 (1983).

Grubb et al., Inefficient gene transfer by adenovirus vector to cystic fibrosis airway epithelia of mice and humans, Nature, 371, 802-806 (1994), abstract only.

Gurunathan et al., American Association of Immunologists, "CD40 Ligand/Trimer DNA Enhances Both Humoral and Cellular Immune Responses and Indicates Protective Immunity to Infectious and Tumor Challenge," 1998, 161:4563-4571, abstract only.

Han et al., "Ligand-directed retroviral targeting of human breast cancer cells," Proc. Natl. Acad. Sci. USA, 92, 9747-9751 (1995).

He et al., "A simplified system for generating recombinant adenovirus," Proc. Natl. Acad. Sci. USA vol. 95 pp. 2509-2514, Mar. 1998.

Henry et al., "Characterization of the Knob Domain of the Adenovirus Type 5 Fiber Protein Expressed in *Escherichia coli*," Journal of Virology, 68(8), 5239-5246 (1994).

Hidaka, Chisa, et al., "CAR-dependent and CAR-independent pathways of adenovirus vector-mediated gene transfer and expression in human fibroblasts," 103(4)The Journal of Clinical Investigation 579-87 (Feb. 1999).

Hierholzer et al., "Adenoviruses from Patients with AIDS: A Plethora of Serotypes and A Description of Five New Serotypes of Subgenus D (Types 43-47)," The Journal Of Infectious Diseases vol. 158, No. 4 Oct. 1988, 804-813.

Hong et al., "The Amino Terminus of the Adenovirus Fiber Protein Encodes the Nuclear Localization Signal," Virology 185(2), 758-767 (1991).

Horvath et al., "Nonpermissivity of Human Peripheral Blood Lymphocytes to Adenovirus Type 2 Infection," Journal of Virology, 62(1), 341-345 (1988).

Huang et al., "Upregulation of Intergrins y3 and yt on Human Monocytes and TLymphocytes Facilitates Adenovirus Mediated Gene Delivery," Journal of Virology, 69(4), 2257-2263 (1995).

Jolly; viral vector systems for gene therapy, 1994, Cancer Gene Therapy, vol. 1, No. 1: 51-64.

Kang et al., "Molecular Cloning And Physical Mapping Of The Dna Of Human Adenovirus Type 35," Acta Microbiologica Hungarica 36(1), pp. 67-75 (1989).

Kang et al., "Relationship Of E1 and E3 Regions Of Human Adenovirus 35 To Those Of Human Adenovirus Subgroups A, C and D," Acta Microbiologica Hungarica 36 (4), pp. 445-457 (1989).

Karayan et al., "Oligomerization of Recombinant Penton Base of Adenovirus Type 2 and Its Assembly with Fiber in Baculovirus-Infected Cells," Virology, 202, 782-795 (1994).

Kass-Eisler et al., "Quantitative determination of adenovirusmediated gene delivery to rat cardiac myocytes*in vitro* and *in vivo*," Proc. Natl. Acad. Sci. USA, 90, 11498-11502 (1993).

Kmiec, "Gene Therapy," American Scientist, vol. 87, pp. 240-247, May-Jun. 1999.

Komoriya et al., The Minimal Essential Sequence for a Major Cell Typespecific Adhesion Site (CS1) within the Alternatively Spliced Type III Connecting Segment Domain of Fibronectin Is LeucineAspartic Acid-Valine,: Journal of Biological Chemistry, 266(23), 15075-15079 (1991).

Krasnykh et al.: "Generation Of Recombinant Adenovirus Vectors With Modified Fibers For Altering Viral Tropism" Journal Of Virology, The American Society For Microbiology, US, vol. 70, No. 10, Oct. 1, 1996, pp. 6839-6846, XP002067518 ISSN: 0022-538x.

Lattanzi, Laura, et al., "High Efficiency Myogenic Conversion of Human Fibroblasts by Adenoviral Vectormediated *MyoD* Gene Transfer," 101(10) J. Clin. Invest. 2119-28 (May 1998).

Lee et al., "The constitutive expression of the immunomodulatory gp 19k protein in E1, E3 adenoviral vectors strongly reduces the host cytotoxic T cell response against the vector," Gene Therapy (1995) 2, 256-262.

Levrero et al., "Defective and nondefective adenovirus vectors for expressing foreign gnes in vitro and invivo," Gene, 101 (1991) 195-202.

Li et al., "Genetic Relationship between Thirteen Genome Types of Adenovirus 11,34, and 35 with Different Tropisms," Intervirology 1991;32:338-350.

Liu et al., Molecular Basis of the inflammatory response to adenovirus vectors. Gene Therapy (2003 10, 93540.

Maraveyas et al., "Targeted Immunotherapy B An update with special emphasis on ovarian cancer," Acta Oncologica, 32(7/8), 741-746 (1993), abstract only.

Mastrangeli et al., "Sero-Switch" Adenovirus-Mediated *In Vivo* Gene Transfer: Circumvention of Anti-Adenovirus Humoral Immune Defenses Against Repeat Adenovirus Vector Administration by Chaning the Adenovirus Serotype, Human Gene Therapy, 7, 79-87 (1996).

Mathias et al., "Multiple Adenovirus Serotypes Use v Integrins for Infection," Journal of Virology, 68(10), 6811-6814 (1994).

Mautner et al., "Recombination in Adenovirus: DNA Sequence Analysis of Crossover Sites in Intertypic Recominants," Virology, 131, 1-10 (1983).

Mautner et al., "Recombination in Adenovirus: Analysis of Crossover Sites in Intertypic Overlap Recombinants," Virology, 139, 43-52, (1984).

Merriam-Webster Dictionary (on line) retrieved from the internet<URL:htpp://www.mw.com/cgi-bin/dictionary, "derive," 2002.

Michael et al., "Addition of a short peptide ligand to the adenovirus fiber protein," Gene Therapy, 2, 660-668 (1995)/

Michael et al., "Binding-incompetent Adenovirus Facilitates Molecular Conjugatemediated Gene Transfer by the Receptor-mediated Endocytosis Pathway," Journal of Biological Chemistry, 268(10), 6866-6869 (1993).

Miller et al., "Targeted vectors for gene therapy," FASEB Journal, 9, 190-199 (1995).

Neda et al., "Chemical Modification of an Ecotropic Murine Leukemia Virus Results in Redirection of Its Target Cell Specificity," Journal of Biological Chemistry, 266(22), 14143-14146 (1991).

Nemerow et al., "The Role of αv Integrins in Adenovirus Infection," Biology of Vitronectins and their Receptors, 177-184 (1993).

Nemerow et al., "Adenovirus entry into host cells: a role forα integrins," Trends In Cell Biology, 4, 52-55 (1994).

Novelli et al., "Deletion Analysis of Functional Domains inBaculovirus-Expressed Adenovirus Type 2 Fiber," Virology, 185, 365-376 (1991).

Peteranderl et al., "Trimerization of the Heat Shock Transcription Factor by a TripleStranded-Helical Coiled-Coil," Biochemistry, 31, 12272-12276 (1992), abstract only.

Prince, "Gene Transfer: A Review Of Methods And Applications," Pathology (1998), 30, pp. 335-347.

Pring-Akerblom et al., "Sequence Characterization and Comparison of Human Adenovirus Subgenus B and E Hexons," Virology, 212, 232-36 (1995).

Ragot et al., "Effecient Adenovirus-mediated transfer of a human minidystrophin gene to skeletal muscle of mdx mice" Nature, Macmillan Journals Ltd. London, GB, vol. 361, No. 6413, 1993, pp. 647-650, XP002162515 ISSN: 0028-0836, abstract only.

Rea et al., "Highly efficient transduction of human monocyto-derived dendritic cells with subgroup B fibermodified adenovirus vectors enhances transgeno-encoded antigen presentation to cytotoxic T cells." Journal Of Immunology, (Apr. 15, 2000) 166 (8) 5236-44., Apr. 15, 2001 XP002192775.

Robbins et al., "Viral Vectors for Gene Therapy," Pharmacol. Ther. vol. 80, No. 1, pp. 35-47, 1998.

Roberts et al., "Three-Dimensional Structure of the Adenovirus Major Coat Protein Hexon," Science, 232, 114851 (1986).

Roelvink et al., The Coxsackievirus-Adenovirus Receptor Protein Can Function as a Cellular Attachment Proteinfor Adenovirus Serotypes from Subgroups A, C, D, E, and F. Journal Of Virology, Oct. 1998, p. 7909-7915, vol. 72, No. 10.

Romano, "Gene Transfer in Experimental Medicine," Drug & News Perspectives, vol. 16, No. 5, 2003, 13 pages.

Russell et al., "Retroviral vectors displaying functional antibody fragments," Nucleic Acids Research, 21(5), 1081-1085 (1993).

Russell, "Replicating Vectors for Gene Therapy of Cancer: Risks, Limitations and Prospects," European Journal of Cancer, vol. 30A, No. 8, pp. 1165.

Sabourin et al., "The molecular regulation of myogenesis," (2000) Clin. Genet. 57(1): 16-25.

Schnurr et al., "Two New Candidate Adenovirus Serotypes," Intervirology 1993;36:79-83.

Schulick et al., "Established Immunity Precludes Adenovirusmediated Gene Transfer in Rat Carotid Arteries," The Journal of Clinical Investigation vol. 99, No. 2, Jan. 1997, 209219.

Segerman et al., "Adenovirus types 11p and 35p show high binding efficiencies for committed hematopoietic cell lines and are infective to these cell lines" Journal of Virology, The American Society for Microbiology, US, vol. 74, No. 3, Feb. 2000(200-02), pp. 1457-1467, XP002161682 ISSN: 0022-538X.

Shayakhmetov et al., "Efficient Gene Transfer into Human CD34 Cells by a Retargeted Adenovirus Vector," Journal Of Virology, Mar. 2000, p. 2567-2583.

Signàas et al., "Adenovirus 3 Fiber Polypeptide Gene: Implications for the Structure of the Fiber Protein," Journal of Virology, 53(2), 672-678 (1985).

Silver et al., "Interaction of Human Adenovirus Serotype 2 with Human Lymphoid Cells," Virology, 165, 377-387 (1988).

Stevenson et al.; Selective Targeting of Human Cells by a Chimeric Adenovirus Vector Containing a Modified Fiber Protein, 1997, Journal of Virology, vol. 71: 4782-4790.

Stewart et al., "Difference imaging of adenovirus: bridging the resolution gap between X-ray crystallography and electron microscopy," EMBO Journal, 12(7), 2589-2599 (1993).

Stratford-Perricaudet LD et al.: "Widespread Long-Term Gene Transfer To Mouse Skeletal Muscles And Heart" Journal Of Clinical Investigation, New York, NY, US, vol. 90 No. 2, Aug. 1992 (199208), ISSN: 0021-9738.

Toogood et al., "The Adenovirus Type 40 Hexon: Sequence Predicated Structure and Relationship to Other Adenovirus Hexons," J. gen. Virol (1989), 70, 3203-3214.

Valderrama-Leon et al., "Restriction Endonuclease Mapping of Adenovirus 35, a Type Isolated from Immunocompromised Hosts," Journal Of Virology, Nov. 1985, p. 647-650.

Verma et al., Nature, "Gene therapy-promises, problems and prospects," Sep. 1997, vol. 389, pp. 239-242.

Wadell, "Molecular Epidemiology of Human Adenoviruses," Microbiology and Immunoogy, vol. 110 pp. 191-220.

Wagner et al., "Coupling of adenovirus to transferring-polylysine/DNA complexes greatly enhances receptor-mediated gene delivery and expression of transfected genes," Proc. Natl. Acad. Sci. USA, 89, 6099-6103 (1992).

Watson et al., "An Antigenic Analysis of the Adenovirus Type 2 Fibre Polypeptide," Journal of Virology, 69, 525-535 (1988).

Wickham et al., "Integrins $_{v3}$ and $_{v5}$ Promote Adenovirus Internalization but Not Virus Attachment,"Cell, 73, 309319 (1993).

Wickham et al., "Integrin $_{v5}$ Selectively Promotes Adenovirus Mediated Cell Membrane Permeabilization," Journal of Cell Biology, 127(1), 257-264 (1994).

Wickham et al,: "Increased In Vitro and In Vivo Gene Transfer by Adenovirus Vectors Containing Chimeric Fiber Proteins," Journal of Virology, Nov. 1997, p. 8221-8229.

Zhong et al.: "Recombinant Adenovirus Is An Efficient And Non-Pertubing Genetic Vector For Human Dendritic Cells" European Journal Of Immunology, Weinheim, DE, vol. 29, No. 3, 1999, pp. 964972, XP000938797 ISSN:0014-2980.

Brough et al, Abstract Book CSH Conference On Gene Therapy (1996) 42.

Sabatie et al, Abstract Book 14th Meeting on Animal Cell Technology (1996) BI-3.

* cited by examiner

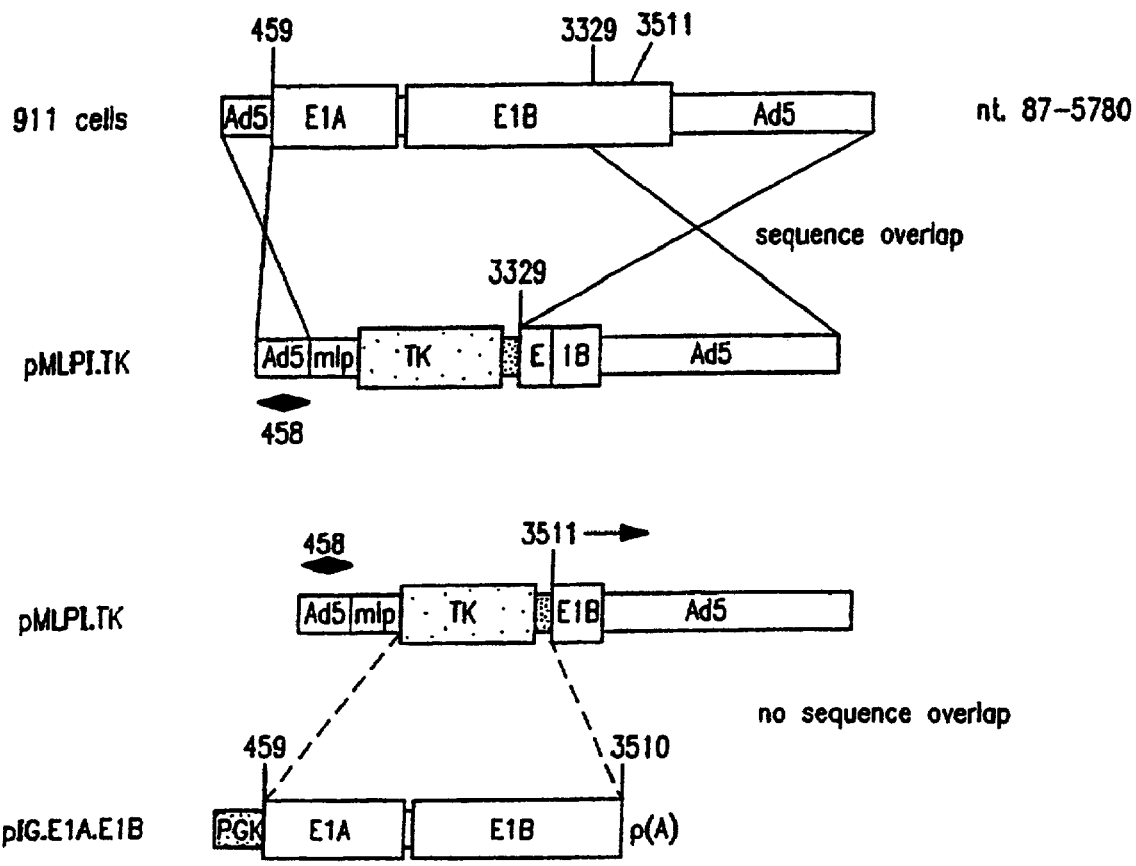
FIG. IIA
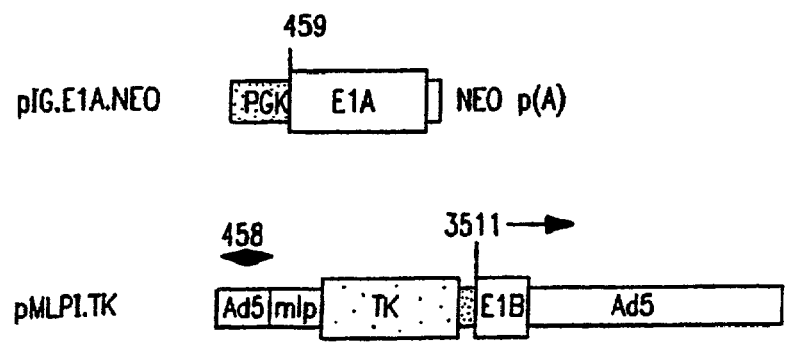
FIG. IIB

```
5'-GTACACTGACCTAGTGCCGCCCGGGCA
   |||||||||||||||||||| A
    GATCACGGCGGGCCCGA
```

FIG.15

```
CATCATCAAT AATATACCTT ATTTTGGATT GAAGCCAATA TGATAATGAG GGGGTGGAGT      60
TTGTGACGTG GCGCGGGGCG TGGGAACGGG GCGGGTGACG TAGTAGTGTG GCGGAAGTGT     120
GATGTTGCAA GTGTGGCGGA ACACATGTAA GCGACGGATG TGGCAAAAGT GACGTTTTTG     180
GTGTGCGCCG GTGTACACAG GAAGTGACAA TTTTCGCGCG GTTTTAGGCG GATGTTGTAG     240
TAAATTTGGG CGTAACCGAG TAAGATTTGG CCATTTTCGC GGGAAAACTG AATAAGAGGA     300
AGTGAAATCT GAATAATTTT GTGTTACTCA TAGCGCGTAA TATTTGTCTA GGGCCGCGGG     360
GACTTTGACC GTTTACGTGG AGACTCGCCC AGTGTTTTT CTCAGGTGTT TTCCGCGTTC      420
CGGGTCAAAG TTGGCGTTTT ATTATTATAG TCAGGGGCTG CAGGTCGTTA CATAACTTAC     480
GGTAAATGGC CCGCCTGGCT GACCGCCCAA CGACCCCCGC CCATTGACGT CAATAATGAC     540
GTATGTTCCC ATAGTAACGC CAATAGGGAC TTTCCATTGA CGTCAATGGG TGGAGTATTT     600
ACGGTAAACT GCCCACTTGG CAGTACATCA AGTGTATCAT ATGCCAAGTA CGCCCCCTAT     660
TGACGTCAAT GACGGTAAAT GGCCCGCCTG GCATTATGCC CAGTACATGA CCTTATGGGA     720
CTTTCCTACT TGGCAGTACA TCTACGTATT AGTCATCGCT ATTACCATGG TGATGCGGTT     780
TTGGCAGTAC ATCAATGGGC GTGGATAGCG GTTTGACTCA CGGGGATTTC CAAGTCTCCA     840
CCCCATTGAC GTCAATGGGA GTTTGTTTTG GCACCAAAAT CAACGGGACT TTCCAAAATG     900
TCGTAACAAC TCCGCCCCAT TGACGCAAAT GGGCGGTAGG CGTGTACGGT GGGAGGTCTA     960
TATAAGCAGA GCTCGTTTAG TGAACCGTCA GATCGCCTGG AGACGCCATC CACGCTGTTT    1020
```

FIG. 20A

```
TGACCTCCAT AGAAGACACC GGGACCGATC CAGCCTCCGG ACTCTAGAGG ATCCGGTACT 1080
CGAGGAACTG AAAAACCAGA AAGTTAACTG GTAAGTTTAG TCTTTTTGTC TTTTATTTCA 1140
GGTCCCGGAT CCGGTGGTGG TGCAAATCAA AGAACTGCTC CTCAGTGGAT GTTGCCTTTA 1200
CTTCTAGTAT CAAGCTTGAA ACATTTCGCA TTCCTTTGTG TTACATTCTT GAATGTCGCT CGCAGTGACA 1260
TTAGCATTCC GGTACTGTTG GTAAAATGGA AGACGCCAAA AACATAAAGA AAGGCCCGGC 1320
GCCATTCTAT CCTCTAGAGG ATGGAACCGC TGGAGAGCAA CTGCATAAGG CTATGAAGAA 1380
ATACGCCCTG GTTCCTGGAA CAATTGCTTT TACAGATGCA CATATCGAGG TGAACATCAC 1440
GTACGCGGAA TACTTCGAAA TGTCCGTTCG GTTGGCAGAA GCTATGAAAC GATATGGGCT 1500
GAATACAAAT CACAGAATCG TCGTATGCAG TGAAAACTCT CTTCAATTCT TTATGCCGGT 1560
GTTGGGCGCG TTATTATCG GAGTTGCAGT TGCGCCCGCG AACGACATTT ATAATGAACG 1620
TGAATTGCTC AACAGTATGA ACATTTCGCA GCCTACCGTA GTGTTTGTTT CCAAAAGGG 1680
GTTGCAAAAA ATTTTGAACG TGCAAAAAAA TTGCAAGAAA ATCCAGAAAA TTATTATCAT 1740
GGATTCTAAA ACGGATTACC AGGGATTTCA GTCGATGTAC ACGTTCGTCA CATCTCATCT 1800
ACCTCCCGGT TTTAATGAAT ACGATTTTGT ACCAGAGTCC TTTGATCGTG ACAAAACAAT 1860
TGCACTGATA ATGAATTCCT CTGGATCTAC TGGGTTACCT AAGGGTGTGG CCCTTCCGCA 1920
TAGAACTGCC TGCGTCAGAT TCTCGCATGC CAGAGATCCT ATTTTTGGCA ATCAAATCAT 1980
TCCGGATACT GCGATTTTAA GTGTTGTTCC ATTCCATCAC GGTTTTGGAA TGTTTACTAC 2040
```

FIG. 20B

```
ACTCGGATAT TTGATATGTG GATTTCGAGT CGTCTTAATG TATAGATTTG AAGAAGAGCT 2100
GTTTTTACGA TCCCTTCAGG ATTACAAAAT TCAAAGTGCG TTGCTAGTAC CAACCCTATT 2160
TTCATTCTTC GCCAAAAGCA CTCTGATTGA CAAATACGAT TTATCTAATT TACACGAAAT 2220
TGCTTCTGGG GGCGCACCTC TTTCGAAAGA AGTCGGGGAA GCGGTTGCAA AACGCTTCCA 2280
TCTTCCAGGG ATACGACAAG GATATGGGCT CACTGAGACT ACATCAGCTA TTCTGATTAC 2340
ACCCGAGGGG GATGATAAAC CGGGCGCGGT CGGTAAAGTT GTTCCATTTT TTGAAGCGAA 2400
GGTTGTGGAT CTGGATACCG GGAAAACGCT GGGCGTTAAT CAGAGAGGCG AATTATGTGT 2460
CAGAGGACCT ATGATTATGT CCGGTTATGT AAACAATCCG GAAGCGACCA ACGCCTTGAT 2520
TGACAAGGAT GGATGGCTAC ATTCTGGAGA CATAGCTTAC TGGGACGAAG ACGAACACTT 2580
CTTCATAGTT GACCGCTTGA AGTCTTTAAT TAAATACAAA GGATATCAGG TGGCCCCCGC 2640
TGAATTGGAA TCGATATTGT TACAACACCC CAACATCTTC GACGCGGGCG TGGCAGGTCT 2700
TCCCGACGAT GACGCCGGTG AACTTCCCGC CGCCGTTGTT GTTTTGGAGC ACGGAAAGAC 2760
GATGACGGAA AAAGAGATCG TGGATTACGT CGCCAGTCAA GTAACAACCG CGAAAAAGTT 2820
GCGCGGAGGA GTTGTGTTTG TGGACGAAGT ACCGAAAGGT CTTACCGGAA AACTCGACGC 2880
AAGAAAAATC AGAGAGATCC TCATAAAGGC CAAGAAGGGC GGAAAGTCCA AATTGTAAAA 2940
TGTAACTGTA TTCAGCGATG ACGAAATTCT TAGCTATTGT AATGGGGGAT CCCCAACTTG 3000
TTTATTGCAG CTTATAATGG TTACAAATAA AGCAATAGCA TCACAAATTT CACAAATAAA 3060
```

FIG. 20C

```
GCATTTTTT CACTGCATTC TAGTTGTGGT TTGTCCAAAC TCATCAATGT ATCTTATCAT  3120
GTCTGGATCG GATCGATCCC CGGGTACCGA GCTCGAATTC GTAATCATGG TCATAGCTGT  3180
TTCCTGTGTG AAATTGTTAT CCGCTCACAA TTCCACACAA CATACGAGCC GGAAGCATAA  3240
AGTGTAAAGC CTGGGGTGCC TAATGAGTGA GCTAACTCAC ATTAATTGCG TTGCGCTCAC  3300
TGCCCGCTTT CCAGTCGGGA AACCTGTCGT GCCAGCTGCA TTAATGAATC GGCCAACGCG  3360
CGGGGAGAGG CGGTTTGCGT ATTGGGCGCT CTTCCGCTTC CTCGCTCACT GACTCGCTGC  3420
GCTCGGTCGT TCGGCTGCGG CGAGCGGTAT CAGCTCACTC AAAGGCGGTA ATACGGTTAT  3480
CCACAGAATC AGGGGATAAC GCAGGAAAGA ACATGTGAGC AAAAGGCCAG CAAAAGGCCA  3540
GGAACCGTAA AAAGGCCGCG TTGCTGGCGT TTTTCCATAG GCTCCGCCCC CCTGACGAGC  3600
ATCACAAAAA TCGACGCTCA AGTCAGAGGT GGCGAAACCC GACAGGACTA TAAAGATACC  3660
AGGCGTTTCC CCCTGGAAGC TCCCTCGTGC GCTCTCCTGT TCCGACCCTG CCGCTTACCG  3720
GATACCTGTC CGCCTTTCTC CCTTCGGGAA GCGTGGCGCT TTCTCATAGC TCACGCTGTA  3780
GGTATCTCAG TTCGGTGTAG GTCGTTCGCT CCAAGCTGGG CTGTGTGCAC GAACCCCCCG  3840
TTCAGCCCGA CCGCTGCGCC TTATCCGGTA ACTATCGTCT TGAGTCCAAC CCGGTAAGAC  3900
ACGACTTATC GCCACTGGCA GCAGCCACTG GTAACAGGAT TAGCAGAGCG AGGTATGTAG  3960
GCGGTGCTAC AGAGTTCTTG AAGTGGTGGC CTAACTACGG CTACACTAGA AGGACAGTAT  4020
TTGGTATCTG CGCTCTGCTG AAGCCAGTTA CCTTCGGAAA AAGAGTTGGT AGCTCTTGAT  4080
```

FIG. 20D

```
CCGGCAAACA AACCACCGCT GGTAGCGGGTG GTTTTTTGT TTGCAAGCAG CAGATTACGC 4140
GCAGAAAAAA AGGATCTCAA GAAGATCCTT TGATCTTTTC TACGGGGTCT GACGCTCAGT 4200
GGAACGAAAA CTCACGTTAA GGGATTTTGG TCATGAGATT ATCAAAAAGG ATCTTCACCT 4260
AGATCCTTTT AAATTAAAAA TGAAGTTTTA AATCAATCTA AAGTATATAT GAGTAAACTT 4320
GGTCTGACAG TTACCAATGC TTAATCAGTG AGGCACCTAT CTCAGCGATC TGTCTATTTC 4380
GTTCATCCAT AGTTGCCTGA CTCCCCGTCG TGTAGATAAC TACGATACGG GAGGGCTTAC 4440
CATCTGGCCC CAGTGCTGCA ATGATACCGC GAGACCCACG CTCACCGGCT CCAGATTTAT 4500
CAGCAATAAA CCAGCCAGCC GGAAGGGCCG AGCGCAGAAG TGGTCCTGCA ACTTTATCCG 4560
CCTCCATCCA GTCTATTAAT TGTTTGCCGG AAGCTAGAGT AAGTAGTTCG CCAGTTAATA 4620
GTTTGCGCAA CGTTGTTGCC ATTGCTACAG GCATCGTGGT GTCACGCTCG TCGTTTGGTA 4680
TGGCTTCATT CAGCTCCGGT TCCCAACGAT CAAGGCGAGT TACATGATCC CCCATGTTGT 4740
GCAAAAAAGC GGTTAGCTCC TTCGGTCCTC CGATCGTTGT CAGAAGTAAG TTGGCCGCAG 4800
TGTTATCACT CATGGTTATG GCAGCACTGC ATAATTCTCT TACTGTCATG CCATCCGTAA 4860
GATGCTTTTC TGTGACTGGT GAGTACTCAA CCAAGTCATT CTGAGAATAG TGTATGCGGC 4920
GACCGAGTTG CTCTTGCCCG GCGTCAATAC GGGATAAATAC CGCGCCACAT AGCAGAACTT 4980
TAAAAGTGCT CATCATTGGA AAACGTTCTT CGGGGCGAAA ACTCTCAAGG ATCTTACCGC 5040
TGTTGAGATC CAGTTCGATG TAACCCACTC GTGCACCCAA CTGATCTTCA GCATCTTTTA 5100
```

FIG. 20E

```
CTTTCACCAG CGTTTCTGGG TGAGCAAAAA CAGGAAGGCA AAATGCCGCA AAAAAGGGAA 5160
TAAGGGCGAC ACGGAAATGT TGAATACTCA TACTCTTCCT TTTTCAATAT TATTGAAGCA 5220
TTTATCAGGG TTATTGTCTC ATGAGCGGAT ACATATTTGA ATGTATTTAG AAAAATAAAC 5280
AAATAGGGGT TCCGCGCACA TTTCCCCGAA AAGTGCCACC TGACGTCTAA GAAACCATTA 5340
TTATCATGAC ATTAACCTAT AAAAATAGGC GTATCACGAG GCCTATGCGG TGTGAAATAC 5400
CGCACAGATG CGTAAGGAGA AAATACCGCA TCAGGCGCCA TTCGCCATTC AGGCTGCGCA 5460
ACTGTTGGGA AGGGCGATCG GTGCGGGCCT CTTCGCTATT ACGCCAGCTG GCGAAAGGGG 5520
GATGTGCTGC AAGGCGATTA AGTTGGGTAA CGCCAGGGTT TTCCCAGTCA CGACGTTGTA 5580
AAACGACGGC CAGTGCCAAG CTTGCATGCC TGCAGGTCGA                      5620
```

FIG. 20F

PACKAGING SYSTEMS FOR HUMAN RECOMBINANT ADENOVIRUS TO BE USED IN GENE THERAPY

CROSS REFERENCE TO RELATED APPLICATIONS

This patent application is a continuation of Ser. No. 09/506,548, filed Feb. 16, 2000, now U.S. Pat. No. 6,602,706, which is a division of Ser. No. 09/334,765, filed Jun. 16, 1999, now U.S. Pat. No. 6,238,893, which is a continuation of Ser. No. 08/793,170, filed Mar. 25, 1997, now U.S. Pat. No. 5,994,128, which was the National Stage application under 35 U.S.C. § 371 of International patent application PCT/NL96/00244, filed Jun. 14, 1996, which itself claims priority from European Patent Application EP 95201728.3, filed Jun. 26, 1995, and European Patent Application EP 95201611.1, filed Jun. 15, 1995, each of which is hereby incorporated herein by this reference.

BACKGROUND OF THE INVENTION

1. Technical Field

The invention relates to the field of recombinant DNA technology, more in particular to the field of gene therapy. In particular, the invention relates to gene therapy using materials derived from adenovirus, specifically human recombinant adenovirus. It especially relates to novel virus derived vectors and novel packaging cell lines for vectors based on adenoviruses.

2. Related Art

Gene therapy is a recently developed concept for which a wide range of applications can be and have been envisioned. In gene therapy, a molecule carrying genetic information is introduced into some or all cells of a host, as a result of which the genetic information is added to the host in a functional format.

The genetic information added may be a gene or a derivative of a gene, such as a cDNA, which encodes a protein. This is a functional format in that the protein can be expressed by the machinery of the host cell.

The genetic information can also be a sequence of nucleotides complementary to a sequence of nucleotides (either DNA or RNA) present in the host cell. This is a functional format in that the added DNA (nucleic acid) molecule or copies made thereof in situ are capable of base pairing with the complementary sequence present in the host cell.

Applications include the treatment of genetic disorders by supplementing a protein or other substance which, because of the genetic disorder, is either absent or present in insufficient amounts in the host, the treatment of tumors, and the treatment of other acquired diseases such as (auto)immune diseases, infections, etc.

As may be inferred from the above, there are basically three different approaches in gene therapy: the first directed towards compensating for a deficiency in a (mammalian) host, the second directed towards the removal or elimination of unwanted substances (organisms or cells) and the third towards application of a recombinant vaccine (against tumors or foreign micro-organisms).

For the purpose of gene therapy, adenoviruses carrying deletions have been proposed as suitable vehicles for genetic information. Adenoviruses are non-enveloped DNA viruses. Gene-transfer vectors derived from adenoviruses (so-called "adenoviral vectors") have a number of features that make them particularly useful for gene transfer for such purposes. For example, the biology of the adenovirus is characterized in detail, the adenovirus is not associated with severe human pathology, the adenovirus is extremely efficient in introducing its DNA into the host cell, the adenovirus can infect a wide variety of cells and has a broad host-range, the adenovirus can be produced in large quantities with relative ease, and the adenovirus can be rendered replication defective by deletions in the early-region 1 ("E1") of the viral genome.

The adenovirus genome is a linear double-stranded DNA molecule of approximately 36,000 base pairs with the 55 kDa terminal protein covalently bound to the 5' terminus of each strand. The adenoviral ("Ad") DNA contains identical Inverted Terminal Repeats ("ITR") of about 100 base pairs with the exact length depending on the serotype. The viral origins of replication are located within the ITRs exactly at the genome ends. DNA synthesis occurs in two stages. First, the replication proceeds by strand displacement, generating a daughter duplex molecule and a parental displaced strand. The displaced strand is single stranded and can form a so-called "panhandle" intermediate, which allows replication initiation and generation of a daughter duplex molecule. Alternatively, replication may proceed from both ends of the genome simultaneously, obviating the requirement to form the panhandle structure. The replication is summarized in FIG. 14 adapted from Lechner and Kelly (1977).

During the productive infection cycle, the viral genes are expressed in two phases: the early phase, which is the period up to viral DNA replication, and the late phase, which coincides with the initiation of viral DNA replication. During the early phase, only the early gene products, encoded by regions E1, E2, E3 and E4, are expressed, which carry out a number of functions that prepare the cell for synthesis of viral structural proteins (Berk, 1986). During the late phase, the late viral gene products are expressed in addition to the early gene products, and host cell DNA and protein synthesis are shut off. Consequently, the cell becomes dedicated to the production of viral DNA and of viral structural proteins (Tooze, 1981).

The E1 region of adenovirus is the first region of adenovirus expressed after infection of the target cell. This region consists of two transcriptional units, the E1A and E1B genes, which both are required for oncogenic transformation of primary (embryonic) rodent cultures. The main functions of the E1A gene products are 1) to induce quiescent cells to enter the cell cycle and resume cellular DNA synthesis and 2) to transcriptionally activate the E1B gene and the other early regions (E2, E3, E4). Transfection of primary cells with the E1A gene alone can induce unlimited proliferation (immortalization) but does not result in complete ransformation. However, expression of E1A in most cases results in induction of programmed cell death (apoptosis) and only occasionally immortalization (Jochemsen et al., 1987). Co-expression of the E1B gene is required to prevent induction of apoptosis and for complete morphological transformation to occur. In established immortal cell lines, high level expression of E1A can cause complete transformation in the absence of E1B (Roberts et al., 1985).

The E1B encoded proteins assist E1A in redirecting the cellular functions to allow viral replication. The E1B 55 kDa and E4 33 kDa proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm concomitantly with the onset of the late phase of infection. The E1B 21 kDa protein is important for correct temporal control of the productive infection cycle, thereby preventing premature death of the host cell before the virus life cycle has been completed. Mutant viruses incapable of expressing the E1B 21 kDa gene product exhibit a shortened infection cycle that is accompanied by excessive degradation of host cell chromosomal DNA (deg-phenotype) and in an enhanced cytopathic effect (cyt-phenotype) (Telling et al., 1994). The deg and cyt phenotypes are suppressed when in addition the E1A gene is mutated, indicating that these phenotypes are a function of E1A (White et al., 1988). Furthermore, the E1B 21 kDa protein slows down the rate by which E1A switches on the other viral genes. It is not yet known through which mechanisms E1B 21 kDa quenches these E1A dependent functions.

Vectors derived from human adenoviruses, in which at least the E1 region has been deleted and replaced by a gene of interest, have been used extensively for gene therapy experiments in the pre-clinical and clinical phase.

As stated before, all adenovirus vectors currently used in gene therapy are believed to have a deletion in the E1 region, where novel genetic information can be introduced. The E1 deletion renders the recombinant virus replication defective (Stratford-Perricaudet and Perricaudet, 1991). We have demonstrated that recombinant adenoviruses are able to efficiently transfer recombinant genes to the rat liver and airway epithelium of rhesus monkeys (Bout et al., 1994b; Bout et al., 1994a). In addition, we (Vincent et al., 1996a; Vincent et al., 1996b) and others (see, e.g., Haddada et al., 1993) have observed a very efficient in vivo adenovirus mediated gene transfer to a variety of tumor cells in vitro and to solid tumors in animals models (lung tumors, glioma) and human xenografts in immunodeficient mice (lung) in vivo (reviewed by Blaese et al., 1995).

In contrast to (for instance) retroviruses, adenoviruses 1) do not integrate into the host cell genome, 2) are able to infect non-dividing cells, and 3) are able to efficiently transfer recombinant genes in vivo (Brody and Crystal, 1994). Those features make adenoviruses attractive candidates for in vivo gene transfer of, for instance, suicide or cytokine genes into tumor cells.

However, a problem associated with current recombinant adenovirus technology is the possibility of unwanted generation of replication competent adenovirus ("RCA") during the production of recombinant adenovirus (Lochmüller et al., 1994; Imler et al., 1996). This is caused by homologous recombination between overlapping sequences from the recombinant vector and the adenovirus constructs present in the complementing cell line, such as the 293 cells (Graham et al, 1977). RCA is undesirable in batches to be used in clinical trials because RCA 1) will replicate in an uncontrolled fashion, 2) can complement replication defective recombinant adenovirus, causing uncontrolled multiplication of the recombinant adenovirus, and 3) batches containing RCA induce significant tissue damage and hence strong pathological side effects (Lochmüiller et al., 1994). Therefore, batches to be used in clinical trials should be proven free of RCA (Ostrove, 1994).

It was generally thought that E1-deleted vectors would not express any other adenovirus genes. However, recently it has been demonstrated that some cell types are able to express adenovirus genes in the absence of E1 sequences. This indicates that some cell types possess the machinery to drive transcription of adenovirus genes. In particular, it was demonstrated that such cells synthesize E2A and late adenovirus proteins.

In a gene therapy setting, this means that transfer of the therapeutic recombinant gene to somatic cells not only results in expression of the therapeutic protein but may also result in the synthesis of viral proteins. Cells that express adenoviral proteins are recognized and killed by Cytotoxic T Lymphocytes, which thus 1) eradicates the transduced cells and 2) causes inflammations (Bout et al., 1994a; Engelhardt et al., 1993; Simon et al., 1993). As this adverse reaction hampers gene therapy, several solutions to this problem have been suggested, such as 1) using immunosuppressive agents after treatment, 2) retention of the adenovirus E3 region in the recombinant vector (see European patent application EP 95202213), and 3) using temperature sensitive ("ts") mutants of human adenovirus, which have a point mutation in the E2A region rendering them temperature sensitive, as has been claimed in patent WO/28938.

However, these strategies to circumvent the immune response have their limitations. The use of ts mutant recombinant adenovirus diminishes the immune response to some extent but was less effective in preventing pathological responses in the lungs (Engelhardt et al., 1994a).

The E2A protein may induce an immune response by itself, and it plays a pivotal role in the switch to the synthesis of late adenovirus proteins. Therefore, it is attractive to make temperature sensitive recombinant human adenoviruses.

A major drawback of this system is the fact that although the E2 protein is unstable at the non-permissive temperature, the immunogenic protein is still being synthesized. In addition, it is to be expected that the unstable protein does activate late gene expression, albeit to a low extent. ts125 mutant recombinant adenoviruses have been tested, and prolonged recombinant gene expression was reported (Yang et al., 1994b; Engelhardt et al., 1994a; Engelhardt et al., 1994b; Yang et al., 1995). However, pathology in the lungs of cotton rats was still high (Engelhardt et al., 1994a), indicating that the use of ts mutants results in only a partial improvement in recombinant adenovirus technology. Others (Fang et al., 1996) did not observe prolonged gene expression in mice and dogs using ts125 recombinant adenovirus. An additional difficulty associated with the use of ts125 mutant adenoviruses is that a high frequency of reversion is observed. These revertants are either real revertants or the result of second site mutations (Kruijer et al., 1983; Nicolas et al., 1981). Both types of revertants have an E2A protein that functions at normal temperature and, therefore, have toxicity similar to the wild-type virus.

BRIEF SUMMARY OF THE INVENTION

In one aspect of the invention, this problem in virus production is solved in that we have developed packaging cells that have no overlapping sequences with a new basic vector and thus are suited for safe large scale production of recombinant adenoviruses. One of the additional problems associated with the use of recombinant adenovirus vectors is the host-defense reaction against treatment with adenovirus.

Briefly, recombinant adenoviruses are deleted for the E1 region. The adenovirus E1 products trigger the transcription of the other early genes (E2, E3, E4), which consequently activate expression of the late virus genes.

In another aspect of the present invention, we therefore delete E2A coding sequences from the recombinant adenovirus genome and transfect these E2A sequences into the (packaging) cell lines containing E1 sequences to complement recombinant adenovirus vectors.

Major hurdles in this approach are 1) that E2A should be expressed to very high levels and 2) that E2A protein is very toxic to cells.

The current invention, in yet another aspect, therefore discloses use of the ts125 mutant E2A gene, which produces a protein that is not able to bind DNA sequences at the non-permissive temperature. High levels of this protein may be maintained in the cells (because it is non-toxic at this temperature) until the switch to the permissive temperature is made. This can be combined with placing the mutant E2A gene under the direction of an inducible promoter, such as, for instance, tet, methallothionein, steroid inducible promoter, retinoic acid β-receptor, or other inducible systems. However, in yet another aspect of the invention, the use of an inducible promoter to control the moment of production of toxic wild-type E2A is disclosed.

Two salient additional advantages of E2A-deleted recombinant adenovirus are 1) the increased capacity to harbor heterologous sequences and 2) the permanent selection for cells that express the mutant E2A. This second advantage relates to the high frequency of reversion of ts125 mutation: when reversion occurs in a cell line harboring ts125 E2A, this will be lethal to the cell. Therefore, there is a permanent selection for those cells that express the ts125 mutant E2A protein. In addition, as we in one aspect of the invention generate E2A-deleted recombinant adenovirus, we will not have the problem of reversion in our adenoviruses.

In yet another aspect of the invention, as a further improvement, the use of non-human cell lines as packaging cell lines is disclosed.

For GMP production of clinical batches of recombinant viruses, it is desirable to use a cell line that has been used widely for production of other biotechnology products. Most of the latter cell lines are of monkey origin, which have been used to produce, for example, vaccines.

These cells can not be used directly for the production of recombinant human adenovirus, as human adenovirus cannot replicate or replicates only to low levels in cells of monkey origin. A block in the switch of early to late phase of adenovirus lytic cycle underlies defective replication. However, host range mutations in the human adenovirus genome are described (hr400–404), which allow replication of human viruses in monkey cells. These mutations reside in the gene encoding E2A protein (Klessig and Grodzicker, 1979; Klessig et al., 1984; Rice and Klessig, 1985; Klessig et al., 1984). Moreover, mutant viruses have been described that harbor both the hr and temperature-sensitive ts125 phenotype (Brough et al., 1985; Rice and Klessig, 1985).

We therefore generate packaging cell lines of monkey origin (e.g., VERO, CV1) that harbor:
1) E1 sequences, to allow replication of E1/E2 defective adenoviruses, and
2) E2A sequences, containing the hr mutation and the ts125 mutation, named ts400 (Brough et al., 1985; Rice and Klessig, 1985) to prevent cell death by E2A overexpression, and/or
3) E2A sequences, just containing the hr mutation, under the control of an inducible promoter, and/or
4) E2A sequences, containing the hr mutation and the ts125 mutation (ts400), under the control of an inducible promoter.

Furthermore we disclose the construction of novel and improved combinations of packaging cell lines and recombinant adenovirus vectors. We provide:
1) A novel packaging cell line derived from diploid human embryonic retinoblasts ("HER") that harbors nt. 80–5788 of the Ad5 genome. This cell line, named 911, deposited under no. 95062101 at the ECACC™, has many characteristics that make it superior to the commonly used 293 cells (Fallaux et al., 1996);
2) Novel packaging cell lines that express just E1A genes and not E1B genes. Established cell lines (and not human diploid cells of which 293 and 911 cells are derived) are able to express E1A to high levels without undergoing apoptotic cell death, as occurs in human diploid cells that express E1A in the absence of E1B. Such cell lines are able to trans-complement E1B-defective recombinant adenoviruses, because viruses mutated for E1B 21 kDa protein are able to complete viral replication even faster than wild-type adenoviruses (Telling et al., 1994). The constructs are described in detail below and are graphically represented in FIGS. 1–5. The constructs are transfected into the different established cell lines and are selected for high expression of E1A. This is done by operatively linking a selectable marker gene (e.g., NEO gene) directly to the E1B promoter. The E1B promoter is transcriptionally activated by the E1A gene product, and, therefore, resistance to the selective agent (e.g., G418 in the case of NEO is used as the selection marker) results in direct selection for desired expression of the E1A gene;
3) Packaging constructs that are mutated or deleted for E1B 21 kDa, but just express the 55 kDa protein;
4) Packaging constructs to be used for generation of complementing packaging cell lines from diploid cells (not exclusively of human origin) without the need for selection with marker genes. These cells are immortalized by expression of E1A. However, in this particular case, expression of E1B is essential to prevent apoptosis induced by E1A proteins. Selection of E1 expressing cells is achieved by selection for focus formation (immortalization), as described for 293 cells (Graham et al., 1977) and 911 cells (Fallaux et al., 1996), that are E1-transformed human embryonic kidney ("HEK") cells and human embryonic retinoblasts ("HER"), respectively;
5) After transfection of HER cells with construct pIG.E1B (see FIG. 4), seven independent cell lines could be established. These cell lines were designated PER.C 1, PER.C3, PER.C4, PER.C5, PER.C6™, PER.C8, and PER.C9. PER denotes PGK-E1-Retinoblasts. These cell lines express E1A and E1B proteins, are stable (e.g., PER.C6™ for more than 57 passages), and complement E1 defective adenovirus vectors. Yields of recombinant adenovirus obtained on PER cells are a little higher than obtained on 293 cells. One of these cell lines (PER.C6™) has been deposited at the ECACC™ under number 96022940;
6) New adenovirus vectors with extended E1 deletions (deletion nt. 459–3510). Those viral vectors lack sequences homologous to E1 sequences in said packaging cell lines. These adenoviral vectors contain pIX promoter sequences and the pIX gene, as pIX (from its natural promoter sequences) can only be expressed from the vector and not by packaging cells (Matsui et al., 1986, Hoeben and Fallaux, personal communication; Imler et al., 1996);
7) E2A expressing packaging cell lines preferably based on either E1A expressing established cell lines or E1A–E1B expressing diploid cells (see under 2–4). E2A expression is either under the control of an inducible promoter or the E2A ts125 mutant is driven by either an inducible or a constitutive promoter.
8) Recombinant adenovirus vectors as described before (see 6) but carrying an additional deletion of E2A sequences;
9) Adenovirus packaging cells from monkey origin that are able to trans-complement E1-defective recombinant adenoviruses. They are preferably co-transfected with pIG.E1A.E1B and pIG.NEO and selected for NEO resistance. Such cells expressing E1A and E1B are able to transcomplement E1 defective recombinant human adenoviruses but will do so inefficiently because of a block of the synthesis of late adenovirus proteins in cells of monkey origin (Klessig and Grodzicker, 1979). To overcome this problem, we generate recombinant adenoviruses that harbor a host-range mutation in the E2A gene, allowing human adenoviruses to replicate in monkey cells. Such viruses are generated as described in FIG. 12, except DNA from an hr-mutant is used for homologous recombination; and 10) Adenovirus packaging cells from monkey origin as described under 9, except that they will also be co-transfected with E2A sequences harboring the hr mutation. This allows replication of human adenoviruses lacking E1 and E2A (see under 8). E2A in these cell lines is either under the control of an inducible promoter or the tsE2A mutant is used. In the latter case, the E2A gene will thus carry both the ts mutation and the hr mutation (derived from ts400). Replication competent human adenoviruses have been described that harbor both mutations (Brough et al., 1985; Rice and Klessig, 1985).

A further aspect of the invention provides otherwise improved adenovirus vectors, as well as novel strategies for generation and application of such vectors and a method for the intracellular amplification of linear DNA fragments in mammalian cells.

BRIEF DESCRIPTION OF THE DRAWINGS

The following figures and drawings may help to understand the invention:

FIGS. 11A and 11B illustrate new adenovirus packaging constructs which do not have sequence overlap with new adenovirus vectors;

FIG. 15 illustrates a potential hairpin conformation of a single-stranded DNA molecule that contains the HP/asp sequence (SEQ ID NO:22);

FIGS. 20A–20F recite the nucleotide sequence of pICL 5620BPS DNA (circular) (SEQ ID NO:21).

DETAILED DESCRIPTION OF THE INVENTION

The so-called "minimal" adenovirus vectors according to the present invention retain at least a portion of the viral genome that is required for encapsidation of the genome into virus particles (the encapsidation signal), as well as at least one copy of at least a functional part or a derivative of the ITR, that is DNA sequences derived from the termini of the linear adenovirus genome. The vectors according to the present invention will also contain a transgene linked to a promoter sequence to govern expression of the transgene. Packaging of the so-called minimal adenovirus vector can be achieved by co-infection with a helper virus or, alternatively, with a packaging deficient replicating helper system, as described below.

Figure 13:
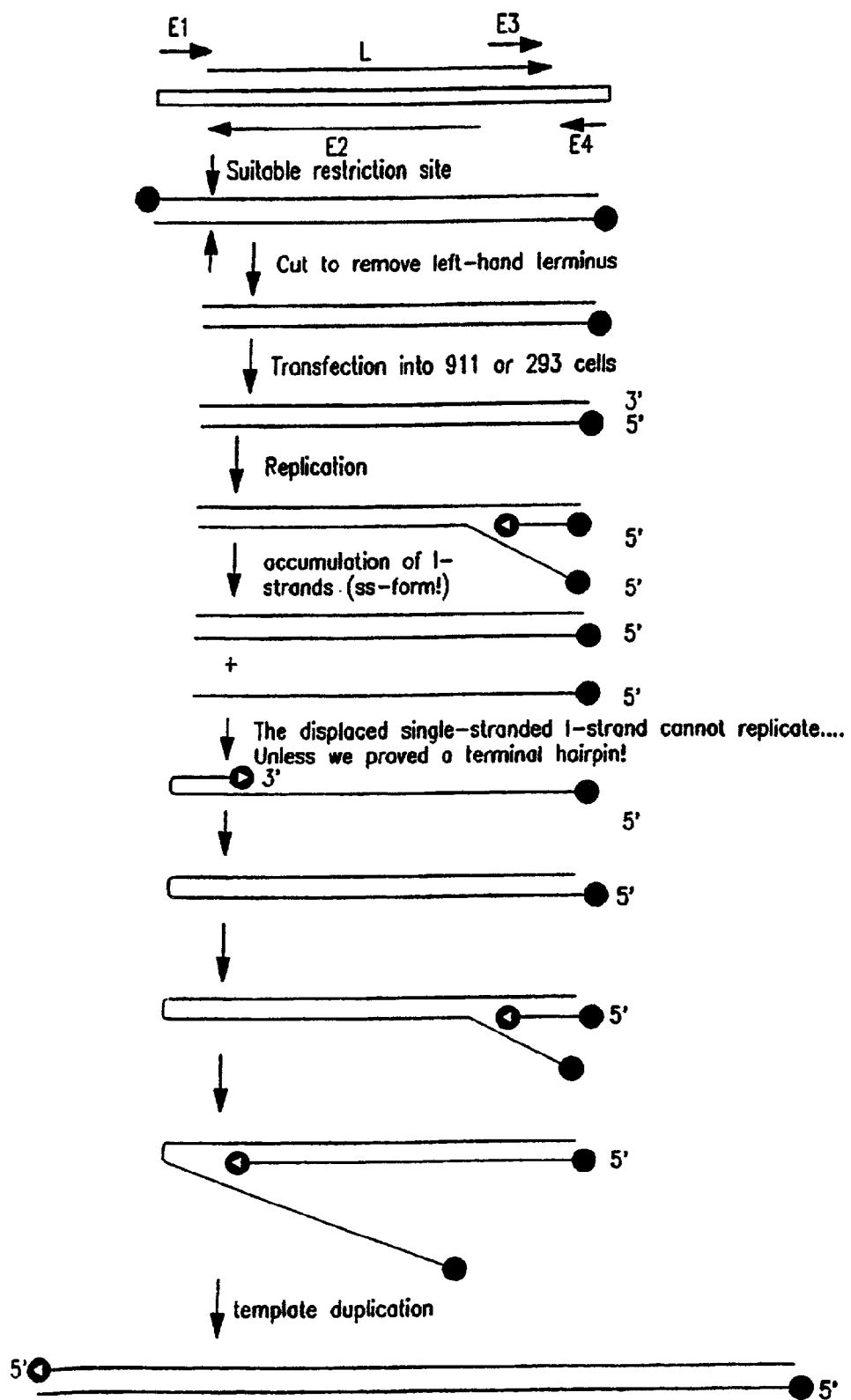
FIG. 13 illustrates the adenovirus double-stranded DNA genome indicating the approximate locations of E1, E2, E3, E4, and L regions.
Figure 14:
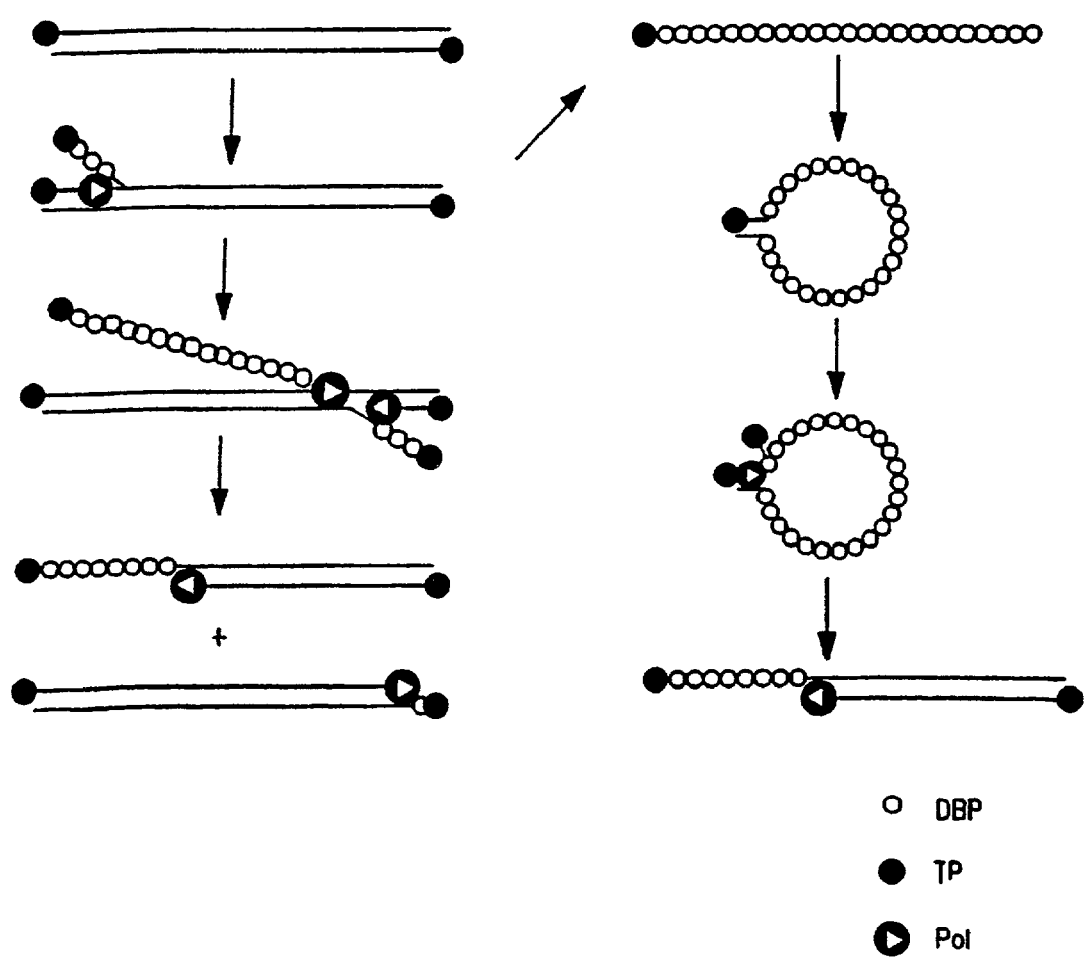
FIG. 14 illustrates the adenovirus genome is shown in the top left with the origins of replication located within the left and right ITRs at the genome ends.

Adenovirus-derived DNA fragments that can replicate in suitable cell lines and that may serve as a packaging deficient replicating helper system are generated as follows. These DNA fragments retain at least a portion of the transcribed region of the "late" transcription unit of the adenovirus genome and carry deletions in at least a portion of the E1 region and deletions in at least a portion of the encapsidation signal. In addition, these DNA fragments contain at least one copy of an ITR. At one terminus of the transfected DNA molecule an ITR is located. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin-structure can serve as a primer for DNA synthesis by cellular and/or adenovirus-encoded DNA polymerases, resulting in conversion into a double-stranded form of at least a portion of the DNA molecule. Further replication initiating at the ITR will result in a linear double-stranded DNA molecule that is flanked by two ITRs and is larger than the original transfected DNA molecule (see FIG. 13). This molecule can replicate itself in the transfected cell by virtue of the adenovirus proteins encoded by the DNA molecule and the adenoviral and cellular proteins encoded by genes in the host-cell genome. This DNA molecule can not be encapsidated due to its large size (greater than 39000 base pairs) or due to the absence of a functional encapsidation signal. This DNA molecule is intended to serve as a helper for the production of defective adenovirus vectors in suitable cell lines.

The invention also comprises a method for amplifying linear DNA fragments of variable size in suitable mammalian cells. These DNA fragments contain at least one copy of the ITR at one of the termini of the fragment. The other end may contain an ITR, or alternatively, a DNA sequence that is complementary to a portion of the same strand of the DNA molecule other than the ITR. If, in the latter case, the two complementary sequences anneal, the free 3'-hydroxyl group of the 3' terminal nucleotide of the hairpin structure can serve as a primer for DNA synthesis by cellular and/or adenovirus-encoded DNA polymerases, resulting in conversion of the displaced strand into a double stranded form of at least a portion of the DNA molecule. Further replication initiating at the ITR will result in a linear double-stranded DNA molecule that is flanked by two ITRs, which is larger than the original transfected DNA molecule. A DNA molecule that contains ITR sequences at both ends can replicate itself in transfected cells by virtue of the presence of at least the adenovirus E2 proteins (viz. the DNA-binding protein ("DBP"), the adenovirus DNA polymerase ("Ad-pol"), and the pre-terminal protein ("pTP"). The required proteins may be expressed from adenovirus genes on the DNA molecule itself, from adenovirus E2 genes integrated in the host-cell genome, or from a replicating helper fragment, as described above.

Several groups have shown that the presence of ITR sequences at the end of DNA molecules are sufficient to generate adenovirus minichromosomes that can replicate, if the adenovirus-proteins required for replication are provided in trans, for example, by infection with a helper virus (Hu et al., 1992; Wang and Pearson, 1985; Hay et al., 1984). Hu et al. (1992) observed the presence and replication of symmetrical adenovirus minichromosome-dimers after transfection of plasmids containing a single ITR. The authors were able to demonstrate that these dimeric minichromosomes arise after tail-to-tail ligation of the single ITR DNA molecules. In DNA extracted from defective adenovirus type 2 particles, dimeric molecules of various sizes have also been observed using electron-microscopy (Daniell, 1976). It was suggested that the incomplete genomes were formed by illegitimate recombination between different molecules and that variations in the position of the sequence at which the illegitimate base pairing occurred were responsible for the heterogeneous nature of the incomplete genomes. Based on this mechanism it was speculated that, in theory, defective molecules with a total length of up to two times the normal genome could be generated. Such molecules could contain duplicated sequences from either end of the genome. However, no DNA molecules larger than the full-length virus were found packaged in the defective particles (Daniell, 1976). This can be explained by the size limitations that apply to the packaging. In addition, it was observed that in the virus particles, DNA molecules with a duplicated left-end predominated over those containing the right-end terminus (Daniell, 1976). This is fully explained by the presence of the encapsidation signal near that left-end of the genome (Gräble and Hearing, 1990; Gräble and Hearing, 1992; Hearing et al., 1987).

The major problems associated with the current adenovirus-derived vectors are:

1) The strong immunogenicity of the virus particle;
2) The expression of adenovirus genes that reside in the adenoviral vectors, resulting in a Cytotoxic T-cell response against the transduced cells; and
3) The low amount of heterologous sequences that can be accommodated in the current vectors (Up to maximally approximately 8000 base pairs ("bp") of heterologous DNA).

The strong immunogenicity of the adenovirus particle results in an immunological response of the host, even after a single administration of the adenoviral vector. As a result of the development of neutralizing antibodies, a subsequent administration of the virus will be less effective or even completely ineffective. However, a prolonged or persistent expression of the transferred genes will reduce the number of administrations required and may bypass the problem.

With regard to problem 2), experiments performed by Wilson and collaborators have demonstrated that after adenovirus-mediated gene transfer into immunocompetent animals, the expression of the transgene gradually decreases and disappears approximately 2–4 weeks post-infection (Yang et al. 1994a; Yang et al., 1994b). This is caused by the development of a Cytotoxic T-Cell ("CTL") response against the transduced cells. The CTLs were directed against adenovirus proteins expressed by the viral vectors. In the transduced cells, synthesis of the adenovirus DNA-binding protein (the E2A-gene product), penton, and fiber proteins (late-gene products) could be established. These adenovirus proteins, encoded by the viral vector, were expressed despite deletion of the E1 region. This demonstrates that deletion of the E1 region is not sufficient to completely prevent expression of the viral genes (Engelhardt et al., 1994a).

With regard to problem 3), studies by Graham and collaborators have demonstrated that adenoviruses are capable of encapsidating DNA of up to 105% of the normal genome size (Bett et al., 1993). Larger genomes tend to be unstable, resulting in loss of DNA sequences during propagation of the virus. Combining deletions in the E1 and E3 regions of the viral genomes increases the maximum size of the foreign DNA that can be encapsidated to approximately 8.3 kb. In addition, some sequences of the E4 region appear to be dispensable for virus growth (adding another 1.8 kb to the maximum encapsidation capacity). Also, the E2A region can be deleted from the vector when the E2A gene product is provided in trans in the encapsidation cell line, adding another 1.6 kb. It is, however, unlikely that the maximum capacity of foreign DNA can be significantly increased further than 12 kb.

We developed a new strategy for the generation and production of helper-free-stocks of recombinant adenovirus vectors that can accommodate up to 38 kb of foreign DNA. Only two functional ITR sequences and sequences that can function as an encapsidation signal need to be part of the vector genome. Such vectors are called "minimal adenovectors." The helper functions for the minimal adenovectors are provided in trans by encapsidation defective-replication competent DNA molecules that contain all the viral genes encoding the required gene products, with the exception of those genes that are present in the host-cell genome, or genes that reside in the vector genome.

The applications of the disclosed inventions are outlined below and will be illustrated in the experimental part, which is only intended for that purpose and should not be used to reduce the scope of the present invention as understood by those skilled in the art.

Use of the IG Packaging Constructs Diploid Cells.

The constructs, in particular pIG.E1A.E1B, will be used to transfect diploid human cells, such as HER, HEK, and Human Embryonic Lung cells ("HEL"). Transfected cells will be selected for transformed phenotype (focus formation) and tested for their ability to support propagation of E1-deleted recombinant adenovirus, such as IG.Ad.ML-PI.TK. Such cell lines will be used for the generation and (large-scale) production of E1-deleted recombinant adenoviruses. Such cells, infected with recombinant adenovirus, are also intended to be used in vivo as a local producer of recombinant adenovirus, for example, for the treatment of solid tumors.

911 cells are used for the titration, generation, and production of recombinant adenovirus vectors (Fallaux et al., 1996).

HER cells transfected with pIG.E1A.E1B have resulted in 7 independent clones (called PER cells). These clones are used for the production of E1-deleted (including non-overlapping adenovirus vectors) or E1 defective recombinant adenovirus vectors and provide the basis for introduction of, for example, E2B or E2A constructs (e.g., ts125E2A, see below), E4 etc., that will allow propagation of adenovirus vectors that have mutations in, for example, E2A or E4.

In addition, diploid cells of other species that are permissive for human adenovirus, such as the cotton rat (*Sigmodon hispidus*) (Pacini et al., 1984), Syrian hamster (Morin et al., 1987), or chimpanzee (Levrero et al., 1991), will be immortalized with these constructs. Such cells infected with recombinant adenovirus are also intended to be used in vivo for the local production of recombinant adenovirus, for example, for the treatment of solid tumors.

Established Cells

The constructs, in particular pIG.E1A.NEO, can be used to transfect established cells, for example, A549 (human bronchial carcinoma), KB (oral carcinoma), MRC-5 (human diploid lung cell line), or GLC cell lines (small cell lung cancer) (de Leij et al., 1985; Postmus et al., 1988) and selected for NEO resistance. Individual colonies of resistant cells are isolated and tested for their capacity to support propagation of E1-deleted recombinant adenovirus, such as IG.Ad.MLPI.TK. When propagation of E1-deleted viruses on E1A containing cells is possible, such cells can be used for the generation and production of E1-deleted recombinant adenovirus. They can also be used for the propagation of E1A deleted/E1B retained recombinant adenovirus.

Established cells can also be co-transfected with pIG.E1A.E1B and pIG.NEO (or another NEO containing expression vector). Clones resistant to G418 are tested for their ability to support propagation of E1-deleted recombinant adenovirus, such as IG.Ad.MLPI.TK, and used for the generation and production of E1 deleted recombinant adenovirus and will be applied in vivo for local production of recombinant virus, as described for the diploid cells (see previous discussion). All cell lines, including transformed diploid cell lines or NEO-resistant established lines, can be used as the basis for the generation of "next generation" packaging cell lines that support propagation of E1-defective recombinant adenoviruses and that also carry deletions in other genes, such as E2A and E4. Moreover, they will provide the basis for the generation of minimal adenovirus vectors as disclosed herein.

E2 Expressing Cell Lines

Packaging cells expressing E2A sequences are and will be used for the generation and large scale production of E2A-deleted recombinant adenovirus.

The newly generated human adenovirus packaging cell lines or cell lines derived from species permissive for human adenovirus (E2A or ts125E2A: E1A+E2A; E1A+E1B+E2A; E1A−E2A/ts125; E1A+E1B−E2A/ts125) or non-permissive cell lines such as monkey cells (hrE2A or hr+ts125E2A; E1A+hrE2A; E1A+E1B+hrE2A; E1A+hrE2A/ts125; E1A−E1B+hrE2A/ts125) are and will be used for the generation and large scale production of E2A deleted recombinant adenovirus vectors. In addition, they will be applied in vivo for local production of recombinant virus, as described for the diploid cells (see previous discussion).

Novel Adenovirus Vectors

The newly developed adenovirus vectors harboring an E1 deletion of nt. 459–3510 will be used for gene transfer purposes. These vectors are also the basis for the development of further deleted adenovirus vectors that are mutated for, for example, E2A, E2B or E4. Such vectors will be generated, for example, on the newly developed packaging cell lines described above.

Minimal Adenovirus Packaging System

We disclose adenovirus packaging constructs (to be used for the packaging of minimal adenovirus vectors) which have the following characteristics:

1) the packaging construct replicates;
2) the packaging construct can not be packaged because the packaging signal is deleted;
3) the packaging construct contains an internal hairpin-forming sequence (see FIG. 15);
4) because of the internal hairpin structure, the packaging construct is duplicated, that is, the DNA of the packaging construct becomes twice as long as it was before transfection into the packaging cell (in our sample, it duplicates from 35 kb to 70 kb). This duplication also prevents packaging. Note that this duplicated DNA molecule has ITRs at both termini (see, e.g., FIG. 13);
5) this duplicated packaging molecule is able to replicate like a "normal adenovirus" DNA molecule;
6) the duplication of the genome is a prerequisite for the production of sufficient levels of adenovirus proteins required to package the minimal adenovirus vector; and
7) the packaging construct has no overlapping sequences with the minimal vector or cellular sequences that may lead to generation of RCA by homologous recombination.

This packaging system is used to produce minimal adenovirus vectors. The advantages of minimal adenovirus vectors, for example, for gene therapy of vaccination purposes, are well known (accommodation of up to 38 kb; gutting of potentially toxic and immunogenic adenovirus genes).

Adenovirus vectors containing mutations in essential genes (including minimal adenovirus vectors) can also be propagated using this system.

Use of Intracellular E2 Expressing Vectors

Minimal adenovirus vectors are generated using the helper functions provided in trans by packaging-deficient replicating helper molecules. The adenovirus-derived ITR sequences serve as origins of DNA replication in the presence of at least the E2 gene products. When the E2 gene products are expressed from genes in the vector genome (the gene(s) must be driven by an E1-independent promoter), the vector genome can replicate in the target cells. This will allow a significantly increased number of template molecules in the target cells, and, as a result, an increased expression of the genes of interest encoded by the vector. This is of particular interest for application of gene therapy in cancer treatment.

Applications of Intracellular Amplification of Linear DNA Fragments

A similar approach could also be taken if amplification of linear DNA fragments is desired. DNA fragments of known or unknown sequence could be amplified in cells containing the E2 gene products if at least one ITR sequence is located near or at its terminus. There are no apparent constraints on the size of the fragment. Even fragments much larger than the adenovirus genome (36 kb) should be amplified using this approach. It is thus possible to clone large fragments in mammalian cells without either shuttling the fragment into bacteria (such as *E. coli*) or using the polymerase chain reaction ("PCR"). At the end stage of a productive adenovirus infection, a single cell can contain over 100,000 copies of the viral genome. In the optimal situation, the Linear DNA fragments can be amplified to similar levels. Thus, one should be able to extract more than 5 μg of DNA fragment per 10 million cells (for a 35-kbp fragment). This system can be used to express heterologous proteins equivalent to the Simian Virus 40-based COS cell system for research or for therapeutic purposes. In addition, the system can be used to identify genes in large fragments of DNA. Random DNA fragments may be amplified (after addition of ITRs) and expressed during intracellular amplification. Election or selection of those cells with the desired phenotype can be used to enrich the fragment of interest and to isolate the gene.

EXPERIMENTS

Generation of Cell Lines Able to Transcomplement E1 Defective Recombinant Adenovirus Vectors 911 Cell Line We have generated a cell line that harbors E1 sequences of adenovirus type 5 ("Ad5"), able to trans-complement E1 deleted recombinant adenovirus (Fallaux et al., 1996). This cell line was obtained by transfection of human diploid human embryonic retinoblasts ("HER") with pAd5XhoIC, which contains nt. 80–5788 of Ad5. One of the resulting transformants was designated 911. This cell line has been shown to be very useful in the propagation of E1 defective recombinant adenovirus. It was found to be superior to 293 cells. Unlike 293 cells, 911 cells lack a fully transformed phenotype, which most likely is the cause of its better performance as an adenovirus packaging line:

1) plaque assays can be performed faster (4–5 days instead of 8–14 days, as on 293),
2) monolayers of 911 cells survive better under agar overlay, as required for plaque assays, and
3) higher amplification of E1-deleted vectors is obtained.

In addition, unlike 293 cells that were transfected with sheared adenoviral DNA, 911 cells were transfected using a defined construct. Transfection efficiencies of 911 cells are comparable to those of 293.

New Packaging Constructs. Source of Adenovirus Sequences

Adenovirus sequences are derived either from pAd5.SalB, containing nt. 80–9460 of human adenovirus type 5 (Bernards et al., 1983), or from wild-type Ad5 DNA. pAd5.SalB was digested with SalI and XhoI, the large fragment was relegated, and this new clone was named pAd5.X/S. The pTN construct (constructed by Dr. R. Vogels, IntroGene, Leiden, The Netherlands) was used as a source for the human PGK promoter and the NEO gene.

Human PGK Promoter and NEO$^R$ Gene

Transcription of E1A sequences in the new packaging constructs is driven by the human PGK promoter (Michelson et al., 1983; Singer-Sam et al., 1984), derived from plasmid pTN (gift of R. Vogels), which uses pUC 119 (Vieira and Messing, 1987) as a backbone. This plasmid was also used as a source for NEO gene fused to the Hepatitis B Virus ("HBV") poly-adenylation signal.

Fusion of PGK Promoter to E1 Genes

Figure 1:
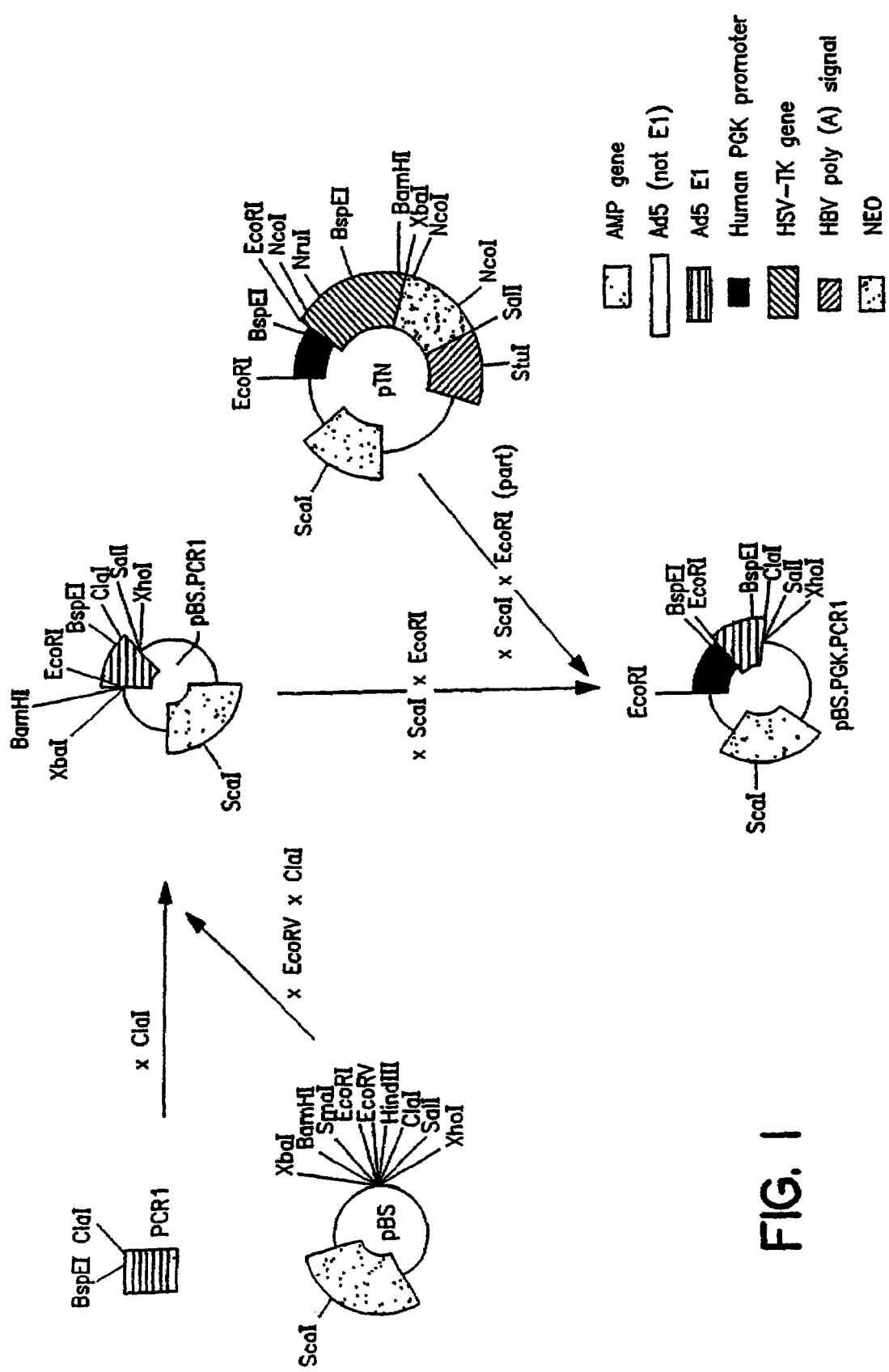
FIG. 1 illustrates the construction of pBS.PGK.PCRI.

As shown in FIG. 1, in order to replace the E1 sequences of Ad5 (ITR, origin of replication, and packaging signal) by heterologous sequences we have amplified E1 sequences (nt.459 to nt. 960) of Ad5 by PCR, using primers Ea-1 (SEQ ID NO:1) and Ea-2 (SEQ ID NO:2) (see Table I). The resulting PCR product was digested with ClaI and ligated into Bluescript (Stratagene), predigested with ClaI and EcoRV, resulting in construct pBS.PCR1.

TABLE I

| Name | (SEQ ID NO) | Sequence | Function |
|---|---|---|---|
| Primer Ea-1 | (SEQ ID NO: 1) a | CGTGTAGTGT ATTTATACCC G | PCR amplification Ad5 nt459 → |
| Primer Ea-2 | (SEQ ID NO: 2) a | TCGTCACTGG GTGGAAAGCC A | PCR amplification Ad5 nt960 ← |
| Primer Ea-3 | (SEQ ID NO: 3) a | TACCCGCCGT CCTAAAATGG C | nt1284–1304 of Ad5 genome |
| Primer Ea-5 | (SEQ ID NO: 4) a | TGGACTTGAG CTGTAAACGC | nt1514–1533 of Ad5 genome |
| Primer Ep-2 | (SEQ ID NO: 5) a | GCCT<u>CCATGG</u> AGGTCAGATG T | nt1721–1702 of Ad5: introduction of NcoI site |
| Primer Eb-1 | (SEQ ID NO: 6) a | GCTTGAGCCC GAGACATGTC | nt3269–3289 of Ad5 genome |
| Primer Eb-2 | (SEQ ID NO: 7) a | CCCC<u>CTCGAG</u>C TCAATCTGTA TCTT | nt3508–3496 of Ad5 genome: introduction of XhoI site |
| Primer SV40-1 | (SEQ ID NO: 8) a | GGGG<u>GATCC</u>G AACTTGTTTA TTGCAGC | Introduction BamHI site (nt2182–2199 of pMLP.TK) adaption of recombinant adenoviruses |
| Primer SV40-2 | (SEQ ID NO: 9) a | GGG<u>AGATCT</u>A GACATGATAA GATAC | Introduction BglII site (nt2312–2297 of pMLP.TK) |
| Primer Ad5-1 | (SEQ ID NO: 10) a | GGG<u>AGATCT</u>G TACTGAAATC TGTGGGC | Introduction of BglII site (nt 2496–2514 of pMLP.TK) |
| Primer Ad5-2 | (SEQ ID NO: 11) a | GGAGGCTGCA GTCTCCAACG GCGT | Rnt2779–2756 of PMLP.TK |
| Primer ITR1 | (SEQ ID NO: 12) a | GGGG<u>GGATCC</u>T CAAATCGTCA CTTCCGT | nt35737–35757 of Ad5 (introduction of BamHI site) |
| Primer ITR2 | (SEQ ID NO: 13 a | GGGG<u>TCTAGA</u> CATCATCAAT AATATAC | nt35935–35919 of Ad5 (introduction of XbaI site) |

TABLE I-continued

| Name | (SEQ ID NO) | Sequence | Function |
|---|---|---|---|
| PCR primer PCR/MLP1 | (SEQ ID NO: 14) b | GGCGAATTCG TCGACATCAT CAATAATATA CC | (Ad5 nt. 10–18) |
| PCT primer PCR/MLP2 | (SEQ ID NO: 15) b | GGCGAATTCG GTACCATCAT CAATAATATA CC | (Ad5 nt. 10–18) |
| PCT primer PCR/MLP3 | (SEQ ID NO: 16) b | CTGTGTACAC CGGCGCA | (Ad5 nt. 200–184) |
| PCT primer HP/asp1 | (SEQ ID NO: 17) c | 5'-GTACACTGAC CTAGTGCCGC CCGGGCAAAG CCCGGGCGGC ACTAGGTCAG | |
| PCT primer HP/asp2 | (SEQ ID NO: 18) c | 5'-GTACCTGACC TAGTGCCGCC CGGGCTTTGC CCGGGCGGCA CTAGGTCAGT | |
| PCT primer HP/cla1 | (SEQ ID NO: 19) d | 5'-GTACATTGAC CTAGTGCCGC CCGGGCAAAG CCCGGGCGGC ACTAGGTCAA TCGAT | |
| PCT primer HP/cla2 | (SEQ ID NO: 20) d | 5'-GTACATCGAT TGACCTAGTG CCGCCCGGGC TTTGCCCGGG CGGCACTAGG TCAAT | | a Primers used for PCR amplification of DNA fragments used for generation of constructs described in this patent application.
b PCR primers sets to be used to create the SalI and Asp718 sites juxtaposed to the ITR sequences.
c Synthetic oligonucleotide pair used to generate a synthetic hairpin, recreates an Asp718 site at one of the termini if inserted in Asp718 site.
d Synthetic oligonucleotide pair used to generate a synthetic hairpin, contains the ClaI recognition site to be used for hairpin formation.

Vector pTN was digested with restriction enzymes EcoRI (partially) and ScaI. and the DNA fragment containing the PGK promoter sequences was ligated into PBS.PCRI digested with ScaI and EcoRi. The resulting construct pBS.PGK.PCR1 contains the human PGK promoter operatively linked to Ad5 E1 sequences from nt. 459 to nt. 916.

Construction of pIG.E1A.E1B.X

Figure 2:
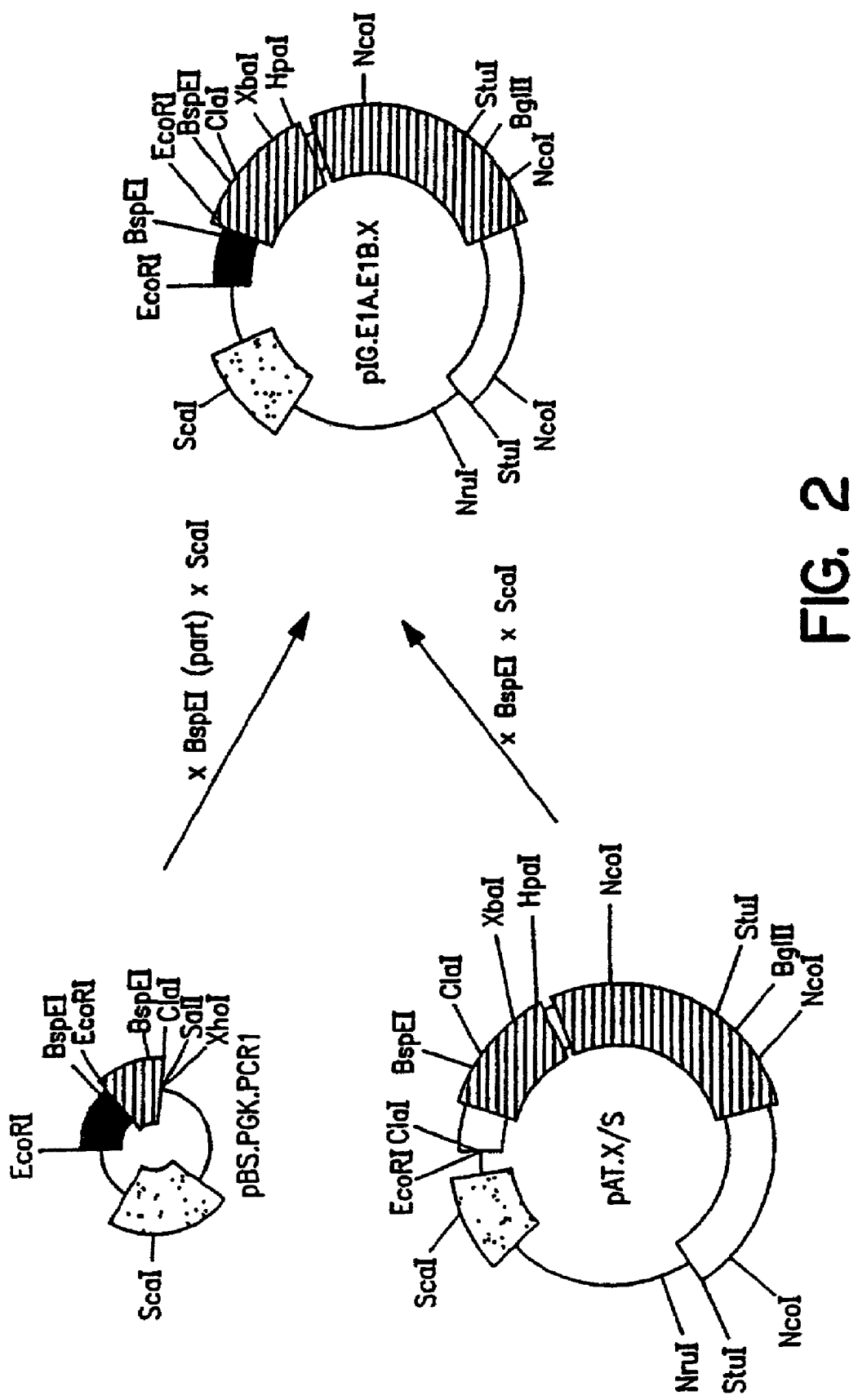
FIG. 2 illustrates the construction of pIG.E1A.E1B.X.

As shown in FIG. 2, pIG.E1A.E1B.X was made by replacing the ScaI-BspEI fragment of pAT.X/S by the corresponding fragment from pBS.PGK.PCR1 (containing the PGK promoter linked to E1A sequences). pIG.E1A.E1B.X contains the E1A and E1B coding sequences under the direction of the PGK promoter. As Ad5 sequences from nt. 459 to nt. 5788 are present in this construct, pIX protein of adenovirus is also encoded by this plasmid.

Construction of pIG.E1A.NEO

Figure 3A:
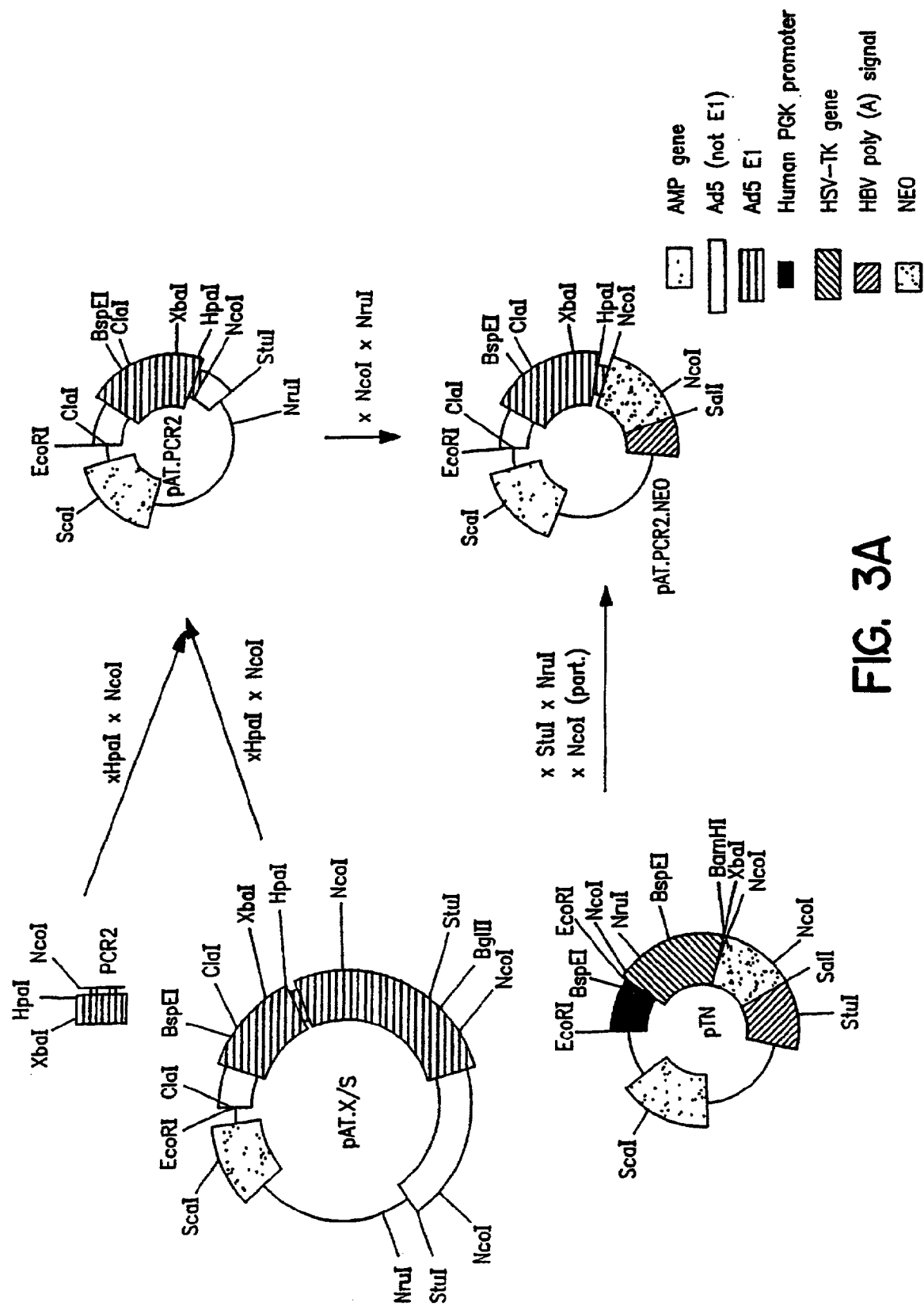
FIGS. 3A and 3B illustrate the construction of pIG.E1A.NEO.

As shown in FIG. 3A, in order to introduce the complete E1B promoter and to fuse this promoter in such a way that the AUG codon of E1B 21 kDa exactly functions as the AUG codon of NEO$^R$, we amplified the E1B promoter using primers Ea-3 (SEQ ID NO:3) and Ep-2 (SEQ ID NO:5), where primer Ep-2 (SEQ ID NO:5) introduces an NcoI site in the PCR fragment. The resulting PCR fragment, named PCRII, was digested with HpaI and NcoI and ligated into pAT-X/S, which was predigested with HpaI and with NcoI. The resulting plasmid was designated pAT.X/S.PCR2. The NcoI-StuI fragment of pTN, containing the NEO gene and part of the HBV poly-adenylation signal, was cloned into pAT.X/S.PCR2 (digested with NcoI and NruI). The resulting construct: pAT.PCR2.NEO.

Figure 3B:
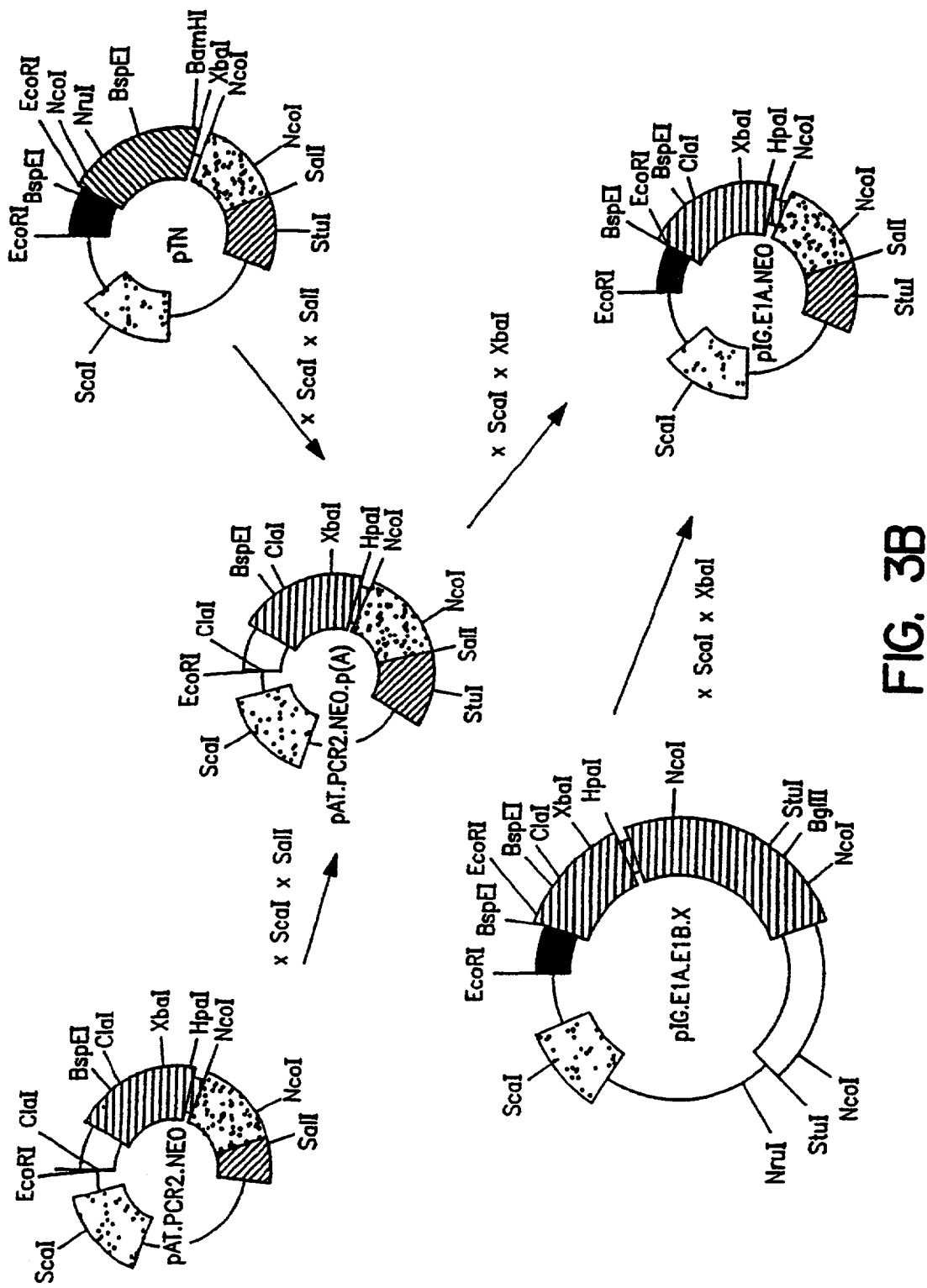

As shown in FIG. 3B, the poly-adenylation signal was completed by replacing the ScaI-SalI fragment of pAT-PCR2-NEO with the corresponding fragment of pTN (resulting in pAT.PCR2.NEO.p(A)). The ScaI-XbaI of pAT.PCR2.NEO.p (A) was replaced by the corresponding fragment of pIG.EIA.E1B-X, containing the PGK promoter linked to E1A genes. The resulting construct was named pIG.E1A.NEO, and thus contains Ad5 E1 sequences (nt. 459 to nt. 1713) under the control of the human PGK promoter.

Construction of pIG.EIA.E1B

Figure 4A:
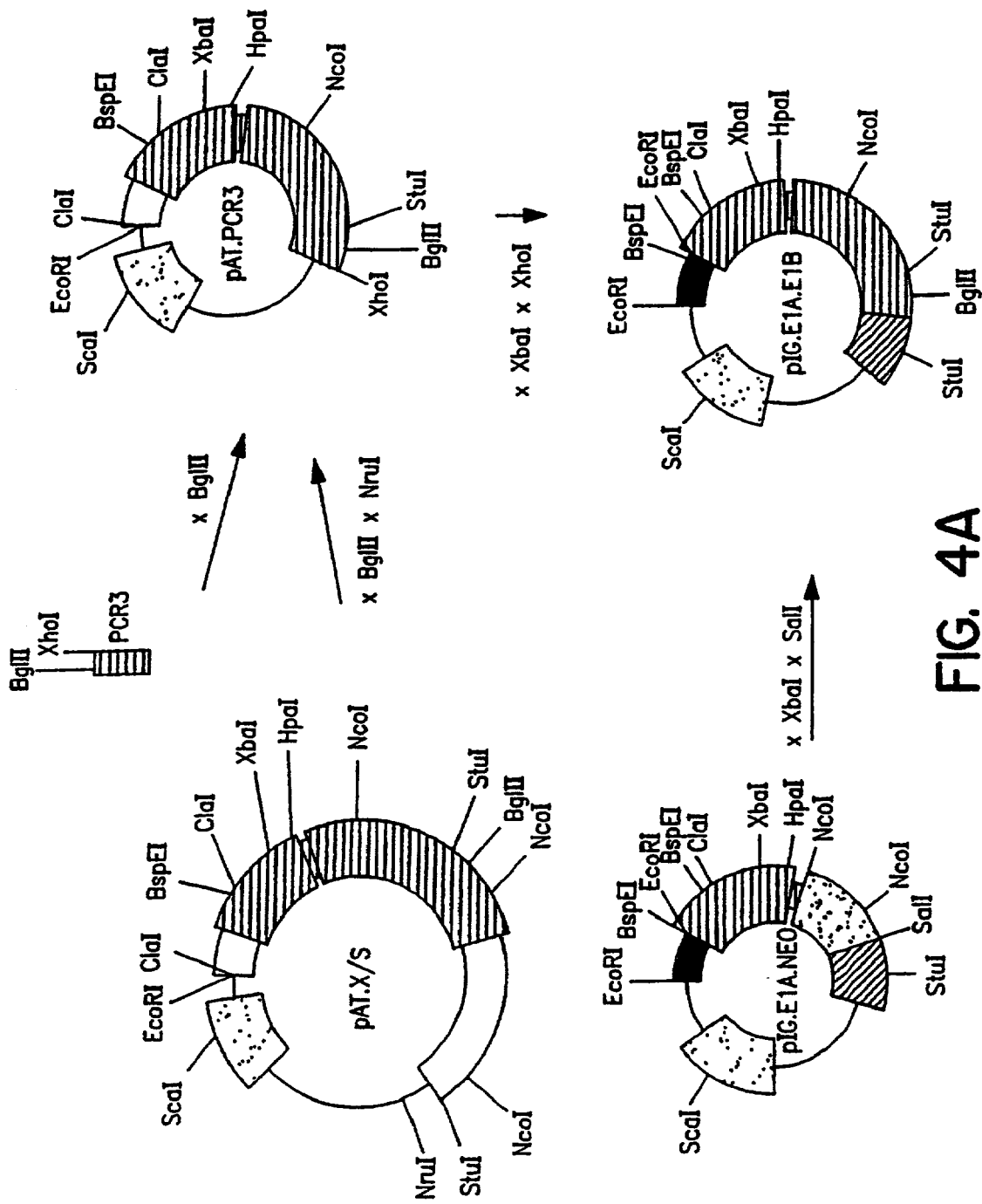
FIG. 4 illustrates the construction of pIG.E1A.E1B.
Figure 4B:
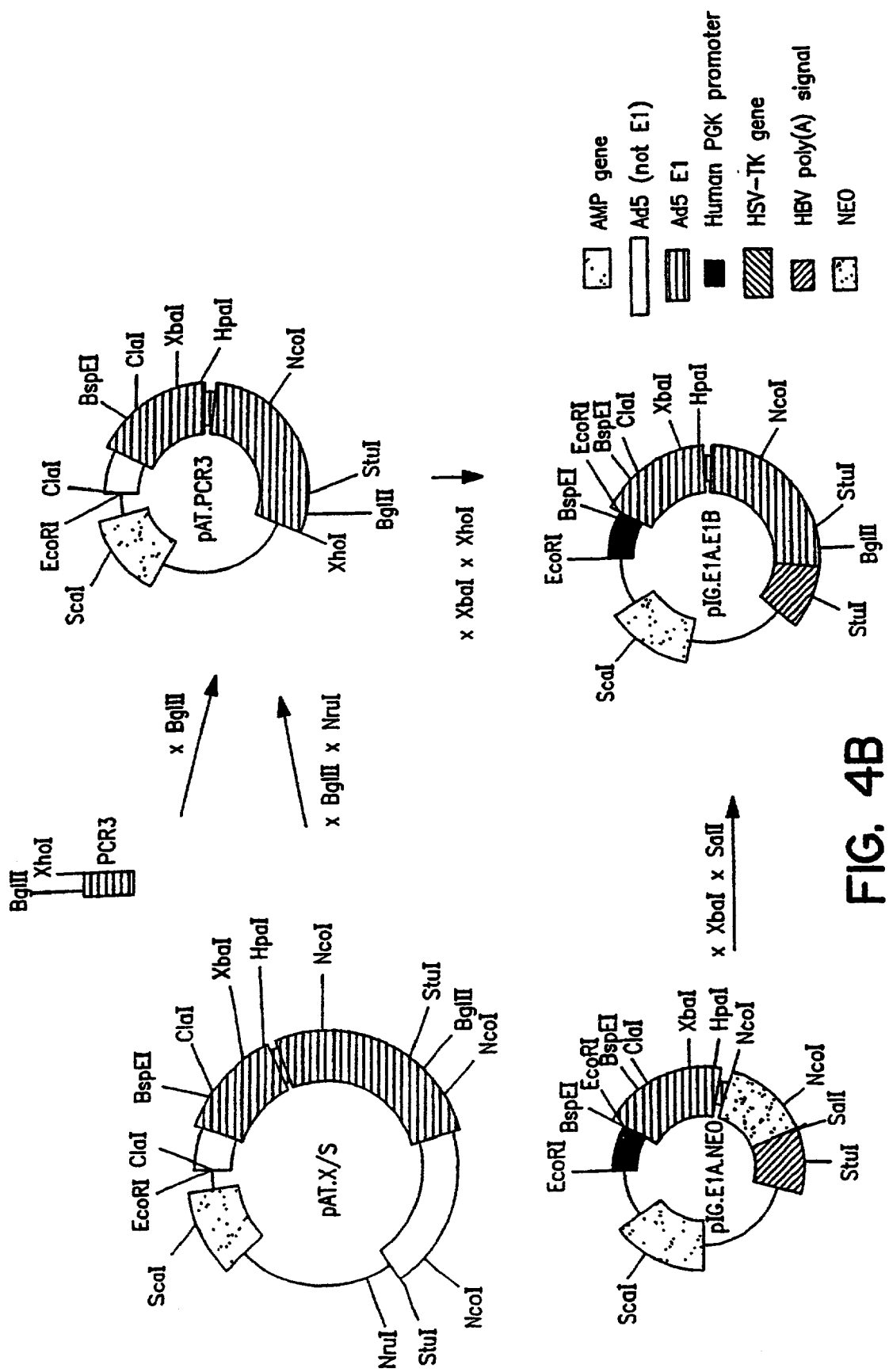

As shown in FIG. 4, pIG.E1A.E1B was made by amplifying the sequences encoding the N-terminal amino acids of E1B 55 kDa using primers Eb-1 (SEQ ID NO:6) and Eb-2 (SEQ ID NO:7) (introduces a XhoI site). The resulting PCR fragment was digested with BglII and cloned into BglII/NruI of pAT-X/S, thereby obtaining pAT.PCR3.

pIG.E1A.E1B was constructed by introducing the HBV poly(A) sequences of pIG.E1A.NEO downstream of E1B sequences of pAT.PCR3 by exchange of XbaI-SalI fragment of pIG.E1A.NEO and the XbaI XhoI fragment of pAT-.PCR3.

pIG.E1A.E1B contains nt. 459 to nt. 3510 of Ad5, which encode the E1A and E1B proteins. The E1B sequences are terminated at the splice acceptor at nt. 3511. No pIX sequences are present in this construct.

Construction of pIG.NEO

Figure 5:
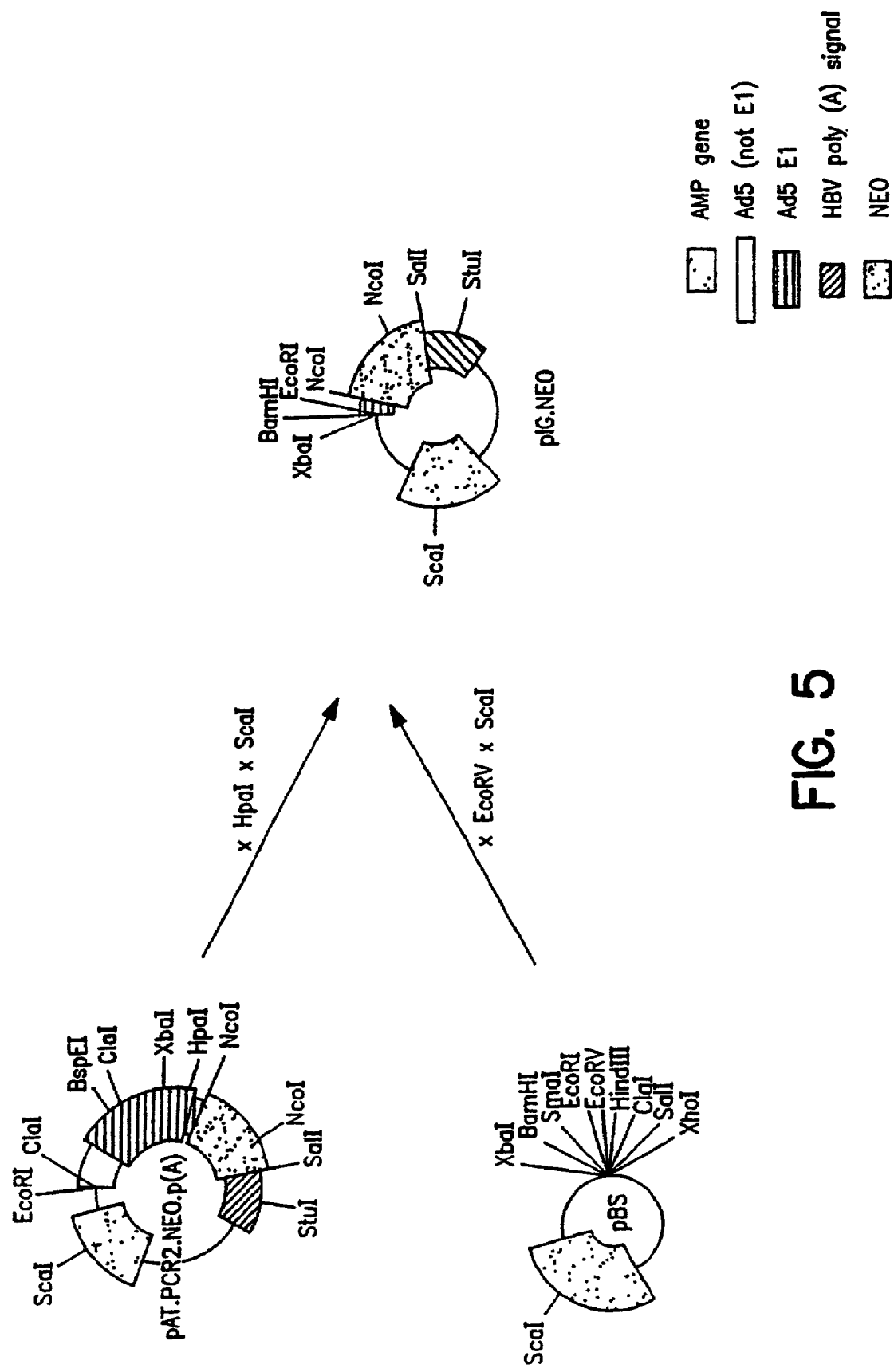
FIG. 5 illustrates the construction of pIG.NEO.

As shown in FIG. 5, pIG.NEO was generated by cloning the HpaI-ScaI fragment of pIG.E1A.NEO, containing the NEO gene under the control of the Ad.5 E1B promoter, into pBS digested with EcoRV and ScaI.

This construct is of use when established cells are transfected with E1A.E1B constructs and NEO selection is required. Because NEO expression is directed by the E1B promoter, NEO resistant cells are expected to co-express E1A, which is also advantageous for maintaining high levels of expression of E1A during long-term culture of the cells.

Testing of Constructs

The integrity of the constructs pIG.E1A.NEO, pIG.E1A.E1B.X and pIG.E1A.E1B was assessed by restriction enzyme mapping; furthermore, parts of the constructs that were obtained by PCR analysis were confirmed by sequence analysis. No changes in the nucleotide sequence were found.

The constructs were transfected into primary Baby Rat Kidney ("BRK") cells and tested for their ability to immortalize (pIG.E1A.NEO) or fully transform (pAd5.XhoIC, pIG.E1A.E1B.X, and pIG.E1A.E1B) these cells.

Kidneys of 6-day old WAG-Rij rats were isolated, homogenized, and trypsinized. Subconfluent dishes (diameter 5 cm) of the BRK cell cultures were transfected with 1 or 5 µg of pIG.NEO, pIG.E1A.NEO, pIG.E1A.E1B, pIG.E1A.E1B.X, pAd5XhoIC, or pIG.E1A.NEO together with PDC26 (Van der El sen et al., 1983), carrying the Ad5.E1B gene under control of the SV40 early promoter. Three weeks post-transfection, when foci were visible, the dishes were fixed, Giemsa stained, and the foci counted.

Figure 6:
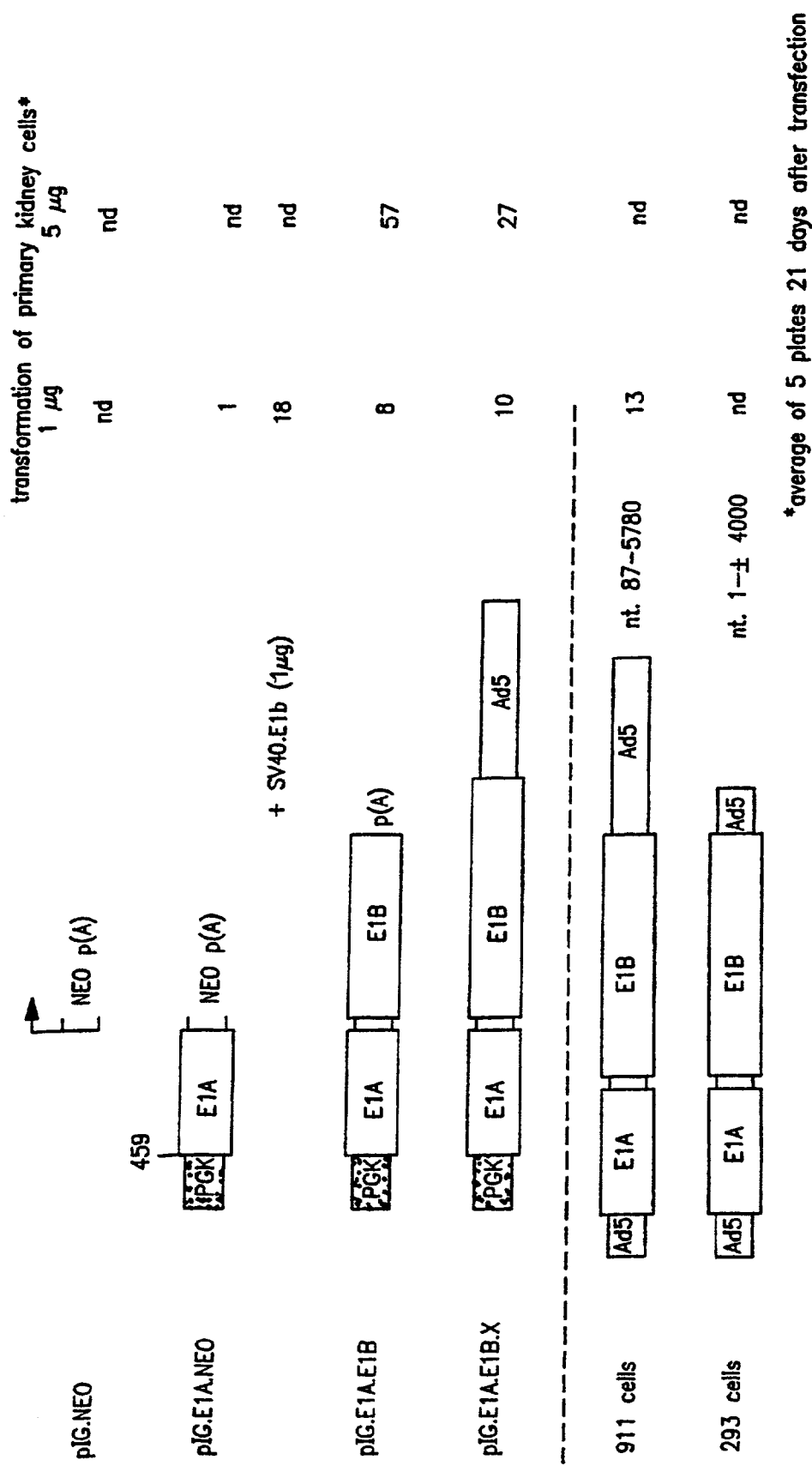
FIG. 6 illustrates the transformation of primary baby rat kidney ("BRK") cells by adenovirus packaging constructs.

An overview of the generated adenovirus packaging constructs and their ability to transform BRK is presented in FIG. 6. The results indicate that the constructs pIG.E1A.E1B and pIG.E1A.E1B.X are able to transform BRK cells in a dose-dependent manner. The efficiency of transformation is similar for both constructs and is comparable to what was found with the construct that was used to make 911 cells, namely pAd5. XhoIC.

As expected, pIG.E1A.NEO was hardly able to immortalize BRK. However, co-transfection of an E1B expression construct (PDC26) did result in a significant increase in the number of transformants (18 versus 1), indicating that E1A encoded by pIG.E1A.NEO is functional. We conclude, therefore, that the newly generated packaging constructs are suited for the generation of new adenovirus packaging lines.

Generation of Cell Lines with New Packaging Constructs, Cell Lines, and Cell Culture Human A549 bronchial carcinoma cells (Shapiro et al., 1978), human embryonic retinoblasts ("HER"), Ad5-E1-transformed human embryonic kidney ("HEK") cells (293; Graham et al., 1977), and Ad5-transformed HER cells (911; Fallaux et al., 1996)) and PER cells were grown in Dulbecco's Modified Eagle Medium ("DMEM") supplemented with 10% Fetal Calf Serum ("FCS") and antibiotics in a 5% $CO_2$ atmosphere at 37° C. Cell culture media, reagents, and sera were purchased from Gibco Laboratories (Grand Island, N.Y.). Culture plastics were purchased from Greiner (Nürtingen, Germany) and Coming (Coming, N.Y.).

Viruses and Virus Techniques

The construction of adenoviral vectors IG.Ad.MLP.nls.lacZ, IG.Ad.MLP.luc, IG.Ad.MLP.TK, and IG.Ad.CMV.TK is described in detail in European patent application EP 95202213. The recombinant adenoviral vector IG.Ad.MLP.nls.lacZ contains the *E. coli* lacZ gene, encoding β-galactosidase, under control of the Ad2 major late promoter ("MLP"). IG.Ad.MLP.luc contains the firefly luciferase gene driven by the Ad2 MLP. Adenoviral vectors IG.Ad.MLP.TK and IG.Ad.CMV.TR contain the Herpes Simplex Virus thymidine kinase ("TK") gene under the control of the Ad2 MLP and the Cytomegalovirus ("CMV") enhancer/promoter, respectively.

Transfections

All transfections were performed by calcium-phosphate precipitation DNA (Graham and Van der Eb, 1973) with the GIBCO Calcium Phosphate Transfection System (GIBCO BRL Life Technologies Inc., Gaithersburg, Md., USA), according to the manufacturer's protocol.

Western Blotting

Subconfluent cultures of exponentially growing 293, 911 and Ad5-E1-transformed A549 and PER cells were washed with PBS and scraped in Fos-RIPA buffer (10 mM Tris (pH 7.5), 150 mM NaCl, 1% NP4O,01% sodium dodecyl sulphate ("SDS"), 1% NA-DOC, 0.5 mM phenyl methyl sulphonyl fluoride ("PMSF"), 0.5 mM trypsin inhibitor, 50 mM NaF and 1 mM sodium vanadate). After 10 minutes at room temperature, lysates were cleared by centrifugation. Protein concentrations were measured with the Biorad protein assay kit, and 25 µg total cellular protein was loaded on a 12.5% SDS-PAA gel. After electrophoresis, proteins were transferred to nitrocellulose (1 hour at 300 mA). Prestained standards (Sigma, USA) were run in parallel. Filters were blocked with 1% bovine serum albumin ("BSA") in TBST (10 mM Tris, pH 8.15 mM NaCl, and 0.05% TWEEN™-20) for 1 hour. First antibodies were the mouse monoclonal anti-Ad5-E1B-55-kDa antibody A1C6 (Zantema et al., unpublished), the rat monoclonal anti-Ad5-E1B-221-kDa antibody C1G11 (Zantema et al., 1985). The second antibody was a horseradish peroxidase-labeled goat anti-mouse antibody (Promega). Signals were visualized by enhanced chemiluminescence (Amersham Corp, UK).

Southern Blot Analysis

High molecular weight DNA was isolated and 10 µg was digested to completion and fractionated on a 0.7% agarose gel. Southern blot transfer to Hybond N+(Amersham, UK) was performed with a 0.4 M NaOH, 0.6 M NaCl transfer solution (Church and Gilbert, 1984). Hybridization was performed with a 2463-nt SspI-HindIII fragment from pAd5.SalB (Bernards et al., 1983). This fragment consists of Ad5 bp. 342–2805. The fragment was radiolabeled with $\alpha$-$^{32}$P-dCTP with the use of random hexanucleotide primers and Klenow DNA polymerase. The Southern blots were exposed to a Kodak XAR-5 film at −80° C. and to a Phospho-Imager screen that was analyzed by B&L Systems' Molecular Dynamics software.

A549

Ad5-E1-transformed A549 human bronchial carcinoma cell lines were generated by transfection with pIG.E1A.NEO and selection for G418 resistance. Thirty-one G418 resistant clones were established. Co-transfection of pIG.E1A.E1B with pIG.NEO yielded seven G418 resistant cell lines.

PER

Ad5-E1-transformed HER cells were generated by transfection of primary HER cells with plasmid pIG.E1A.E1B. Transformed cell lines were established from well-separated foci. We were able to establish seven clonal cell lines, which we called PER.C1, PER.C3, PER.C4, PER.C5, PER.C6™, PER.C8, and PER.C9. One of the PER clones, namely PER.C6™, has been deposited under the Budapest Treaty under number ECACC™ 96022940 with the Centre for Applied Microbiology and Research of Porton Down, UK, on Feb. 29, 1996. In addition, PER.C6™ is commercially available from IngroGene, B. V., Leiden, NL.

Expression of Ad5 E1A and E1B Genes in Transformed A549 and PER Cells

Expression of the Ad5 E1A and the 55 kDa and 21 kDa E1B proteins in the established A549 and PER cells was studied by means of Western blotting with the use of monoclonal antibodies ("Mab"). Mab M73 recognizes the E1A products, whereas Mabs AIC6 and C1G11 are directed against the 55 kDa and 21 kDa E1B proteins, respectively.

Figure 7:
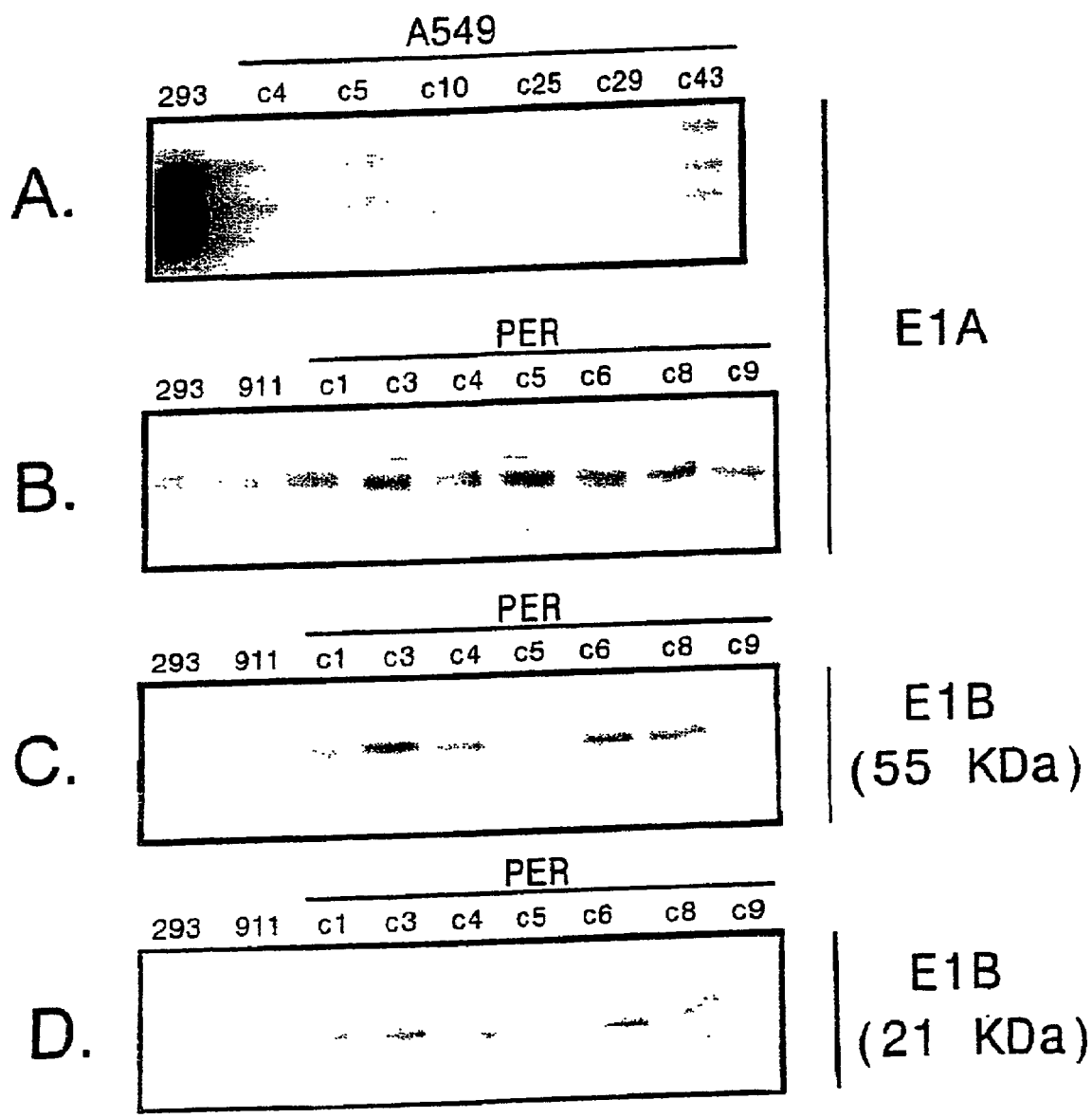
FIG. 7 illustrates a Western blot analysis of A549 clones transfected with pIG.E1A.NEO and HER cells transfected with pIG.E1A.E1B (PER clones)

The antibodies did not recognize proteins in extracts from the parental A549 or the primary HER cells (data not shown). None of the A549 clones that were generated by co-transfection of pIG.NEO and pIG.E1A.E1B expressed detectable levels of E1A or E1B proteins (not shown). Some of the A549 clones that were generated by transfection with pIG.E1A.NEO expressed the Ad5 E1A proteins (see FIG. 7), but the levels were much lower than those detected in protein lysates from 293 cells. The steady state E1A levels detected in protein extracts from PER cells were much higher than those detected in extracts from A549-derived cells. All PER cell lines expressed similar levels of E1A proteins (FIG. 7). The expression of the E1B proteins, particularly in the case of E1B 55 kDa, was more variable. Compared to 911 and 293, the majority of the PER clones express high levels of E1B 55 kDa and 21 kDa. The steady state level of E1B 21 kDa was the highest in PER.C3. None of the PER clones lost expression of the Ad5 E1 genes upon serial passage of the cells (not shown). We found that the level of E1 expression in PER cells remained stable for at least 100 population doublings. We decided to characterize the PER clones in more detail.

Southern Analysis of PER Clones

Figure 8:
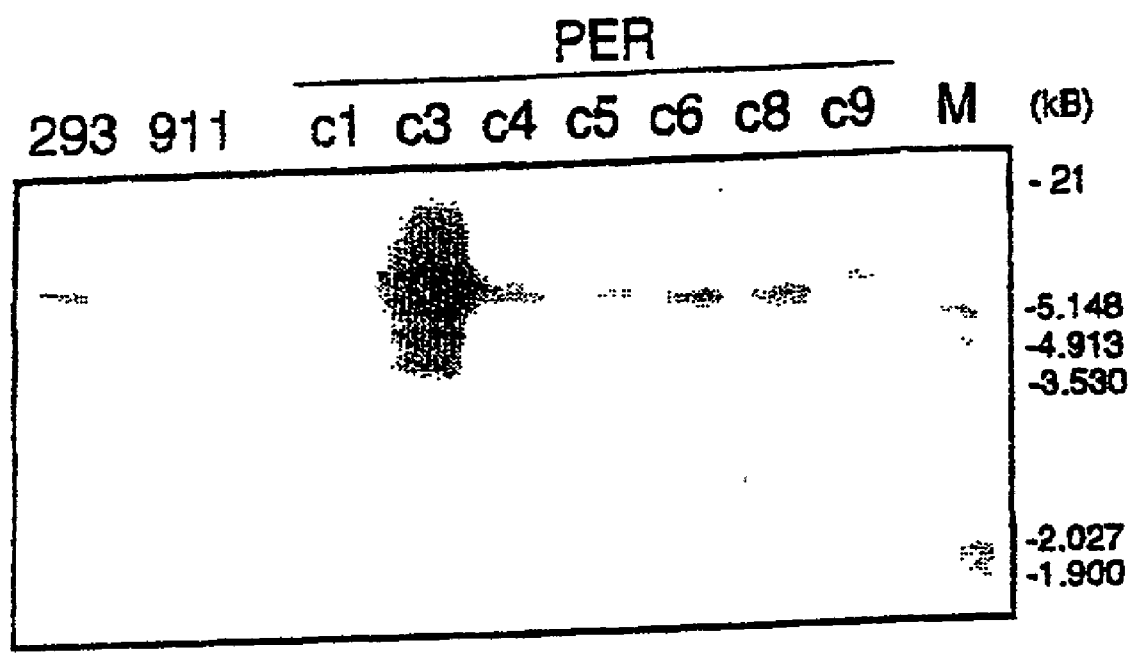
FIG. 8 illustrates a Southern blot analysis of 293, 911 and PER cell lines. Cellular DNA was extracted, Hind III digested, electrophoresed and transferred to Hybond N+ membranes (Amersham)

To study the arrangement of the Ad5-E1 encoding sequences in the PER clones, we performed Southern analyses. Cellular DNA was extracted from all PER clones and from 293 and 911 cells. The DNA was digested with HindIII, which cuts once in the Ad5 E1 region. Southern hybridization on HindIII-digested DNA, using a radiolabeled Ad5-E1-specific probe, revealed the presence of several integrated copies of pIG.E1A.E1B in the genome of the PER clones. FIG. 8 shows the distribution pattern of E1 sequences in the high molecular weight DNA of the different PER cell lines. The copies are concentrated in a single band, which suggests that they are integrated as tandem repeats. In the case of PER.C3, C5, C6, and C9, we found additional hybridizing bands of low molecular weight that indicate the presence of truncated copies of pIG.E1A.E1B. The number of copies was determined with the use of a Phospho-Imager. We estimated that PER.C1, C3, C4, C5, C6, C8, and C9 contain 2, 88, 5, 4, 5, 5, and 3 copies of the Ad5 E1 coding region, respectively, and that 911 and 293 cells contain 1 and 4 copies of the Ad5 E1 sequences, respectively.

Transfection Efficiency

Figure 9:
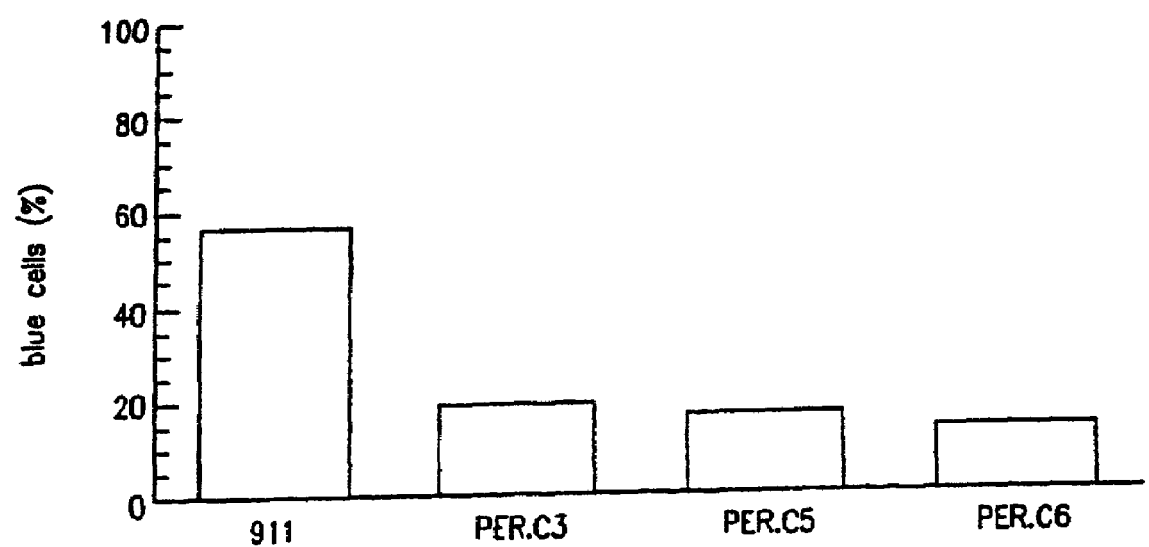
FIG. 9 illustrates the transfection efficiency of PER.C3, PER.C5, PER.C6™ and 911 cells.

Recombinant adenovectors are generated by co-transfection of adaptor plasmids and the large ClaI fragment of Ad5 into 293 cells (see European patent application EP 95202213). The recombinant virus DNA is formed by homologous recombination between the homologous viral sequences that are present in the plasmid and the adenovirus DNA. The efficacy of this method, as well as that of alternative strategies, is highly dependent on the transfectability of the helper cells. Therefore, we compared the transfection efficiencies of some of the PER clones with 911 cells, using the *E. coli* β-galactosidase-encoding lacZ gene as a reporter (see FIG. 9).

Production of Recombinant Adenovirus

Yields of recombinant adenovirus obtained after inoculation of 293, 911, PER.C3, PER.C5, and PER.C6™ with different adenovirus vectors are presented in Table II. The results indicate that the yields obtained on PER cells are at least as high as those obtained on the existing cell lines. In addition, the yields of the novel adenovirus vector IG.Ad-.MLPI.TK are similar or higher than the yields obtained for the other viral vectors on all cell lines tested.

TABLE II

| Cell | Passage number | IG.Ad.CMV.-lacZ | IG.Ad.CMV.-TK | IG.Ad.MLPI.TK | d1313 | Producer Mean |
|---|---|---|---|---|---|---|
| 293 |  | 6.0 | 5.8 | 24 | 34 | 17.5 |
| 911 |  | 8 | 14 | 34 | 180 | 59.5 |
| PER.C3 | 17 | 8 | 11 | 44 | 40 | 25.8 |
| PER.C5 | 15 | 6 | 17 | 36 | 200 | 64.7 |
| PER.C6 ™ | 36 | 10 | 22 | 58 | 320 | 102 |

Yields × $10^{-8}$ pfu/T175 flask.

Table II. Yields of different recombinant adenoviruses obtained after inoculation of adenovirus E1 packaging cell lines 293, 911, PER.C3, PER.C5, and PER.C6™. The yields are the mean of two different experiments. IG.Ad.CMV.lacZ and IG.Ad.CMV.TK are described in European patent application EP 95202213. The construction of IG.Ad.MLPI.TK is described in this patent application. Yields of virus per T80 flask were determined by plaque assay on 911 cells, as described [Fallaux, 1996 #1493].

Generation of New Adenovirus Vectors

The used recombinant adenovirus vectors (see European patent application EP 95202213) are deleted for E1 sequences from nt. 459 to nt. 3328.

Figure 10:
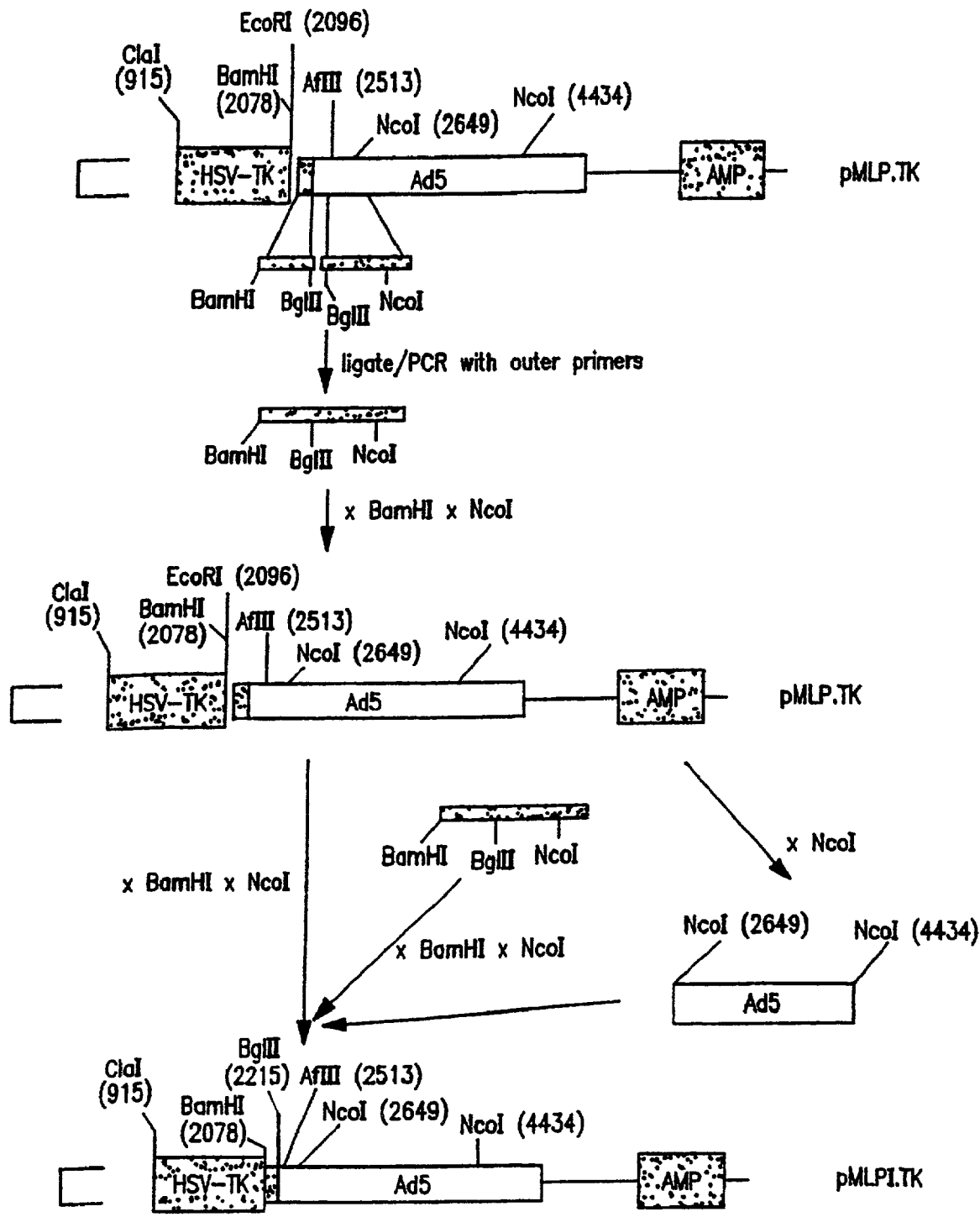
FIG. 10 illustrates construction of adenovirus vector pMLPI.TK. pMLPI.TK designed to have no sequence overlap with the packaging construct pIG.E1A.E1B.

As construct pE1A.E1B contains Ad5 sequences nt. 459 to nt. 3510, there is a sequence overlap of 183 nt. between E1B sequences in the packaging construct pIG.E1A.E1B and recombinant adenoviruses, such as, for example, IG.Ad-.MLP.TK. The overlapping sequences were deleted from the new adenovirus vectors. In addition, non-coding sequences derived from lacZ, which are present in the original constructs, were deleted as well. This was achieved (see FIG. 10) by PCR amplification of the SV40 poly(A) sequences from pMLP.TK using primers SV40-1 (SEQ ID NO:8) (introduces a BamHI site) and SV40-2 (SEQ ID NO:9) (introduces a BglII site). In addition, Ad5 sequences present in this construct were amplified from nt. 2496 (Ad5-1 (SEQ ID NO:10), introduces a BglII site) to nt. 2779 (Ad5-2 (SEQ ID NO:11)). Both PCR fragments were digested with BglII and were ligated. The ligation product was PCR amplified using primers SV40-1 (SEQ ID NO:8) and Ad5-2 (SEQ ID NO:11). The PCR product obtained was cut with BamHI and AflII and was ligated into pMLP.TK predigested with the same enzymes. The resulting construct, named pMLPI.TK, contains a deletion in adenovirus E1 sequences from nt. 459 to nt. 3510.

Packaging System

The combination of the new packaging construct pIG.E1A.E1B and the recombinant adenovirus pMLPI.TK, which do not have any sequence overlap, are presented in FIGS. 11A and 11B. In these figures, the original situation is also presented with the sequence overlap indicated.

The absence of overlapping sequences between pIG.E1A.E1B and pMLPI.TK (FIG. 11A) excludes the possibility of homologous recombination between packaging construct and recombinant virus, and is therefore a significant improvement for production of recombinant adenovirus as compared to the original situation.

In FIG. 11B, the situation is depicted for pIG.E1A.NEO and IG.Ad.MLPI.TK. pIG.E1A.NEO, when transfected into established cells, is expected to be sufficient to support propagation of E1-deleted recombinant adenovirus. This combination does not have any sequence overlap, preventing generation of RCA by homologous recombination. In addition, this convenient packaging system allows the propagation of recombinant adenoviruses that are deleted just for E1A sequences and not for E1B sequences. Recombinant adenoviruses expressing E1B in the absence of E1A are attractive, as the E1B protein, in particular E1B 19 kDa, is able to prevent infected human cells from lysis by Tumor Necrosis Factor ("TNF") (Gooding et al., 1991).

Generation of Recombinant Adenovirus Derived From pMLPI.TK.

Figure 12:
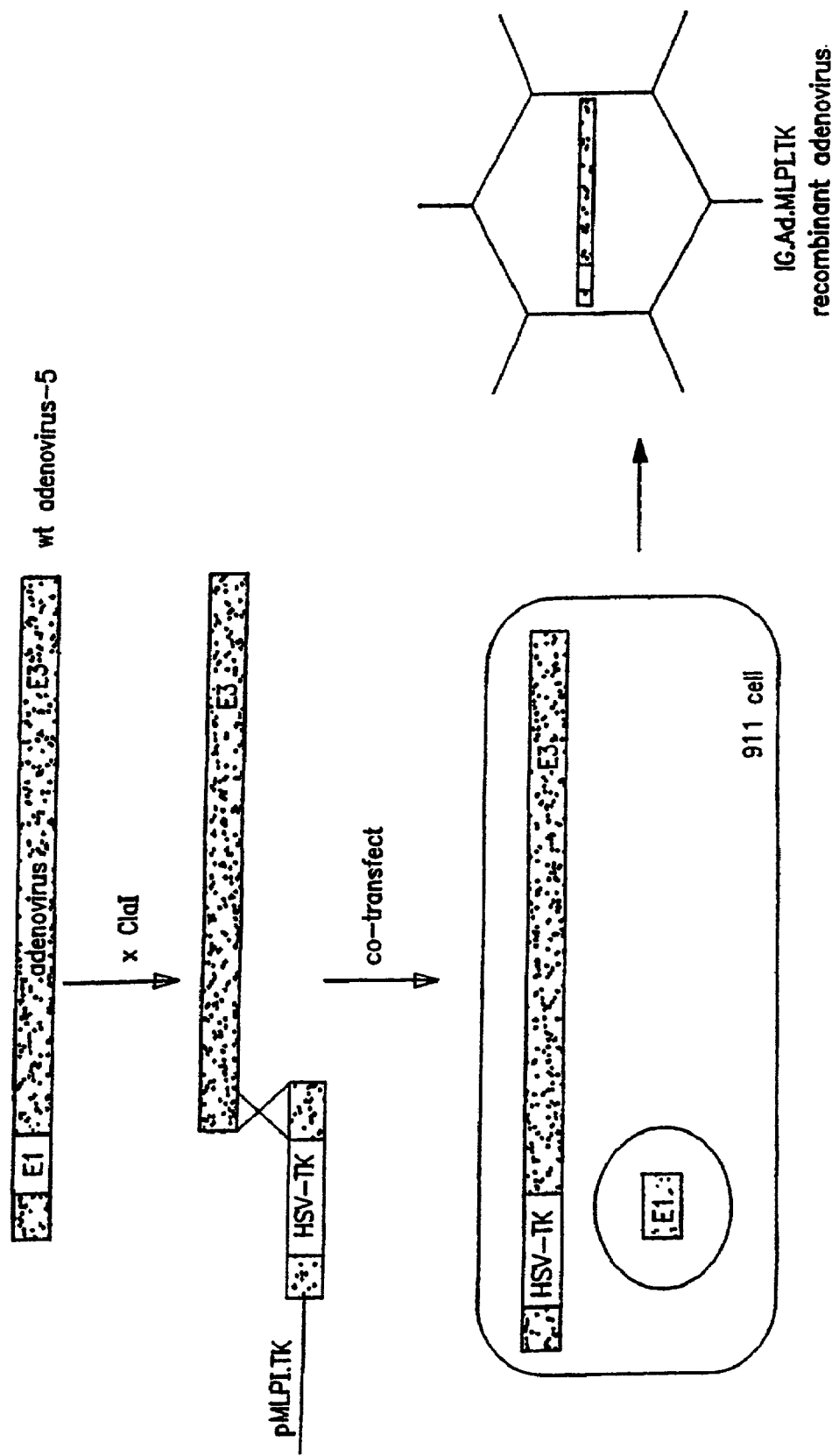
FIG. 12 illustrate the generation of recombinant adenovirus IG.Ad.MLPI.TK.

Recombinant adenovirus was generated by co-transfection of 293 cells with SalI linearized pMLPI.TK DNA and ClaI linearized Ad5 wt DNA. The procedure is schematically represented in FIG. 12.

Outline of the Strategy to Generate Packaging Systems for Minimal Adenovirus Vector Name convention of the plasmids used:
p plasmid
I ITR (Adenovirus Inverted Terminal Repeat)
C CMV Enhancer/Promoter Combination
L Firefly Luciferase Coding Sequence hac,haw Potential hairpin that can be formed after digestion with restriction endonuclease Asp718 in its correct and in the reverse orientation, respectively (FIG. 15 (SEQ ID NO:22)).

For example, pICLhaw is a plasmid that contains the adenovirus ITR followed by the CMV-driven luciferase gene and the Asp718 hairpin in the reverse (non-functional) orientation.

Experiment Series 1

The following demonstrates the competence of a synthetic DNA sequence that is capable of forming a hairpin-structure to serve as a primer for reverse strand synthesis for the generation of double-stranded DNA molecules in cells that contain and express adenovirus genes.

Plasmids pICLhac, pICLhaw, pICLI and pICL (SEQ ID NO:21) were generated using standard techniques. The schematic representation of these plasmids is shown in FIGS. 16–19.

Plasmid pICL (SEQ ID NO:21) is derived from the following plasmids:
nt.1–457 pMLP10 (Levrero et al., 1991);
nt.458–1218 pCMVβ (Clontech, EMBL Bank No. U02451);
nt.1219–3016 pMLP.luc (IntroGene, Leiden, NL, unpublished); and
nt.3017–5620 pBLCAT5 (Stein and Whelan, 1989).

Figure 19:
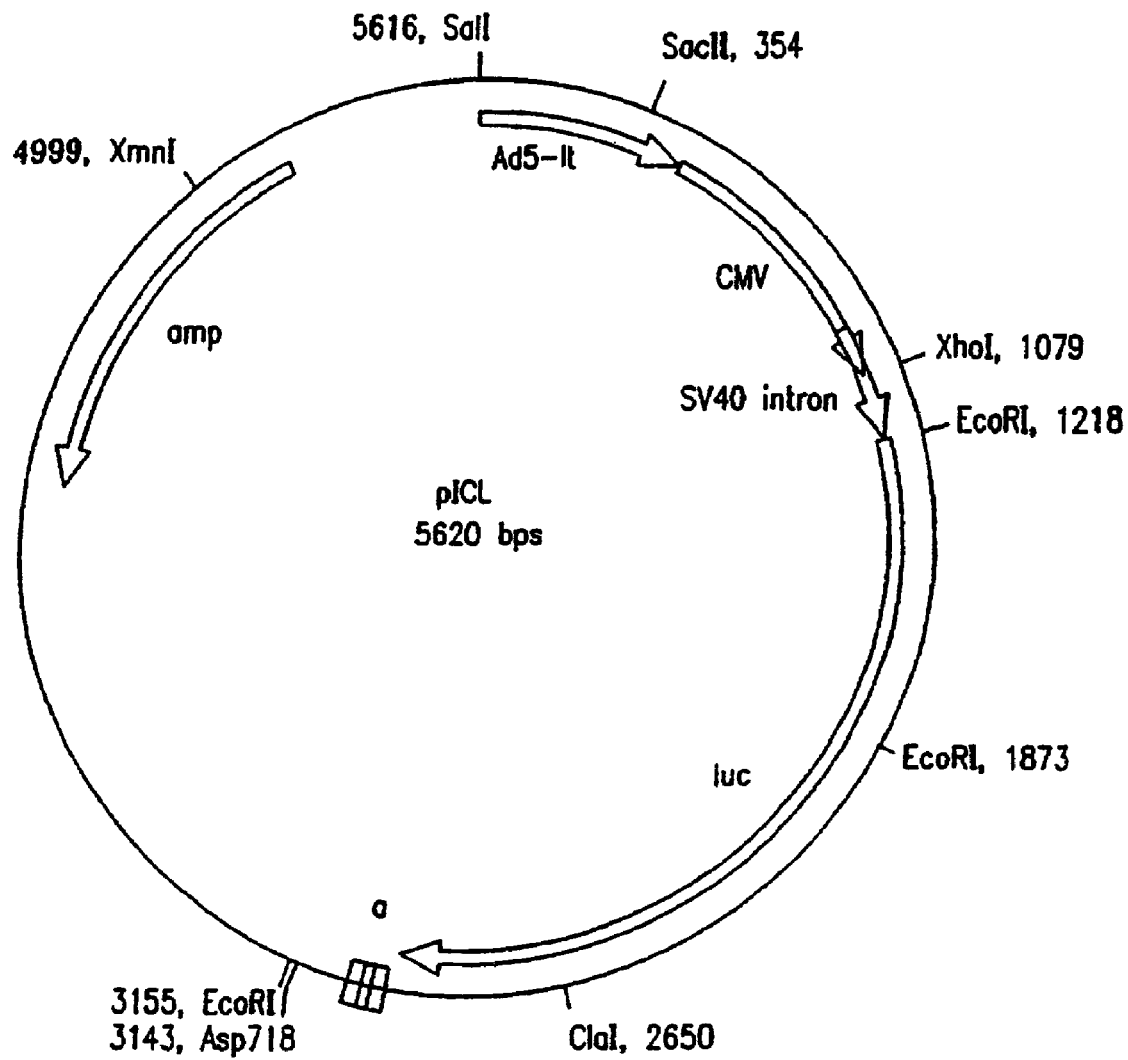
FIG. 19 is a diagram of pICL (SEQ ID NO:21)

The Plasmid has been Constructed as Follows:

The tet gene of plasmid pMLP10 has been inactivated by deletion of the BamHI-SalI fragment to generate pMLP10ΔSB. Using primer set PCR/MLP1 (SEQ ID NO:14) and PCR/MLP3 (SEQ ID NO:16), a 210 bp fragment containing the Ad5-ITR, flanked by a synthetic SalI restriction site, was amplified using pMLP10 DNA as the template. The PCR product was digested with the enzymes EcoRI and SgrAI to generate a 196 bp fragment. Plasmid pMLP10ΔSB was digested with EcoRI and SgrAI to remove the ITR. This fragment was replaced by the EcoRI-SgrAI-treated PCR fragment to generate pMLP/SAL. Plasmid pCMV-Luc was digested with PvuII to completion and recirculated to remove the SV40-derived poly-adenylation signal and Ad5 sequences with exception of the Ad5 left-terminus. In the resulting plasmid, pCMV-lucΔAd, the Ad5 ITR was replaced by the Sal-site-flanked ITR from plasmid pMLP/SAL by exchanging the XmnI-SacII fragments. The resulting plasmid, pCMV-lucΔAd/SAL, the Ad5 left terminus, and the CMV-driven luciferase gene were isolated as an SalI-SmaI fragment and inserted in the SalI and HpaI digested plasmid pBLCATS to form plasmid pICL (SEQ ID NO:21). Plasmid pICL is represented in FIG. 19; its sequence is presented in FIGS. 20A–20F (SEQ ID NO:21).

The plasmid pICL (SEQ ID NO:21) contains the following features:

nt. 1–457 Ad5 left terminus (Sequence 1–457 of human adenovirus type 5);
nt. 458–969 Human cytomegalovirus enhancer and immediate early promoter (see Boshart et al., A Very Strong Enhancer is Located Upstream of an Immediate Early Gene of Human Cytomegalovirus", *Cell* 41, pp. 521–530 (1985), hereby incorporated herein by reference) (from plasmid pCMVβ, Clontech, Palo Alto, USA);
nt. 970–1204 SV40 19S exon and truncated 16/19S intron (from plasmid pCMVβ);
nt. 1218–2987 Firefly luciferase gene (from pMLP.luc);
nt. 3018–3131 SV40 tandem poly-adenylation signals from late transcript, derived from plasmid pBLCAT5;
nt. 3132–5620 pUC12 backbone (derived from plasmid pBLCAT5); and
nt. 4337–5191 β-lactamase gene (Amp-resistance gene, reverse orientation).

Plasmid pICLhac and pICLhaw

Plasmids pICLhac and pICLhaw were derived from plasmid pICL (SEQ ID NO:21) by digestion of the latter plasmid with the restriction enzyme Asp718. The linearized plasmid was treated with Calf-Intestine Alkaline Phosphatase to remove the 51 phosphate groups. The partially complementary synthetic single-stranded oligonucleotide Hp/asp1 (SEQ ID NO:17) and Hp/asp2 (SEQ ID NO:18) were annealed and phosphorylated on their 5' ends using T4-polynucleotide kinase.

Figure 16:
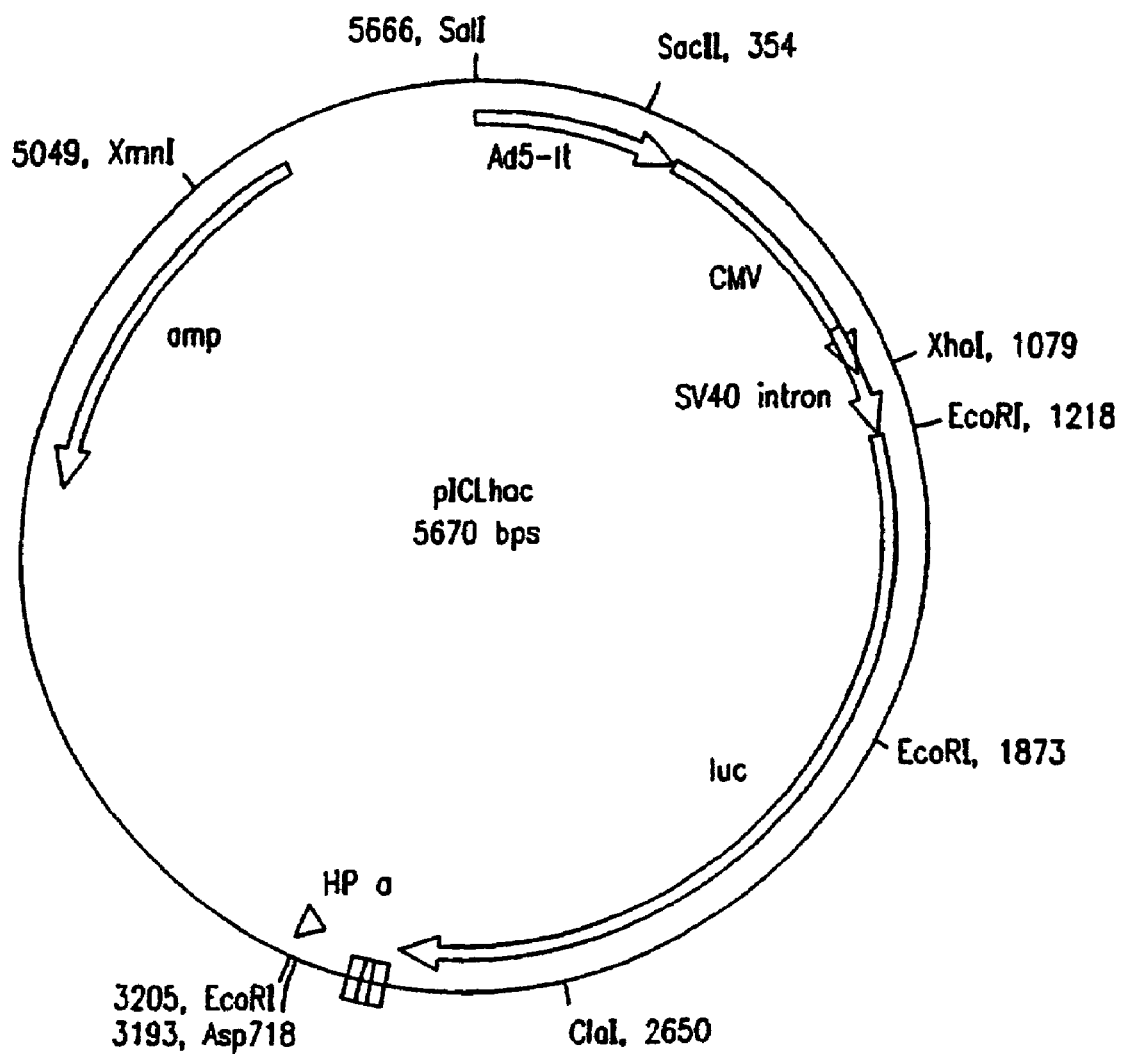
FIG. 16 illustrates a diagram of pICLhac.
Figure 17:
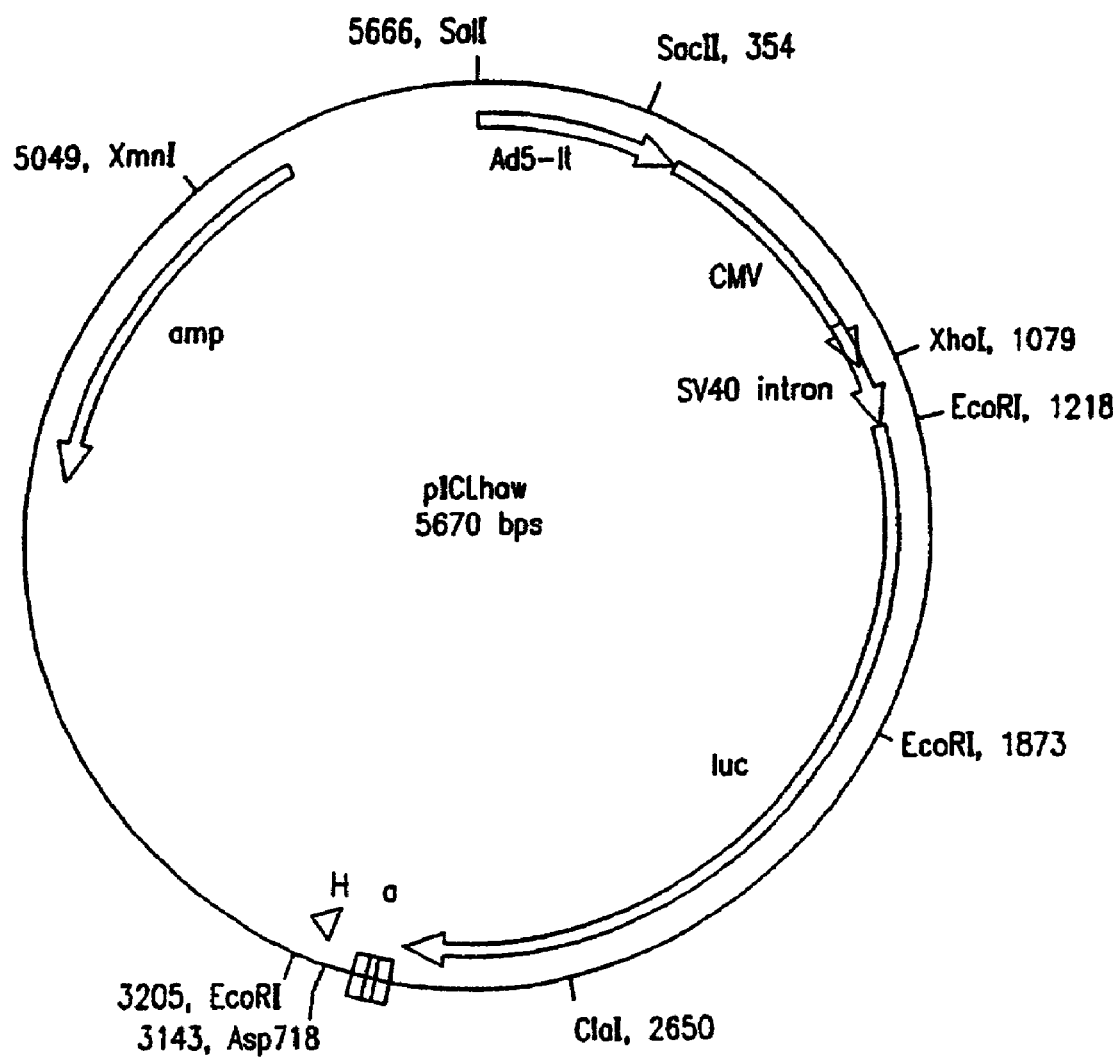
FIG. 17 illustrates a diagram of pICLhaw.
Figure 18:
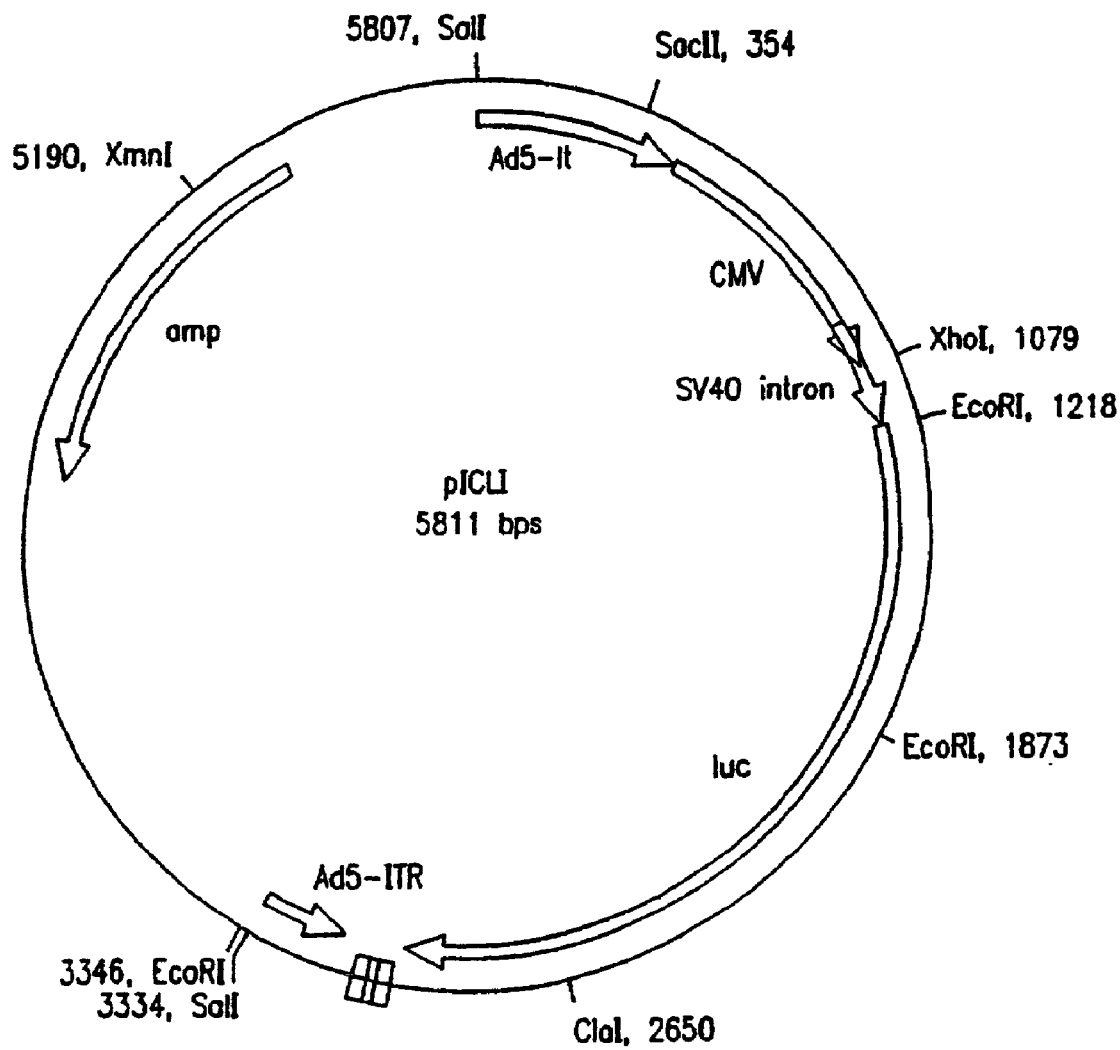
FIG. 18 illustrates a schematic representation of pICLI.

The phosporylated double-stranded oligomers were mixed with the dephosporylated pICL fragment and ligated. Clones containing a single copy of the synthetic oligonucleotide inserted into the plasmid were isolated and characterized using restriction enzyme digests. Insertion of the oligonucleotide into the Asp718 site will at one junction recreate an Asp718 recognition site, whereas at the other junction, the recognition site will be disrupted. The orientation and the integrity of the inserted oligonucleotide were verified in selected clones by sequence analyses. A clone containing the oligonucleotide in the correct orientation (the Asp718 site close to the 3205 EcoRI site) was denoted pICLhac. A clone with the oligonucleotide in the reverse orientation (the Asp718 site close to the SV40 derived poly signal) was designated pICLhaw. Plasmids pICLhac and pICLhaw are represented in FIGS. 16 and 17.

Plasmid pICLI was created from plasmid pICL (SEQ ID NO:21) by insertion of the SalI-SgrAI fragment from pICL containing the Ad5-ITR into the Asp718 site of pICL. The 194 bp SalI-SgrAI fragment was isolated from pICL (SEQ ID NO:21), and the cohesive ends were converted to blunt ends using *E. coli* DNA polymerase I (Klenow fragment) and dNTPs. The Asp718 cohesive ends were converted to blunt ends by treatment with mungbean nuclease. Clones were generated by ligation that contain the ITR in the Asp718 site of plasmid pICL (SEQ ID NO:21). A clone that contained the ITR fragment in the correct orientation was designated pICLI (see FIG. 18). Generation of adenovirus Ad-CMV-hcTK: recombinant adenovirus was constructed according to the method described in European patent application EP 95202213. Two components are required to generate a recombinant adenovirus. First, an adaptor-plasmid containing the left terminus of the adenovirus genome containing the ITR and the packaging signal, an expression cassette with the gene of interest, and a portion of the adenovirus genome which can be used for homologous recombination. In addition, adenovirus DNA is needed for recombination with the aforementioned adaptor plasmid. In the case of Ad-CMV-hcTK, the plasmid PCMV.TK was used as a basis. This plasmid contains nt. 1–455 of the adenovirus type 5 genome, nt. 456–1204 derived from pCMVβ (Clontech, the PstI-StuI fragment that contains the CMV enhancer promoter and the 16S/19S intron from Simian Virus 40), the HSV TK gene (described in European patent application EP 95202213), the SV40-derived polyadenylation signal (nt 2533–2668 of the SV40 sequence), followed by the BglII-ScaI fragment of Ad5 (nt. 3328–6092 of the Ad5 sequence). These fragments are present in a pMLP10-derived (Levrero et al., 1991) backbone. To generate plasmid pAD-CMVhc-TK, plasmid pCMV.TK was digested with ClaI (the unique ClaI-site is located just upstream of the TK open reading frame) and dephosphorylated with Calf-Intestine Alkaline Phosphate. To generate a hairpin-structure, the synthetic oligonucleotides HP/cla1 (SEQ ID NO:19) and HP/cla2 (SEQ ID NO:20) were annealed and phosphorylated on their 5-OH groups with T4-polynucleotide kinase and ATP. The double-stranded oligonucleotide was ligated with the linearized vector fragment and used to transform *E. coli* strain "Sure". Insertion of the oligonucleotide into the ClaI site will disrupt the ClaI recognition sites. The oligonucleotide contains a new ClaI site near one of its termini. In selected clones, the orientation and the integrity of the inserted oligonucleotide was verified by sequence analyses. A clone containing the oligonucleotide in the correct orientation (the ClaI site at the ITR side) was denoted pAd-CMV-hcTK. This plasmid was co-transfected with ClaI digested wild-type Adenovirus type 5 DNA into 911 cells. A recombinant adenovirus in which the CMV-hcTK expression cassette replaces the E1 sequences was isolated and propagated using standard procedures.

To study whether the hairpin can be used as a primer for reverse strand synthesis on the displaced strand after replication had started at the ITR, the plasmid pICLhac is introduced into 911 cells (human embryonic retinoblasts transformed with the adenovirus E1 region). The plasmid pICLhaw serves as a control, which contains the oligonucleotide pair HP/asp1 (SEQ ID NO:17) and HP/asp2 (SEQ ID NO:18) in the reverse orientation but is further completely identical to plasmid pICLhac. Also included in these studies are plasmids pICLI and pICL (SEQ ID NO:21). In the plasmid pICLI, the hairpin is replaced by an adenovirus ITR. Plasmid pICL (SEQ ID NO:21) contains neither a hairpin nor an ITR sequence. These plasmids serve as controls to determine the efficiency of replication by virtue of the terminal-hairpin structure. To provide the viral products other than the E1 proteins (these are produced by the 911 cells) required for DNA replication, the cultures are infected with the virus IG.Ad.MLPI.TK after transfection. Several parameters are being studied to demonstrate proper replication of the transfected DNA molecules. First, DNA extracted from the cell cultures transfected with aforementioned plasmids and infected with IG.Ad.MLPI.TK virus is being analyzed by Southern blotting for the presence of the expected replication intermediates, as well as for the presence of the duplicated genomes. Furthermore, virus is isolated from the transfected and IG.Ad.MLPI.TK infected cell populations that is capable of transferring and expressing a luciferase marker gene into luciferase negative cells.

Plasmid DNA of plasmids pICLhac, pICLhaw, pICLI, and pICL (SEQ ID NO:21) have been digested with restriction endonuclease SalI and treated with mungbean nuclease to remove the 4 nucleotide single-stranded extension of the resulting DNA fragment. In this manner, a natural adenovirus 5' ITR terminus on the DNA fragment is created. Subsequently, both the pICLhac and pICLhaw plasmids were digested with restriction endonuclease Asp718 to generate the terminus capable of forming a hairpin structure. The digested plasmids are introduced into 911 cells, using the standard calcium phosphate co-precipitation technique, four dishes for each plasmid. During the transfection, for each plasmid two of the cultures are infected with the IG.Ad.MLPI.TK virus using 5 infectious IG.Ad.MLPI.TK particles per cell. At twenty-hours post-transfection and forty hours post-transfection, one Ad.tk-virus-infected and one uninfected culture are used to isolate small molecular-weight DNA using the procedure devised by Hirt. Aliquots of isolated DNA are used for Southern analysis. After digestion of the samples with restriction endonuclease EcoRI using the luciferase gene as a probe, a hybridizing fragment of approximately 2.6 kb is detected only in the samples from the adenovirus infected cells transfected with plasmid pICLhac. The size of this fragment is consistent with the anticipated duplication of the luciferase marker gene. This supports the conclusion that the inserted hairpin is capable of serving as a primer for reverse strand synthesis. The hybridizing fragment is absent if the IG.Ad.MLPI.TK virus is omitted or if the hairpin oligonucleotide has been inserted in the reverse orientation.

The restriction endonuclease DpnI recognizes the tetranucleotide sequence 5'-GATC-3' but cleaves only methylated DNA (that is, only plasmid DNA propagated in and derived from *E. coli*, not DNA that has been replicated in mammalian cells). The restriction endonuclease MboI recognizes the same sequences, but cleaves only unmethylated DNA (viz. DNA propagated in mammalian cells). DNA samples isolated from the transfected cells are incubated with MboI and DpnI and analyzed with Southern blots. These results demonstrate that only in the cells transfected with the PICLhac and the pICLI plasmids are large DpnI-resistant fragments present that are absent in the MboI treated samples. These data demonstrate that only after transfection of plasmids pICLI and pICLhac does replication and duplication of the fragments occur.

These data demonstrate that in adenovirus-infected cells, linear DNA fragments that have on one terminus an adenovirus-derived ITR and at the other terminus a nucleotide sequence that can anneal to sequences on the same strand when present in single-stranded form, thereby generate a hairpin structure and will be converted to structures that have inverted terminal repeat sequences on both ends. The resulting DNA molecules will replicate by the same mechanism as the wild-type adenovirus genomes.

Experiment Series 2

The following demonstrates that the DNA molecules that contain a luciferase marker gene, a single copy of the ITR, the encapsidation signal, and a synthetic DNA sequence that is capable of forming a hairpin structure are sufficient to generate DNA molecules that can be encapsidated into virions.

To demonstrate that the above DNA molecules containing two copies of the CMV-luc marker gene can be encapsidated into virions, virus is harvested from the remaining two cultures via three cycles of freeze-thaw crushing and is used to infect murine fibroblasts. Forty-eight hours after infection, the infected cells are assayed for luciferase activity. To exclude the possibility that the luciferase activity has been induced by transfer of free DNA, rather than via virus particles, virus stocks are treated with DNaseI to remove DNA contaminants. Furthermore, as an additional control, aliquots of the virus stocks are incubated for 60 minutes at 56° C. The heat treatment will not affect the contaminating DNA but will inactivate the viruses. Significant luciferase activity is only found in the cells after infection with the virus stocks derived from IG.Ad.MLPI.TK-infected cells transfected with the pICLhc and pICLI plasmids. In neither the non-infected cells nor the infected cells transfected with the pICLhw and pICL (SEQ ID NO:21) can significant luciferase activity be demonstrated. Heat inactivation, but not DNaseI treatment, completely eliminates luciferase expression, demonstrating that adenovirus particles, and not free (contaminating) DNA fragments, are responsible for transfer of the luciferase reporter gene.

These results demonstrate that these small viral genomes can be encapsidated into adenovirus particles and suggest that the ITR and the encapsidation signal are sufficient for encapsidation of linear DNA fragments into adenovirus particles. These adenovirus particles can be used for efficient gene transfer. When introduced into cells that contain and express at least part of the adenovirus genes (viz. E1, E2, E4, and L, and VA), recombinant DNA molecules that consist of at least one ITR, at least part of the encapsidation signal, and a synthetic DNA sequence that is capable of forming a hairpin structure have the intrinsic capacity to autonomously generate recombinant genomes that can be encapsidated into virions. Such genomes and vector system can be used for gene transfer.

Experiment Series 3

The following demonstrates that DNA molecules that contain nucleotides 3510–35953 (viz. 9.7–100 map units) of the adenovirus type 5 genome (thus lacking the E1 protein-coding regions, the right-hand ITR, and the encapsidation sequences) and a terminal DNA sequence that is complementary to a portion of the same strand of the DNA molecule when present in single-stranded form other than the ITR, and as a result is capable of forming a hairpin structure, can replicate in 911 cells.

In order to develop a replicating DNA molecule that can provide the adenovirus products required to allow the above mentioned ICLhac vector genome and alike minimal adenovectors to be encapsidated into adenovirus particles by helper cells, the Ad-CMV-hcTK adenoviral vector has been developed. Between the CMV enhancer/promoter region and the thymidine kinase gene, the annealed oligonucleotide pair HP/cla1 (SEQ ID NO:19) and 2 (SEQ ID NO:20) is inserted. The vector Ad-CMV-hcTK can be propagated and produced in 911 cell using standard procedures. This vector is grown and propagated exclusively as a source of DNA used for transfection. DNA of the adenovirus Ad-CMV-hcTK is isolated from virus particles that had been purified using CsC1 density-gradient centrifugation by standard techniques. The virus DNA has been digested with restriction endonuclease ClaI. The digested DNA is size-fractionated on a 0.7% agarose gel, and the large fragment is isolated and used for further experiments. Cultures of 911 cells are transfected large ClaI-fragment of the Ad-CMV-hcTK DNA using the standard calcium phosphate co-precipitation technique. Much like in the previous experiments with plasmid pICLhac, the AD-CMV-hc will replicate starting at the right-hand ITR. Once the 1-strand is displaced, a hairpin can be formed at the left-hand terminus of the fragment. This facilitates the DNA polymerase to elongate the chain towards the right-hand-side. The process will proceed until the displaced strand is completely converted to its double-stranded form. Finally, the right-hand ITR will be recreated, and in this location the normal adenovirus replication-initiation and elongation will occur. Note that the polymerase will read through the hairpin, thereby duplicating the molecule. The input DNA molecule of 33250 bp, which had on one side an adenovirus ITR sequence and at the other side a DNA sequence that had the capacity to form a hairpin structure, has now been duplicated in a way that both ends contain an ITR sequence. The resulting DNA molecule will consist of a palindromic structure of approximately 66500 bp.

This structure can be detected in low-molecular weight DNA extracted from the transfected cells using Southern analysis. The palindromic nature of the DNA fragment can be demonstrated by digestion of the low-molecular weight DNA with suitable restriction endonucleases and Southern blotting with the HSV-TK gene as the probe. This molecule can replicate itself in the transfected cells by virtue of the adenovirus gene products that are present in the cells. In part, the adenovirus genes are expressed from templates that are integrated in the genome of the target cells (viz. the E1 gene products), the other genes reside in the replicating DNA fragment itself. Note however, that this linear DNA fragment cannot be encapsidated into virions. Not only does it lack all the DNA sequences required for encapsidation, but also is its size is also much too large to be encapsidated.

Experiment Series 4

The following demonstrates that DNA molecules that contain nucleotides 3503–35953 (viz. 9.7–100 map units) of the adenovirus type 5 genome (thus lacking the E1 protein-coding regions, the right-hand ITR, and the encapsidation sequences) and a terminal DNA sequence that is complementary to a portion the same strand of the DNA molecule other than the ITR, and as a result is capable of forming a hairpin structure, can replicate in 911 cells and can provide the helper functions required to encapsidate the pICLI and pICLhac derived DNA fragments.

The following series of experiments aims to demonstrate that the DNA molecule described in Experiment Series 3 could be used to encapsidate the minimal adenovectors described in Experiment Series 1 and 2.

In the experiments, the large fragment isolated after endonuclease ClaI-digestion of Ad-CMV-hcTK DNA is introduced into 911 cells (in conformity with the experiments described in part 1.3) together with endonuclease SalI, mungbean nuclease, endonuclease Asp718-treated plasmid pICLhac, or, as a control, similarly treated plasmid pICLhaw. After 48 hours, virus is isolated by freeze-thaw crushing of the transfected cell population. The virus-preparation is treated with DNaseI to remove contaminating free DNA. The virus is used subsequently to infect Rat2 fibroblasts. Forty-eight hours post infection, the cells are assayed for luciferase activity. Significant luciferase activity can be demonstrated only in the cells infected with virus isolated from the cells transfected with the pICLhac plasmid and not with the pICLhaw plasmid. Heat inactivation of the virus prior to infection completely abolishes the luciferase activity, indicating that the luciferase gene is transferred by a viral particle. Infection of 911 cell with the virus stock did not result in any cytopathological effects, demonstrating that the pICLhac is produced without any infectious helper virus that can be propagated on 911 cells. These results demonstrate that the proposed method can be used to produce stocks of minimal adenoviral vectors that are completely devoid of infectious helper viruses and are able to replicate autonomously on adenovirus-transformed human cells or on non-adenovirus transformed human cells.

Besides the system described in this application, another approach for the generation of minimal adenovirus vectors has been disclosed in International Patent Publication WO 94/12649. The method described in WO 94/12649 exploits the function of the protein IX for the packaging of minimal adenovirus vectors (Pseudo Adenoviral Vectors ("PAV") in the terminology of WO 94/12649). PAVs are produced by cloning an expression plasmid with the gene of interest between the left-hand (including the sequences required for encapsidation) and the right-hand adenoviral ITRs. The PAV is propagated in the presence of a helper virus. Encapsidation of the PAV is preferred compared with the helper virus because the helper virus is partially defective for packaging (either by virtue of mutations in the packaging signal or by virtue of its size, virus genomes greater than 37.5 kb package inefficiently). In addition, the authors propose that in the absence of the protein IX gene, the PAV will be preferentially packaged. However, neither of these mechanisms appear to be sufficiently restrictive to allow packaging of only PAVs/minimal vectors. The mutations proposed in the packaging signal diminish packaging but do not provide an absolute block, as the same packaging-activity is required to propagate the helper virus. Also, neither an increase in the size of the helper virus nor the mutation of the protein IX gene will ensure that PAV is packaged exclusively. Thus, the method described in WO 94/12649 is unlikely to be useful for the production of helper-free stocks of minimal adenovirus vectors/PAVs.

Although the application has been described with reference to certain preferred embodiments and illustrative examples, the scope of the invention is to be determined by reference to the appended claims.

REFERENCES

Berk, A. J. (1986): *Ann. Rev. Genet.* 20, 45–79.

Bernards, R., Schrier, P. I., Bos, J. L., and Eb, A. J. v. d. (1983): Role of adenovirus types 5 and 12 early region 1b tumor antigens in oncogenic transformation. *Virology* 127, 45–53.

Bett, A. J , Prevec, L., and Graham, F. L. (1993): Packaging Capacity and Stability of Human Adenovirus Type-5 Vectors. *J. Virol.* 67, 5911–5921.

Blaese, M., Blankenstein, T., Brenner, M., Cohen-Hageenauer, O., Gansbacher, B., Russell, S., Sorrentino, B., and Velu, T. (1995). Vectors in cancer therapy: how will they deliver? *Cancer Gene Ther.* 2, 291–297.

Boshart, M., Weber, F., Jahn, G., Dorsch-Häler, K., Fleckenstein, B., and Scaffner, W. (1985): A very strong enhancer is located upstream of an immediate early gene of human Cytomegalovirus. *Cell* 41, 521–530.

Bout, A., Imler, J. L., Schulz, H., Perricaudet, M., Zurcher, C., Herbrink, P., Valerio, D., and Pavirani, A. (1994a): In vivo adenovirus-mediated transfer of human CFTR cDNA to Rhesus monkey airway epithelium: efficacy, toxicity and safety. *Gene Therapy* 1, 385–394.

Bout, A., Perricaudet, M., Baskin, G., Imler, J. L., Scholte. B. J., Pavirani, A., and Valerio, D. (1994b): Lung gene therapy: in vivo adenovirus mediated gene transfer to rhesus monkey airway epithelium. *Human Gene Therapy* 5, 3–10.

Brody, S. L., and Crystal, R. G. (1994): Adenovirus-mediated in vivo gene transfer. *Ann. N.Y Acad. Sci.* 716, 90–101.

Brough, D. E., Cleghon, V., and Klessig, D. F. (1992). Construction, characterization, and utilization of cell lines which inducibly express the adenovirus DNA-binding protein. *Virology* 190(2), 624–34.

Brough, D. E., Rice, S. A., Sell, S., and Klessig, D. F. (1985): Restricted changes in the adenovirus DNA-binding protein that lead to extended host range or temperature-sensitive phenotypes. *J. Virol.* 55, 206–212.

Daniell, E. (1976): Genome structure of incomplete particles of adenovirus. *J. Virol.* 19, 685–708.

El sen, P. J. V. d., Houweling, A., and Eb, A. J. V. d. (1983). Expression of region E1B of human adenoviruses in the absence of region E1A is not sufficient for complete transformation. *Virology* 128, 377–390.

Engelhardt, J. F., Litzky, L., and Wilson. J. M. (1994a): Prolonged transgene expression in cotton rat lung with recombinant adenoviruses defective in E2A. *Human Gene Therapy* 5. 1217–1229.

Engelhardt, J. F., Simon, R. H., Yang, Y., Zepeda, M., Weber-Pendleton, S., Doranz, B., Grossman, M., and Wilson, J. M. (1993): Adenovirus-mediated transfer of the CFTR gene to lung or nonhuman primates: biological efficacy study. *Human Gene Therapy* 4, 759–769.

Engelhardt, J. F., Ye, X., Doranz, B., and Wilson, J. M. (1994b): Ablation of E2A in recombinant adenoviruses improves transgene persistence and decreases inflammatory response in mouse liver. *Proc. Nat'l Acad. Sci. USA* 91, 6196–200.

Fang, B., Wang, H., Gordon, G., Bellinger, D. A., Read, M. S., Brinkhous, K. M., Woo, S. L. C., and Eisensmith, R. C. (1996). Lack of persistence of E1-recombinant adenoviral vectors containing a temperature sensitive E2A mutation in immunocompetent mice and hemophilia dogs. *Gene Therapy* 3, 217–222.

Fallaux, F. J., Kranenburg, O., Cramer. S. J., Houweling, A., Ormondt, H. v., Hoeben. R. C., and Eb, A. J. v.d. (1996). Characterization of 911: a new helper cell line for the titration and propagation of early-region 1-deleted adenoviral vectors. *Human Gene Therapy* 7, 215–222.

Gooding, L. R., Aquino, L., Duerksen-Hughes, P. J., Day, D., Horton, T. M., Yei, S., and Wold, W. S. M. (1991): The E1B 19,000-molecular-weight protein of group C adenoviruses prevents tumor necrosis factor cytolysis of human cells but not of mouse cells. *J. Virol.* 65, 3083–3094.

Gräble, M., and Hearing, P. (1990): Adenovirus type 5 packaging domain is composed of a repeated element that is functionally redundant. *J. Virol.* 64, 2047–2056.

Gräble, M., and Hearing, P. (1992): cis and trans Requirements for the Selective Packaging of Adenovirus Type-5 DNA. *J. Virol.* 66, 723–731.

Graham, F. L., and van der Eb, A. J. (1973). A new technique for the assay of infectivity of human adenovirus 5 DNA. *Virology* 52, 456–467.

Graham, F. L., Smiley, J., Russell, W. C., and Naira, R. (1977): Characteristics of a human cell line transformed by DNA from adenovirus type 5. *J. Gen. Virol.* 36, 59–72.

Haddada, H., Ragot, T., Cordier, L., Duffour, M. T., and Perricaudet, M. (1993): Adenoviral interleukin-2 gene transfer into P815 tumor cells abrogates tumorigenicity and induces antitumoral immunity in mice. *Human Gene Therapy* 4, 703–11.

Hay, R. T., Stow, N. D., and McDougall, I. M. (1984): Replication of adenovirus minichromosomes. *J. Mol. Biol.* 174, 493–510.

Hearing, P., Samulski, R. J., Wishart, W. L., and Shenk, T. (1987): Identification of a repeated sequence element required for efficient encapsidation of the adenovirus type 5 chromosome. *J. Virol.* 61, 2555–2558.

Horwitz, M. S. (1990): Adenoviridae and their replication, pp. 1679–1740. In B. N. Fields, and D. M. Knipe (Eds): *Virology*, Raven Press, Ltd, New York.

Hu, C. H., Xu, F. Y., Wang, K.; Pearson, A. N., and Pearson, G. D. (1992): Symmetrical Adenovirus Minichromosomes Have Hairpin Replication Intermediates. *Gene* 110, 145–150.

Imler, J. L., Chartier, C., Dreyer, D., Dieterle, A., Sainte-Marie, M., Faure, T., Pavirani, A., and Mehtali, M. (1996). Novel complementation cell lines derived from human lung tarcinoma A549 cells support the growth of E1-deleted adenovirus vectors. *Gene Ther.* 3, 75–84.

Jochemsen. A. G., Peltenburg, L. T. C., Pas, M. F. W. T., Wit, C. M. d., Bos, J. L., and Eb. A. J. v. d. (1987): *EMBO J.* 6, 3399–3405.

Klessig, D. F., and Grodzicker, T. (1979): Mutations that allow human Ad2 and Ad5 to express late genes in monkey cells maps in the viral gene encoding the 72K DNA-binding protein. *Cell* 17, 957–566.

Klessig, D. F. Grodzicker, T., and Cleghon, V. (1984): Construction of human cell lines which contain and express the adenovirus DNA binding protein gene by cotransformation with the HSV-1 tk gene. *Virus Res.* 1, 169–188.

Kruijer, W., Nicolas, J. C., Schaik. F. M. v., and Sussenbach, J. S. (1983): Structure and function of DNA binding proteins from revertants of adenovirus type 5 mutants with a temperature-sensitive DNA replication. *Virology* 124, 425–433.

Lechner, R. L., and Kelly Jr., T. J. (1977): The structure of replicating adenovirus 2 DNA molecules. *J. Mol. Biol.* 174, 493–510.

Leij, L. de, Postmus, P. E., Buys, C. H. C. M., Elema, J. D., Ramaekers, F., Poppema, S., Brouwer, M., Veen, A. Y. v.d., Mesander, G., and The, T. H. (1985): Characterization of three new variant type cell lines derived from small cell carcinoma of the lung. *Cancer Res.* 45, 6024–6033.

Levrero, M., Barban, V., Manteca, S., Ballay, A., Balsamo, C., Avantaggiati, M. L., Natoli, G., Skellekens, H., Tiollais, P., and Perricaudet, M. (1991): Defective and non-defective adenovirus vectors for expressing foreign genes in vitro and in vivo. *Gene* 101, 195–202.

Lochmüller, H., Jani, A., Huard, J., Prescott, S., Simoneau, M., Massie, B., Karpati, G., and Acasdi, G. (1994): Emergence of early region 1-containing replication-competent adenovirus in stocks of replication-defective adenovirus recombinants (ΔE1–ΔE3) during multiple passages in 293 cells. *Hum. Gene Ther.* 5, 1485–1492.

Matsui, T., Murayama, M., and Mita, T. (1986): Adenovirus 2 peptide IX is expressed only on replicated DNA molecules. *Mol. Cell Biol.* 6, 4149–4154.

Michelson, A. M., Markham, A. F., and Orkin, S. H. (1983): Isolation and DNA sequence of a full-length cDNA clone for human X-chromosome encoded phosphoglycerate kinase. *Proc. Nat'l Acad. Sci. USA* 80, 472–476.

Morin, J. E., Lubeck, M. D., Barton. J. E., Conley, A. J., Davis, A. R., and Hung, P. P. (1987): Recombinant adenovirus induces antibody response to hepatitis B virus surface antigens. *Proc. Nat'l Acad. Sci. USA*, 84, 4626–4630.

Nicolas, J. C., Suarez, F., Levine, A. J., and Girard, M. (1981): Temperature-independent revertants of adenovirus H5ts125 and H5ts107 mutants in the DNA binding protein: isolation of a new class of host range temperature conditional revertants. *Virology* 108, 521–524.

Ostrove, J. M. (1994): Safety testing programs for gene therapy viral vectors. *Cancer Gene Therapy* 1, 125–131.

Pacini, D. L., Dubovi, E. J., and Clyde, W. A. (1984): *J. Infect. Dis.* 150, 92–97.

Postmus, P. E., Ley, L. d., Veen, A. Y. v. d., Mesander, G., Buys, C. H. C. M., and Elema, J. D. (1988): Two small cell lung cancer cell lines established from rigid bronchoscope biopsies. *Eur. J. Clin. Oncol.* 24, 753–763.

Rice, S. A., and Klessig, D. F. (1985): Isolation and analysis of adenovirus type 5 mutants containing deletions in the gene encoding the DNA-binding protein. *J. Virol.* 56, 767–778.

Roberts, B. E., Miller, J. S., Kimelman, D., Cepko, C. L., Lemischka, I. R., and Mulligan, R. C. (1985): *J. Virol.* 56, 404–413.

Shapiro, D. L., Nardone, L. L., Rooney, S. A., Motoyama, E. K., and Munoz, J. L. (1978). Phospholipid biosynthesis and secretion by a cell line (A549) which resembles type II alveolar epithelial cells. *Biochim. Biophys. Acta* 530, 197–207.

Simon, R. H., Engelhardt, J. F., Yang, Y., Zepeda., M., Weber-Pendleton, S., Grossman, M., and Wilson, J. M. (1993): Adenovirus-mediated transfer of the CFTR gene to lung of nonhuman primates: toxicity study. *Human Gene Therapy* 4, 771–780.

Singer-Sam, J., Keith, D. H., Tani, K., Simmer, R. L., Shively, L., Lindsay, S., Yoshida, A., and Riggs, A. D. (1984): Sequence of the promoter region of the gene for X-linked 3-phosphoglycerate kinase. *Gene* 32, 409–417.

Stein, R. W., and Whelan, J. (1989): Insulin gene enhancer activity is inhibited by adenovirus 5 E1A gene products. *Mol Cell Biol* 9,4531–4.

Stratford-Perricaudet, L. D., and Perricaudet, M. (1991): Gene transfer into animals: the promise of adenovirus, pp. 51–61. In O. Cohen-Adenauer, and M. Boiron (Eds): *Human Gene Transfer*, John Libbey Eurotext.

Telling, G. C., Perera, S., Szatkowski, O. M., and Williams, J. (1994): Absence of an essential regulatory influence of the adenovirus E1B 19-kilodalton protein on viral growth and early gene expression in human diploid WI38, HeLa, and A549 cells. *J. Virol* 68,541–7.

Tooze, J. (1981): *DNA Tumor Viruses* (revised). Cold Spring Harbor Laboratory. Cold Spring Harbor, N.Y.

Vieira, J., and Messing, J. (1987): Production of single stranded plasmid DNA, pp. 3–11: *Methods in Enzymology*, Acad. Press Inc.

Vincent, A. J. P. E., Esandi, M. d. C., Someren, G. D. v., Noteboom, J. L., C. J. J, A., Vecht, C., Smitt, P. A. E. S., Bekkum, D. W. v., Valerio, D., Hoogerbrugge, P. M., and Bout, A. (1996a). Treatment of Lepto-meningeal metastasis in a rat model using a recombinant adenovirus containing the HSV-tk gene. *J. Neurosurg.* in press.

Vincent, A. J. P. E., Vogels, R., Someren, G. v, Esandi, M. d. C., Noteboom, J. L., Avezaat, C. J. J., Vecht, C., Bekkum, D. W. v., Valerio, D., Bout, A., and Hoogerbrugge, P. M. (1996b). Herpes Simplex Virus Thymidine Kinase gene therapy for rat malignant brain tumors. *Hum. Gene Ther.* 7, 197–205.

Wang, K., and Pearson, G. D. (1985): Adenovirus sequences required for replication in vivo. *Nucl. Acids Res.* 13, 5173–5187.

White, E., Denton, A., and Stillman, B. (1988): *J. Virol.* 62, 3445–3454.

Yang, Y., Li, Q., Ertl, H. C. J., and Wilson, J. M. (1995): Cellular and humoral immune responses viral antigens create barriers to lung-directed gene therapy with recombinant adenoviruses. *J. Virol.* 69, 2004–2015.

Yang, Y., Nunes, F. A., Berencsi, K., Furth, E. E., Gonczol, E., and Wilson, J. M. (1994a): Cellular immunity to viral antigens limits E1-deleted adenoviruses for gene therapy. *Proc Nat'l Acad. Sci. USA* 91, 4407–11.

Yang, Y., Nunes, F. A., Berencsi, K., Gonczol, E., Engelhardt, J. F., and Wilson, J. M. (1994b): Inactivation of E2A in recombinant adenoviruses improves the prospect for gene therapy in cystic fibrosis. *Nature Genetics* 7, 362–9.

Zantema, A., Fransen, J. A. M., Davis-Olivier, A., Ramaekers, F. C. S., Vooijs, G. P., Deleys, B., and Eb, A. J. v.d. (1985). Localization of the E1B proteins of adenovirus 5 in transformed cells, as revealed by interaction with monoclonal antibodies. *Virology* 142, 44–58.

What is claimed is:

1. A nucleic acid molecule consisting of the sequences present in pIG.E1A.E1B.

2. An isolated first nucleic acid molecule comprising genetic information encoding functional adenovirus E1A and E1B 55 kDa gene products, wherein said first nucleic acid molecule lacks an adenovirus pIX gene, and further wherein said first nucleic acid molecule lacks genetic information encoding a functional adenovirus E1B 21 kDa protein.

3. An isolated adenovirus packaging cell comprising a first nucleic acid molecule comprising genetic information encoding functional adenovirus E1A, E1B 21kDa and E1B 55 kDa gene products,
  wherein said first nucleic acid molecule lacks genetic information from an adenovirus pIX gene that can mediate homologous recombination with a second nucleic acid molecule having genetic information encoding a functional or active adenovirus pIX gene product, and
  wherein said first nucleic acid molecule lacks genetic information encoding adenovirus proteins other than proteins encoded by adenovirus early region 1, and
  wherein the isolated adenovirus packaging cell is derived from an A549 cell.

* * * * *

UNITED STATES PATENT AND TRADEMARK OFFICE
CERTIFICATE OF CORRECTION

PATENT NO. : 7,105,346 B2  Page 1 of 5
APPLICATION NO. : 10/125751
DATED : September 12, 2006
INVENTOR(S) : Frits J. Fallaux et al.

It is certified that error appears in the above-identified patent and that said Letters Patent is hereby corrected as shown below:

On the title page:
In ITEM (60) "Related U.S.
  Application Data,"  5th line,  after "08/793,170," insert --now Pat. No. 5,994,128,--
                          6th-7th lines,  change "1996, now Pat. No. 5,994,128." to --1996.--

In ITEM (56) "References Cited, OTHER PUBLICATIONS,"
Page 3,  1st column,  27th line,  change "#Broough" to --#Brough--
Page 3,  2nd column,  5th line,   change "drived" to --derived--
Page 3,  2nd column,  21st line,  change "Stock" to --Stocks--
Page 3,  2nd column,  55th line,  change "#Vamjaesebrpecl. Bart. et el.," to --#Vanhaesebroeck, Bart, et al.,--
Page 3,  2nd column,  59th line,  change "#Vox et al.," to --#Vos et al.,--
Page 3,  2nd column,  69th line,  change "adenovirus" to --adenoviruses--
Page 4,  1st column,  2nd line,   change "293-Dervied" to --293-Derived--
Page 4,  1st column,  25th line,  change "pess," to --Press,--
Page 4,  1st column,  28th line,  change "portein" to --protein--
Page 4,  1st column,  35th line,  change "type 5)." to --type 5), Jan. 26, 2005.--
Page 4,  1st column,  48th line,  change "at 9 A" to --at 2-9 Å--
Page 4,  1st column,  51st line,  change "PentonBase" to --Penton Base--
Page 4,  1st column,  57th line,  change "Firbotropism" to --Fibrotropism--
Page 4,  1st column,  58th line,  change "Subitutions" to --Substitutions--
Page 4,  2nd column,  2nd line,   change "pp. 90-101." to --pp. 90-100.--
Page 4,  2nd column,  4th line,   change "Serotype2 Fibre,"" to --Serotype 2 Fibre,"--
Page 4,  2nd column,  12th line,  change "antibodyenvelope" to --antibody-envelope-- and change "1, 292-299" to --1, (5):292-299--
Page 4,  2nd column,  23rd line,  change "location" to --Location--
Page 4,  2nd column,  24th line,  change "SerotypeSpecific" to --Serotype-Specific--
Page 4,  2nd column,  26th line,  change "Cromptoon" to --Crompton--
Page 4,  2nd column,  31st line,  change "DNAPolylysine" to --DNA Polylysine--
Page 4,  2nd column,  32nd line,  change "3, 147-154" to --3, (2):147-154--
Page 4,  2nd column,  33rd line,  change "oftransferring-polylysine-" to --of transferring polylysine- --
Page 4,  2nd column,  40th line,  change "Virusinfected" to --Virus-infected--
Page 4,  2nd column,  41st line,  change "Candiate" to --Candidate--
Page 4,  2nd column,  52nd line,  change "et al.:" to --et al.,--

UNITED STATES PATENT AND TRADEMARK OFFICE
CERTIFICATE OF CORRECTION

PATENT NO. : 7,105,346 B2
APPLICATION NO. : 10/125751
DATED : September 12, 2006
INVENTOR(S) : Frits J. Fallaux et al.

It is certified that error appears in the above-identified patent and that said Letters Patent is hereby corrected as shown below:

On the title page:
In ITEM (56) "References Cited, OTHER PUBLICATIONS," continued

| | | | |
|---|---|---|---|
| Page 4, | 2nd column, | 53rd line, | change "tropismmodified" to --tropism-modified-- |
| Page 4, | 2nd column, | 56th line, | change "" Regenerating" to --"Regenerating-- |
| Page 4, | 2nd column, | 64th line, | change "on th" to --on the-- |
| Page 4, | 2nd column, | 65th line, | change "cellvirus" to --cell virus-- |
| Page 4, | 2nd column, | 67th line, | change "Mde by" to --Made by-- |
| Page 4, | 2nd column, | 68th line, | change "Journal 6 Virology," to --Journal of Virology,-- |
| Page 4, | 2nd column, | 70th line, | change "Flomenbert" to --Flomenberg-- |
| Page 5, | 1st column, | 18th line, | change "cross: sheet" to --cross-β sheet-- |
| Page 5, | 1st column, | 30th line, | change "adenovirus,"" to --adenoviruses,-- |
| Page 5, | 1st column, | 49th line, | change "y3 and y5" to --αvβ3 and αvβ5-- |
| Page 5, | 1st column, | 50th line, | change "TLymphocytes" to --T Lymphocytes-- and change "Adenovirus Mediated" to --Adenovirus-Mediated-- |
| Page 5, | 1st column, | 52nd line, | change "viral" to --Viral-- |
| Page 5, | 1st column, | 54th line, | change "Dna" to --DNA-- |
| Page 5, | 1st column, | 63rd-64th lines, | change "adenovirusmediated" to --adenovirus-mediated-- and change "myocytes*in vitro*" to --myocytes *in vitro*-- |
| Page 5, | 1st column, | 69th line, | change 'Typespecific" to --Type-specific-- |
| Page 5, | 1st column, | 73rd line, | change "LeucineAspartic" to --Leucine-Aspartic-- |
| Page 5, | 2nd column, | 6th line, | change "Vectormediated" to --Vector-mediated-- |
| Page 5, | 2nd column, | 9th line, | change "E1, E3" to --E1⁻, E3⁻-- |
| Page 5, | 2nd column, | 13th line, | change "gnes in vitro and invivo,"" to --genes in vitro and in vivo,"-- |
| Page 5, | 2nd column, | 19th line, | change "(2003 10, 93540." to --(2003) 10, 935-940.-- |
| Page 5, | 2nd column, | 20th line, | change "Immunotherapy B An" to --Immunotherapy: An-- |

UNITED STATES PATENT AND TRADEMARK OFFICE
CERTIFICATE OF CORRECTION

PATENT NO. : 7,105,346 B2
APPLICATION NO. : 10/125751
DATED : September 12, 2006
INVENTOR(S) : Frits J. Fallaux et al.

It is certified that error appears in the above-identified patent and that said Letters Patent is hereby corrected as shown below:

On the title page:
In ITEM (56) "References Cited,
OTHER PUBLICATIONS," continued

| | | | |
|---|---|---|---|
| Page 5, | 2nd column, | 26th line, | change "Chaning" to --Changing-- |
| Page 5, | 2nd column, | 28th line, | change "Use v Integrins" to --Use αv Integrins-- |
| Page 5, | 2nd column, | 31st line, | change "Recominants,"" to --Recombinants."-- |
| Page 5, | 2nd column, | 40th line, | change "(1995)/" to --(1995).-- |
| Page 5, | 2nd column, | 42nd line, | change "Conjugatemediated" to --Conjugate-mediated-- |
| Page 5, | 2nd column, | 52nd line, | change "forα" to --for $α_v$-- |
| Page 5, | 2nd column, | 55th line, | change "inBaculovirus-Expressed" to --in Baculovirus-Expressed-- |
| Page 5, | 2nd column, | 58th line, | change "TripleStranded-Helical Coiled-Coil,"" to --Triple-Stranded Alpha-Helical Coiled-Coil,"-- |
| Page 5, | 2nd column, | 65th line, | change ""Effecient" to --"Efficient-- |
| Page 5, | 2nd column, | 69th line, | change "monocyto-" to --monocyte- -- |
| Page 5, | 2nd column, | 70th line, | change "fibermodified" to --fiber-modified-- |
| Page 5, | 2nd column, | 71st line, | change "transgeno-encoded" to --transgene-encoded-- |
| Page 6, | 1st column, | 4th line, | change "114851" to --1148-51-- |
| Page 6, | 1st column, | 6th line, | change "Proteinfor" to --Protein for-- |
| Page 6, | 1st column, | 15th line, | change "pp. 1165." to --pp. 1165-1171, 1194.-- |
| Page 6, | 1st column, | 20th-21st lines, | change "Adenovirusmediated" to --Adenovirus-mediated-- |
| Page 6, | 1st column, | 22nd line, | change "209219." to --201-219.-- |
| Page 6, | 1st column, | 24th line, | change "hematopietic" to --hematopoietic-- |
| Page 6, | 1st column, | 31st line, | change "Signàas" to --Signäs-- |
| Page 6, | 2nd column, | 4th line, | change "(199208)," to --(199-208),-- |
| Page 6, | 2nd column, | 14th line, | change "Immunoogy," to --Immunology,-- |
| Page 6, | 2nd column, | 15th line, | change "transferring-polylysine/" to --transferrin-polylysine-- |
| Page 6, | 2nd column, | 21st line, | change "$_{y3}$ and $_{y5}$" to --$αν β3$ and $αν β5$-- |
| Page 6, | 2nd column, | 22nd line, | change "309319" to --309-319-- |
| Page 6, | 2nd column, | 23rd line, | change "$_{y5}$" to --$αν β5$-- |
| Page 6, | 2nd column, | 32nd line, | change "964972," to --964-972,-- |

UNITED STATES PATENT AND TRADEMARK OFFICE
CERTIFICATE OF CORRECTION

PATENT NO.      : 7,105,346 B2
APPLICATION NO. : 10/125751
DATED           : September 12, 2006
INVENTOR(S)     : Frits J. Fallaux et al.

It is certified that error appears in the above-identified patent and that said Letters Patent is hereby corrected as shown below:

Title page Item [56]
Insert the following "OTHER PUBLICATIONS":
--Peshwa et al., "Cultivation of Mammalian Cells as Aggregates in Bioreactors: Effect of Calcium Concentration on Spatial Distribution of Viability," Biotech. Bioeng., 1993, pp. 179-87, Vol. 41.
Prelich et al., "Functional Characterization of Thermolabile DNA-Binding Proteins That Affect Adenovirus DNA Replication," Journal of Virology, Mar. 1986, pp. 883-92, Vol. 57, No. 3.
Rao et al., "The adenovirus E1A proteins induce apoptosis, which is inhibited by the E1B 19-kDa and Bcl-2 proteins," Proc. Natl. Acad. Sci., August 1992, pp. 7742-46, Vol. 89.
Rhim, Johng S., "Development of Human Cell Lines from Multiple Organs," 2000, Annals New York Academy of Sciences, pp. 16-25.
Rowe et al., "Establishment and Characterization of Hamster Cell Lines Transformed by Restriction Endonuclease Fragments of Adenovirus 5," Journal of Virology, Jan. 1984, pp. 162-70, Vol. 49, No. 1.
Ruley, H. Earl, "Adenovirus early region 1A enables viral and cellular transforming genes to transform primary cells in culture," Nature, August 1983, pp. 602-06, Vol. 304.
Sambrook et al., "Molecular Cloning: A Laboratory Manual," $3^{rd}$ edition, 2001, Cold Spring Harbor Laboratory Press, Cold Spring Harbor, New York, pp. 16.1-16.6.
White et al., "Adenovirus E1B 19-Kilodalton Protein Overcomes the Cytotoxicity of E1A Proteins," Journal of Virology, June 1991, pp. 2968-78, Vol. 65 No. 6.
White et al., "Role of Adenovirus E1B Proteins in Transformation: Altered Organization of Intermediate Filaments in Transformed Cells That Express the 19-Kilodalton Protein," Molecular and Cellular Biology, Jan. 1990, pp. 120-30, Vol. 10, No. 1.
White et al., "Specific disruption of intermediate filaments and the nuclear lamina by the 19-kDa product of the adenovirus E1B oncogene," Proc. Natl. Acad. Sci., December 1989, pp. 9886-90, Vol. 86.
White et al., "The 19-Kilodalton Adenovirus E1B Transforming Protein Inhibits Programmed Cell Death and Prevents Cytolysis by Tumor Necrosis Factor alpha," Molecular and Cellular Biology, June 1992, pp. 2570-80, Vol. 12, No. 6.
Woodworth et al., "Transformation of Differentiated Rat Hepatocytes with Adenovirus and Adenovirus DNA," Journal of Virology, Nov. 1987, pp. 3570-79, Vol. 61, No. 11.--

UNITED STATES PATENT AND TRADEMARK OFFICE
CERTIFICATE OF CORRECTION

PATENT NO.         : 7,105,346 B2
APPLICATION NO. : 10/125751
DATED              : September 12, 2006
INVENTOR(S)        : Frits J. Fallaux et al.

It is certified that error appears in the above-identified patent and that said Letters Patent is hereby corrected as shown below:

In the specification:

| | | |
|---|---|---|
| COLUMN 2, | LINES 48-49, | change "ransformation." to --transformation.-- |
| COLUMN 6, | LINE 34, | change "PER.C 1," to --PER.C1,-- |
| COLUMN 22, | LINE 52, | change "plCLhac" to --pICLhac-- |
| COLUMN 22, | LINE 61, | change "mungbean" to --mung bean-- |
| COLUMN 24, | LINE 43, | change "PICLhac" to --pICLhac-- |
| COLUMN 25, | LINE 53, | change "HP/cla1" to --HP/c1aI-- |

Signed and Sealed this

Twenty-fourth Day of March, 2009

JOHN DOLL
*Acting Director of the United States Patent and Trademark Office*

```
                          SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Ea-1

<400> SEQUENCE: 1
cgtgtagtgt atttataccc g                                          21

<210> SEQ ID NO 2
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: Description of Artifical Sequence: Primer Ea-2

<400> SEQUENCE: 2
tcgtcactgg gtggaaagcc a                                          21

<210> SEQ ID NO 3
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Ea-3

<400> SEQUENCE: 3
tacccgccgt cctaaaatgg c                                          21

<210> SEQ ID NO 4
<211> LENGTH: 20
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  Primer Ea-
      5

<400> SEQUENCE: 4
tggacttgag ctgtaaacgc                                            20

<210> SEQ ID NO 5
<211> LENGTH: 21
<212> TYPE: DNA
```

```
<213> ORGANISM: Artificial Sequence
<220> FEATURE:
<221> NAME/KEY:
<222> LOCATION:
<223> OTHER INFORMATION: Description of Artificial Sequence: Primer Ep-2

<400> SEQUENCE: 5
gcctccatgg aggtcagatg t                                         21

<210> SEQ ID NO 6
<211> LENGTH: 20
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Eb-1

<400> SEQUENCE: 6
gcttgagccc gagacatgtc                                           20

<210> SEQ ID NO 7
<211> LENGTH: 24
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer Eb-2

<400> SEQUENCE: 7
cccctcgagc tcaatctgta tctt                                      24

<210> SEQ ID NO 8
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  Primer
      SV40-1

<400> SEQUENCE: 8
gggggatccg aacttgttta ttgcagc                                   27

<210> SEQ ID NO 9
<211> LENGTH: 25
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer
      SV40-2

<400> SEQUENCE: 9
gggagatcta gacatgataa gatac                                     25

<210> SEQ ID NO 10
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer
      Ad5-1
```

```
<400> SEQUENCE: 10
gggagatctg tactgaaatg tgtgggc                                          27

<210> SEQ ID NO 11
<211> LENGTH: 24
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer
      Ad5-2

<400> SEQUENCE: 11
ggaggctgca gtctccaacg gcgt                                             24

<210> SEQ ID NO 12
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer ITR1

<400> SEQUENCE: 12
gggggatcct caaatcgtca cttccgt                                          27

<210> SEQ ID NO 13
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: Primer ITR2

<400> SEQUENCE: 13
ggggtctaga catcatcaat aatatac                                          27

<210> SEQ ID NO 14
<211> LENGTH: 32
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCR primer
      PCR/MLP1

<400> SEQUENCE: 14
ggcgaattcg tcgacatcat caataatata cc                                    32

<210> SEQ ID NO 15
<211> LENGTH: 32
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  PCT primer
      PCR/MLP2

<400> SEQUENCE: 15
ggcgaattcg gtaccatcat caataatata cc                                    32

<210> SEQ ID NO 16
```

```
<211> LENGTH: 17
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCT primer
      PCR/MLP3

<400> SEQUENCE: 16
ctgtgtacac cggcgca                                                    17

<210> SEQ ID NO 17
<211> LENGTH: 50
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCT primer
      HP/asp1

<400> SEQUENCE: 17
gtacactgac ctagtgccgc ccgggcaaag cccgggcggc actaggtcag                50

<210> SEQ ID NO 18
<211> LENGTH: 50
<212> TYPE: DNA
<213> ORGANISM: Artificial Sequence
<220> FEATURE:
<221> NAME/KEY:
<222> LOCATION:
<223> OTHER INFORMATION: Description of Artificial Sequence:  PCT primer
      HP/asp2

<400> SEQUENCE: 18
gtacctgacc tagtgccgcc cgggctttgc ccgggcggca ctaggtcagt                50

<210> SEQ ID NO 19
<211> LENGTH: 55
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: PCT primer
      HP/cla1

<400> SEQUENCE: 19
gtacattgac ctagtgccgc ccgggcaaag cccgggcggc actaggtcaa tcgat          55

<210> SEQ ID NO 20
<211> LENGTH: 55
<212> TYPE: DNA
<213> ORGANISM: Artificial Sequence
<220> FEATURE:
<221> NAME/KEY:
<222> LOCATION:
<223> OTHER INFORMATION: Description of Artificial Sequence: primer
      HP/cla2

<400> SEQUENCE: 20
gtacatcgat tgacctagtg ccgcccgggc tttgcccggg cggcactagg tcaat          55

<210> SEQ ID NO 21
<211> LENGTH: 5620
<212> TYPE: DNA
<213> ORGANISM: Artificial Sequence
<220> FEATURE:
```

-continued

```
<221> NAME/KEY: Ad5 left terminus
<222> LOCATION: 1..457
<220> FEATURE:
<221> NAME/KEY: enhancer
<222> LOCATION: 458..969
<220> FEATURE:
<221> NAME/KEY: exon
<222> LOCATION: 970..1204
<220> FEATURE:
<221> NAME/KEY: gene
<222> LOCATION: 1218..2987
<220> FEATURE:
<221> NAME/KEY: polyA_signal
<222> LOCATION: 3018..3131
<220> FEATURE:
<221> NAME/KEY: pUC12 backbone
<222> LOCATION: 3132..5620
<220> FEATURE:
<221> NAME/KEY: gene
<222> LOCATION: 4337..5191
<223> OTHER INFORMATION: Description of Artificial Sequence: Plasmid
      pICL

<400> SEQUENCE: 21
catcatcaat aatataccttt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgttttg    180 gtgtgcgccg gtgtacacag gaagtgacaa ttttcgcgcg gttttaggcg gatgttgtag   240
taaatttggg cgtaaccgag taagatttgg ccatttttcgc gggaaaactg aataagagga   300
agtgaaatct gaataatttt gtgttactca tagcgcgtaa tatttgtcta gggccgcggg   360
gactttgacc gtttacgtgg agactcgccc aggtgttttt ctcaggtgtt ttccgcgttc   420
cgggtcaaag ttggcgtttt attattatag tcaggggctg caggtcgtta cataacttac   480
ggtaaatggc ccgcctggct gaccgcccaa cgaccccgc ccattgacgt caataatgac    540
gtatgttccc atagtaacgc caatagggac tttccattga cgtcaatggg tggagtattt   600
acggtaaact gcccacttgg cagtacatca agtgtatcat atgccaagta cgccccctat   660
tgacgtcaat gacggtaaat ggcccgcctg gcattatgcc cagtacatga ccttatggga   720
ctttcctact tggcagtaca tctacgtatt agtcatcgct attaccatgg tgatgcggtt   780
ttggcagtac atcaatgggc gtggatagcg gtttgactca cggggatttc caagtctcca   840
ccccattgac gtcaatggga gtttgttttg gcaccaaaat caacgggact ttccaaaatg   900
tcgtaacaac tccgccccat tgacgcaaat gggcggtagg cgtgtacggt gggaggtcta   960
tataagcaga gctcgtttag tgaaccgtca gatcgcctgg agacgccatc cacgctgttt  1020
tgacctccat agaagacacc gggaccgatc cagcctccgg actctagagg atccggtact  1080
cgaggaactg aaaaaccaga aagttaactg gtaagtttag tcttttttgtc ttttatttca  1140 ggtcccggat ccggtggtgg tgcaaatcaa agaactgctc ctcagtggat gttgccttta  1200
cttctagtat caagcttgaa ttcctttgtg ttacattctt gaatgtcgct cgcagtgaca  1260
ttagcattcc ggtactgttg gtaaaatgga agacgccaaa aacataaaga aaggcccggc  1320
gccattctat cctctagagg atggaaccgc tggagagcaa ctgcataagg ctatgaagaa  1380
atacgccctg gttcctggaa caattgcttt tacagatgca catatcgagg tgaacatcac  1440
gtacgcggaa tacttcgaaa tgtccgttcg gttggcagaa gctatgaaac gatatgggct  1500
gaatacaaat cacagaatcg tcgtatgcag tgaaaactct cttcaattct ttatgccggt  1560
gttgggcgcg ttatttatcg gagttgcagt tgcgcccgcg aacgacattt ataatgaacg  1620
```

```
tgaattgctc aacagtatga acatttcgca gcctaccgta gtgtttgttt ccaaaaaggg    1680
gttgcaaaaa attttgaacg tgcaaaaaaa attaccaata atccagaaaa ttattatcat    1740
ggattctaaa acggattacc agggatttca gtcgatgtac acgttcgtca catctcatct    1800
acctcccggt tttaatgaat acgattttgt accagagtcc tttgatcgtg acaaaacaat    1860
tgcactgata atgaattcct ctggatctac tgggttacct aagggtgtgg cccttccgca    1920
tagaactgcc tgcgtcagat tctcgcatgc cagagatcct attttttggca atcaaatcat    1980 tccggatact gcgattttaa gtgttgttcc attccatcac ggttttggaa tgtttactac    2040
actcggatat ttgatatgtg gatttcgagt cgtcttaatg tatagatttg aagaagagct    2100 gttttttacga tcccttcagg attacaaaat tcaaagtgcg ttgctagtac caaccctatt    2160
ttcattcttc gccaaaagca ctctgattga caaatacgat ttatctaatt tacacgaaat    2220
tgcttctggg ggcgcacctc tttcgaaaga agtcggggaa gcggttgcaa aacgcttcca    2280
tcttccaggg atacgacaag gatatgggct cactgagact acatcagcta ttctgattac    2340
acccgagggg gatgataaac cgggcgcggt cggtaaagtt gttccatttt ttgaagcgaa    2400
ggttgtggat ctggataccg ggaaaacgct gggcgttaat cagagaggcg aattatgtgt    2460
cagaggacct atgattatgt ccggttatgt aaacaatccg gaagcgacca acgccttgat    2520
tgacaaggat ggatggctac attctggaga catagcttac tgggacgaag acgaacactt    2580
cttcatagtt gaccgcttga agtctttaat taaatacaaa ggatatcagg tggcccccgc    2640
tgaattggaa tcgatattgt tacaacaccc caacatcttc gacgcgggcg tggcaggtct    2700
tcccgacgat gacgccggtg aacttcccgc cgccgttgtt gttttggagc acggaaagac    2760
gatgacggaa aaagagatcg tggattacgt cgccagtcaa gtaacaaccg cgaaaaagtt    2820
gcgcggagga gttgtgtttg tggacgaagt accgaaaggt cttaccggaa aactcgacgc    2880
aagaaaaatc agagagatcc tcataaaggc caagaagggg ggaaagtcca aattgtaaaa    2940
tgtaactgta ttcagcgatg acgaaattct tagctattgt aatgggggat ccccaacttg    3000
tttattgcag cttataatgg ttacaaataa agcaatagca tcacaaattt cacaaataaa    3060 gcatttttt cactgcattc tagttgtggt ttgtccaaac tcatcaatgt atcttatcat    3120
gtctggatcg gatcgatccc cgggtaccga gctcgaattc gtaatcatgg tcatagctgt    3180
ttcctgtgtg aaattgttat ccgctcacaa ttccacacaa catacgagcc ggaagcataa    3240
agtgtaaagc ctggggtgcc taatgagtga gctaactcac attaattgcg ttgcgctcac    3300
tgcccgcttt ccagtcggga aacctgtcgt gccagctgca ttaatgaatc ggccaacgcg    3360
cggggagagg cggtttgcgt attgggcgct cttccgcttc ctcgctcact gactcgctgc    3420
gctcggtcgt tcggctgcgg cgagcggtat cagctcactc aaaggcggta atacggttat    3480
ccacagaatc aggggataac gcaggaaaga acatgtgagc aaaaggccag caaaaggcca    3540
ggaaccgtaa aaaggccgcg ttgctggcgt ttttccatag gctccgcccc cctgacgagc    3600
atcacaaaaa tcgacgctca agtcagaggt ggcgaaaccc gacaggacta taaagatacc    3660
aggcgtttcc ccctggaagc tccctcgtgc gctctcctgt tccgaccctg ccgcttaccg    3720
gatacctgtc cgcctttctc ccttcgggaa gcgtggcgct ttctcatagc tcacgctgta    3780
ggtatctcag ttcggtgtag tcgttcgct ccaagctggg ctgtgtgcac gaaccccccg    3840
ttcagcccga ccgctgcgcc ttatccggta actatcgtct tgagtccaac ccggtaagac    3900
acgacttatc gccactggca gcagccactg gtaacaggat tagcagagcg aggtatgtag    3960
gcggtgctac agagttcttg aagtggtggc ctaactacgg ctacactaga aggacagtat    4020
```

```
                                              -continued ttggtatctg cgctctgctg aagccagtta ccttcggaaa aagagttggt agctcttgat    4080
ccggcaaaca aaccaccgct ggtagcggtg gttttttttgt ttgcaagcag cagattacgc    4140
gcagaaaaaa aggatctcaa gaagatcctt tgatcttttc tacggggtct gacgctcagt    4200
ggaacgaaaa ctcacgttaa gggattttgg tcatgagatt atcaaaaagg atcttcacct    4260 agatccttt aaattaaaaa tgaagtttta aatcaatcta aagtatatat gagtaaactt     4320
ggtctgacag ttaccaatgc ttaatcagtg aggcacctat ctcagcgatc tgtctatttc    4380
gttcatccat agttgcctga ctccccgtcg tgtagataac tacgatacgg gagggcttac    4440
catctggccc cagtgctgca atgataccgc gagacccacg ctcaccggct ccagatttat    4500
cagcaataaa ccagccagcc ggaagggccg agcgcagaag tggtcctgca actttatccg    4560
cctccatcca gtctattaat tgtttgccgg aagctagagt aagtagttcg ccagttaata    4620
gtttgcgcaa cgttgttgcc attgctacag gcatcgtggt gtcacgctcg tcgtttggta    4680
tggcttcatt cagctccggt tcccaacgat caaggcgagt tacatgatcc cccatgttgt    4740
gcaaaaaagc ggttagctcc ttcggtgctc cgatcgttgt cagaagtaag ttggccgcag    4800
tgttatcact catggttatg gcagcactgc ataattctct tactgtcatg ccatccgtaa    4860
gatgcttttc tgtgactggt gagtactcaa ccaagtcatt ctgagaatag tgtatgcggc    4920
gaccgagttg ctcttgcccg gcgtcaatac gggataatac cgcgccacat agcagaactt    4980
taaaagtgct catcattgga aaacgttctt cggggcgaaa actctcaagg atcttaccgc    5040
tgttgagatc cagttcgatg taacccactc gtgcacccaa ctgatcttca gcatctttta    5100
ctttcaccag cgtttctggg tgagcaaaaa caggaaggca aaatgccgca aaaaagggaa    5160
taagggcgac acggaaatgt tgaatactca tactcttcct ttttcaatat tattgaagca    5220
tttatcaggg ttattgtctc atgagcggat acatatttga atgtatttag aaaaataaac    5280
aaataggggt tccgcgcaca tttccccgaa aagtgccacc tgacgtctaa gaaaccatta    5340
ttatcatgac attaacctat aaaaataggc gtatcacgag gccctatgcgg tgtgaaatac    5400 cgcacagatg cgtaaggaga aaataccgca tcaggcgcca ttcgccattc aggctgcgca    5460
actgttggga agggcgatcg gtgcgggcct cttcgctatt acgccagctg gcgaaagggg    5520
gatgtgctgc aaggcgatta agttgggtaa cgccagggtt ttcccagtca cgacgttgta    5580
aaacgacggc cagtgccaag cttgcatgcc tgcaggtcga                          5620
```

```
<210> SEQ ID NO 22
<211> LENGTH: 45
<212> TYPE: DNA
<213> ORGANISM: Artificial Sequence
<220> FEATURE:
<221> NAME/KEY: stem_loop
<222> LOCATION: 11..45
<223> OTHER INFORMATION: Description of Artificial Sequence: Asp 718
      hairpin

<400> SEQUENCE: 22
gtacactgac ctagtgccgc ccgggcaaag cccgggcggc actag                     45
```